(12) United States Patent
Deem et al.

(10) Patent No.: US 9,731,132 B2
(45) Date of Patent: Aug. 15, 2017

(54) METHODS FOR RENAL NEUROMODULATION

(71) Applicant: Medtronic Ardian Luxembourg S.a.r.l., Luxembourg (LU)

(72) Inventors: Mark Deem, Mountain View, CA (US); Denise Zarins, Saratoga, CA (US); Douglas Sutton, Pacifica, CA (US); Hanson Gifford, III, Woodside, CA (US); Howard R. Levin, Teaneck, NJ (US); Mark Gelfand, New York, NY (US); Benjamin J. Clark, Redwood City, CA (US)

(73) Assignee: Medtronic Ardian Luxembourg S.a.r.l., Luxembourg (LU)

(*) Notice: Subject to any disclaimer, the term of this patent is extended or adjusted under 35 U.S.C. 154(b) by 0 days.

(21) Appl. No.: 15/254,340

(22) Filed: Sep. 1, 2016

(65) Prior Publication Data
US 2017/0080230 A1 Mar. 23, 2017

Related U.S. Application Data

(60) Continuation of application No. 14/878,898, filed on Oct. 8, 2015, now Pat. No. 9,463,066, which is a (Continued)

(51) Int. Cl.
*A61N 1/36* (2006.01)
*A61N 1/05* (2006.01)
(Continued)

(52) U.S. Cl.
CPC ...... *A61N 1/36117* (2013.01); *A61B 18/1492* (2013.01); *A61N 1/0551* (2013.01);
(Continued)

(58) Field of Classification Search
CPC .............. A61M 5/14276; A61M 5/142; A61M 1/3627; A61M 2210/1082; A61N 1/326;
(Continued)

(56) References Cited

U.S. PATENT DOCUMENTS

| 2,130,758 A | 9/1938 | Rose |
| 2,276,995 A | 3/1942 | Milinowski |

(Continued)

FOREIGN PATENT DOCUMENTS

| CN | 101600471 | 12/2009 |
| DE | 3151180 | 8/1982 |

(Continued)

OTHER PUBLICATIONS

U.S. Appl. No. 60/813,589, filed Dec. 29, 2005, Demarais et al.
(Continued)

*Primary Examiner* — Mark W Bockelman

(57) ABSTRACT

Methods and apparatus are provided for renal neuromodulation using a pulsed electric field to effectuate electroporation or electrofusion. It is expected that renal neuromodulation (e.g., denervation) may, among other things, reduce expansion of an acute myocardial infarction, reduce or prevent the onset of morphological changes that are affiliated with congestive heart failure, and/or be efficacious in the treatment of end stage renal disease. Embodiments of the present invention are configured for extravascular delivery of pulsed electric fields to achieve such neuromodulation.

14 Claims, 19 Drawing Sheets

Related U.S. Application Data continuation of application No. 14/279,023, filed on May 15, 2014, now Pat. No. 9,186,213, which is a continuation of application No. 13/942,223, filed on Jul. 15, 2013, now Pat. No. 9,072,527, which is a continuation of application No. 13/361,542, filed on Jan. 30, 2012, now abandoned, which is a division of application No. 11/189,563, filed on Jul. 25, 2005, now Pat. No. 8,145,316, which is a continuation-in-part of application No. 11/129,765, filed on May 13, 2005, now Pat. No. 7,653,438, said application No. 11/189,563 is a continuation-in-part of application No. 10/900,199, filed on Jul. 28, 2004, now Pat. No. 6,978,174, and a continuation-in-part of application No. 10/408,665, filed on Apr. 8, 2003, now Pat. No. 7,162,303.

(60) Provisional application No. 60/616,254, filed on Oct. 5, 2004, provisional application No. 60/624,793, filed on Nov. 2, 2004, provisional application No. 60/370,190, filed on Apr. 8, 2002, provisional application No. 60/415,575, filed on Oct. 3, 2002, provisional application No. 60/442,970, filed on Jan. 29, 2003.

(51) Int. Cl.
*A61N 1/32* (2006.01)
*A61B 18/14* (2006.01)
*A61N 5/00* (2006.01)
*A61B 18/00* (2006.01)

(52) U.S. Cl.
CPC ............... *A61N 1/32* (2013.01); *A61N 1/327* (2013.01); *A61N 1/36007* (2013.01); *A61N 1/36017* (2013.01); *A61N 1/36128* (2013.01); *A61N 5/00* (2013.01); *A61B 2018/00267* (2013.01); *A61B 2018/00404* (2013.01); *A61B 2018/00434* (2013.01); *A61B 2018/00511* (2013.01); *A61B 2018/00577* (2013.01); *A61B 2018/00613* (2013.01); *A61B 2018/00702* (2013.01); *A61B 2018/00779* (2013.01); *A61B 2018/00791* (2013.01); *A61B 2018/00875* (2013.01); *A61B 2018/00982* (2013.01); *A61B 2018/1435* (2013.01)

(58) Field of Classification Search
CPC .. A61N 1/36114; A61N 1/36117; A61N 1/05; A61N 5/00; A61N 1/0551; A61N 1/36007; A61N 1/3627; A61B 18/1492; A61B 2018/00434; A61B 2018/00577
See application file for complete search history.

(56) References Cited

U.S. PATENT DOCUMENTS

| | | |
|---|---|---|
| 2,276,996 A | 3/1942 | Milinowski |
| 3,043,310 A | 7/1962 | Milinowski |
| 3,127,895 A | 4/1964 | Kendall et al. |
| 3,181,535 A | 5/1965 | Milinowski |
| 3,270,746 A | 9/1966 | Kendall et al. |
| 3,329,149 A | 7/1967 | Kendall et al. |
| 3,522,811 A | 8/1970 | Schwartz et al. |
| 3,563,246 A | 2/1971 | Puharich et al. |
| 3,650,277 A | 3/1972 | Sjostrand et al. |
| 3,670,737 A | 6/1972 | Pearo |
| 3,760,812 A | 9/1973 | Timm et al. |
| 3,774,620 A | 11/1973 | Hansjurgens et al. |
| 3,794,022 A | 2/1974 | Nawracaj et al. |
| 3,800,802 A | 4/1974 | Berry et al. |
| 3,803,463 A | 4/1974 | Cover |
| 3,894,532 A | 7/1975 | Morey |
| 3,895,639 A | 7/1975 | Rodler |
| 3,897,789 A | 8/1975 | Blanchard |
| 3,911,930 A | 10/1975 | Hagfors et al. |
| 3,952,751 A | 4/1976 | Yarger |
| 3,987,790 A | 10/1976 | Eckenhoff et al. |
| 4,011,861 A | 3/1977 | Enger |
| 4,026,300 A | 5/1977 | DeLuca et al. |
| 4,055,190 A | 10/1977 | Tany et al. |
| 4,071,033 A | 1/1978 | Nawracaj et al. |
| 4,105,017 A | 8/1978 | Ryaby et al. |
| 4,141,365 A | 2/1979 | Fischell et al. |
| 4,266,532 A | 5/1981 | Ryaby et al. |
| 4,266,533 A | 5/1981 | Ryaby et al. |
| 4,305,115 A | 12/1981 | Armitage et al. |
| 4,315,503 A | 2/1982 | Ryaby et al. |
| 4,341,221 A | 7/1982 | Testerman |
| 4,360,019 A | 11/1982 | Portner et al. |
| 4,379,462 A | 4/1983 | Borkan et al. |
| 4,405,305 A | 9/1983 | Stephen et al. |
| 4,454,883 A | 6/1984 | Fellus et al. |
| 4,467,808 A | 8/1984 | Brighton et al. |
| 4,487,603 A | 12/1984 | Harris |
| 4,530,840 A | 7/1985 | Tice et al. |
| 4,587,975 A | 5/1986 | Salo et al. |
| 4,602,624 A | 7/1986 | Naples et al. |
| 4,608,985 A | 9/1986 | Crish et al. |
| 4,649,936 A | 3/1987 | Ungar et al. |
| 4,671,286 A | 6/1987 | Renault et al. |
| 4,674,482 A | 6/1987 | Waltonen et al. |
| 4,692,147 A | 9/1987 | Duggan |
| 4,709,698 A | 12/1987 | Johnston et al. |
| 4,715,852 A | 12/1987 | Reinicke et al. |
| 4,774,967 A | 10/1988 | Zanakis et al. |
| 4,791,931 A | 12/1988 | Slate |
| 4,816,016 A | 3/1989 | Schulte et al. |
| 4,852,573 A | 8/1989 | Kennedy |
| 4,865,845 A | 9/1989 | Eckenhoff et al. |
| 4,890,623 A | 1/1990 | Cook et al. |
| 4,976,711 A | 12/1990 | Parins et al. |
| 4,979,511 A | 12/1990 | Terry, Jr. |
| 4,981,146 A | 1/1991 | Bertolucci |
| 4,998,532 A | 3/1991 | Griffith |
| 5,006,119 A | 4/1991 | Acker et al. |
| 5,014,699 A | 5/1991 | Pollack et al. |
| 5,019,034 A | 5/1991 | Weaver et al. |
| 5,057,318 A | 10/1991 | Magruder et al. |
| 5,058,584 A | 10/1991 | Bourgeois et al. |
| 5,059,423 A | 10/1991 | Magruder et al. |
| 5,061,492 A | 10/1991 | Okada et al. |
| 5,094,242 A | 3/1992 | Gleason et al. |
| 5,111,815 A | 5/1992 | Mower |
| 5,112,614 A | 5/1992 | Magruder et al. |
| 5,125,928 A | 6/1992 | Parins et al. |
| 5,131,409 A | 7/1992 | Lobarev et al. |
| 5,137,727 A | 8/1992 | Eckenhoff |
| 5,188,837 A | 2/1993 | Domb |
| 5,193,048 A | 3/1993 | Kaufman et al. |
| 5,193,539 A | 3/1993 | Schulman et al. |
| 5,193,540 A | 3/1993 | Schulman et al. |
| 5,199,428 A | 4/1993 | Obel et al. |
| 5,203,326 A | 4/1993 | Collins et al. |
| 5,213,098 A | 5/1993 | Bennett et al. |
| 5,215,086 A | 6/1993 | Terry, Jr. et al. |
| 5,231,988 A | 8/1993 | Wernicke et al. |
| 5,234,692 A | 8/1993 | Magruder et al. |
| 5,234,693 A | 8/1993 | Magruder et al. |
| 5,251,634 A | 10/1993 | Weinberg |
| 5,251,643 A | 10/1993 | Osypka et al. |
| 5,263,480 A | 11/1993 | Wernicke et al. |
| 5,269,303 A | 12/1993 | Wernicke et al. |
| 5,282,468 A | 2/1994 | Klepinski |
| 5,282,785 A | 2/1994 | Shapland et al. |
| 5,286,254 A | 2/1994 | Shapland et al. |
| 5,299,569 A | 4/1994 | Wernicke et al. |
| 5,300,068 A | 4/1994 | Rosar et al. |
| 5,304,120 A | 4/1994 | Crandell et al. |
| 5,304,206 A | 4/1994 | Baker, Jr. et al. |

(56) References Cited

U.S. PATENT DOCUMENTS

| | | |
|---|---|---|
| 5,317,155 A | 5/1994 | King |
| 5,324,255 A | 6/1994 | Passafaro et al. |
| 5,324,316 A | 6/1994 | Schulman et al. |
| 5,334,193 A | 8/1994 | Nardella |
| 5,335,657 A | 8/1994 | Terry, Jr. et al. |
| 5,338,662 A | 8/1994 | Sadri |
| 5,351,394 A | 10/1994 | Weinberg |
| 5,358,514 A | 10/1994 | Schulman et al. |
| 5,368,591 A | 11/1994 | Lennox et al. |
| 5,370,680 A | 12/1994 | Proctor |
| 5,389,069 A | 2/1995 | Weaver |
| 5,397,308 A | 3/1995 | Ellis et al. |
| 5,397,338 A | 3/1995 | Grey et al. |
| 5,400,784 A | 3/1995 | Durand et al. |
| 5,405,367 A | 4/1995 | Schulman et al. |
| 5,423,744 A | 6/1995 | Gencheff et al. |
| 5,425,364 A | 6/1995 | Imran |
| 5,429,634 A | 7/1995 | Narciso, Jr. |
| 5,433,739 A | 7/1995 | Sluijter et al. |
| 5,439,440 A | 8/1995 | Hofmann |
| 5,454,782 A | 10/1995 | Perkins |
| 5,454,809 A | 10/1995 | Janssen |
| 5,458,568 A | 10/1995 | Racchini et al. |
| 5,458,626 A | 10/1995 | Krause |
| 5,458,631 A | 10/1995 | Xavier |
| 5,470,352 A | 11/1995 | Rappaport |
| 5,472,406 A | 12/1995 | de la Torre et al. |
| 5,478,303 A | 12/1995 | Foley-Nolan et al. |
| 5,484,400 A | 1/1996 | Edwards et al. |
| 5,494,822 A | 2/1996 | Sadri |
| 5,498,238 A | 3/1996 | Shapland et al. |
| 5,499,971 A | 3/1996 | Shapland et al. |
| 5,505,201 A | 4/1996 | Grill, Jr. et al. |
| 5,505,700 A | 4/1996 | Leone et al. |
| 5,507,724 A | 4/1996 | Hofmann et al. |
| 5,507,791 A | 4/1996 | Sit'ko et al. |
| 5,531,778 A | 7/1996 | Maschino et al. |
| 5,540,730 A | 7/1996 | Terry, Jr. et al. |
| 5,540,734 A | 7/1996 | Zabara |
| 5,553,611 A | 9/1996 | Budd et al. |
| 5,560,360 A | 10/1996 | Filler et al. |
| 5,569,198 A | 10/1996 | Racchini |
| 5,571,147 A | 11/1996 | Sluijter et al. |
| 5,571,150 A | 11/1996 | Wernicke et al. |
| 5,573,552 A | 11/1996 | Hansjurgens |
| 5,584,863 A | 12/1996 | Rauch et al. |
| 5,588,964 A | 12/1996 | Imran et al. |
| 5,589,192 A | 12/1996 | Okabe et al. |
| 5,599,345 A | 2/1997 | Edwards et al. |
| 5,618,563 A | 4/1997 | Berde et al. |
| 5,626,576 A | 5/1997 | Janssen |
| 5,626,862 A | 5/1997 | Brem et al. |
| 5,628,730 A | 5/1997 | Shapland et al. |
| 5,634,462 A | 6/1997 | Tyler et al. |
| 5,634,899 A | 6/1997 | Shapland et al. |
| 5,672,174 A | 9/1997 | Gough et al. |
| 5,688,266 A | 11/1997 | Edwards et al. |
| 5,689,877 A | 11/1997 | Grill, Jr. et al. |
| 5,690,691 A | 11/1997 | Chen et al. |
| 5,700,282 A | 12/1997 | Zabara |
| 5,700,485 A | 12/1997 | Berde et al. |
| 5,704,908 A | 1/1998 | Hofmann et al. |
| 5,707,400 A | 1/1998 | Terry, Jr. et al. |
| 5,711,326 A | 1/1998 | Thies et al. |
| 5,713,847 A | 2/1998 | Howard, III et al. |
| 5,722,401 A | 3/1998 | Pietroski et al. |
| 5,723,001 A | 3/1998 | Pilla et al. |
| 5,725,563 A | 3/1998 | Klotz et al. |
| 5,728,396 A | 3/1998 | Peery et al. |
| 5,747,060 A | 5/1998 | Sackler et al. |
| 5,755,750 A | 5/1998 | Petruska et al. |
| 5,756,115 A | 5/1998 | Moo-Young et al. |
| 5,772,590 A | 6/1998 | Webster, Jr. |
| 5,792,187 A | 8/1998 | Adams |
| 5,800,464 A | 9/1998 | Kieval |
| 5,807,306 A | 9/1998 | Shapland et al. |
| 5,810,802 A | 9/1998 | Panescu et al. |
| 5,814,079 A | 9/1998 | Kieval |
| 5,824,087 A | 10/1998 | Aspden et al. |
| 5,836,935 A | 11/1998 | Ashton et al. |
| RE35,987 E | 12/1998 | Harris et al. |
| 5,843,069 A | 12/1998 | Butler et al. |
| 5,860,974 A | 1/1999 | Abele |
| 5,861,021 A | 1/1999 | Thome et al. |
| 5,865,787 A | 2/1999 | Shapland et al. |
| 5,871,449 A | 2/1999 | Brown |
| 5,891,181 A | 4/1999 | Zhu et al. |
| 5,893,885 A | 4/1999 | Webster, Jr. |
| 5,906,636 A | 5/1999 | Casscells, III et al. |
| 5,906,817 A | 5/1999 | Moullier et al. |
| 5,913,876 A | 6/1999 | Taylor et al. |
| 5,916,154 A | 6/1999 | Hobbs et al. |
| 5,916,239 A | 6/1999 | Geddes et al. |
| 5,919,187 A | 7/1999 | Guglielmi et al. |
| 5,919,220 A | 7/1999 | Stieglitz et al. |
| 5,924,997 A | 7/1999 | Campbell |
| 5,928,272 A | 7/1999 | Adkins et al. |
| 5,935,075 A | 8/1999 | Casscells et al. |
| 5,944,710 A | 8/1999 | Dev et al. |
| 5,954,719 A | 9/1999 | Chen et al. |
| 5,983,131 A | 11/1999 | Weaver et al. |
| 5,983,141 A | 11/1999 | Sluijter et al. |
| 6,004,269 A | 12/1999 | Crowley et al. |
| 6,006,134 A | 12/1999 | Hill et al. |
| 6,009,877 A | 1/2000 | Edwards |
| 6,010,613 A | 1/2000 | Walters et al. |
| 6,024,740 A | 2/2000 | Lesh et al. |
| 6,026,326 A | 2/2000 | Bardy |
| 6,036,687 A | 3/2000 | Laufer et al. |
| 6,051,017 A | 4/2000 | Loeb et al. |
| 6,058,328 A | 5/2000 | Levine et al. |
| 6,058,331 A | 5/2000 | King |
| 6,066,134 A | 5/2000 | Eggers et al. |
| 6,073,048 A | 6/2000 | Kieval et al. |
| 6,077,227 A | 6/2000 | Miesel et al. |
| 6,086,527 A | 7/2000 | Talpade |
| 6,091,995 A | 7/2000 | Ingle et al. |
| 6,093,197 A | 7/2000 | Bakula et al. |
| 6,117,101 A | 9/2000 | Diederich et al. |
| 6,122,548 A | 9/2000 | Starkebaum et al. |
| 6,123,718 A | 9/2000 | Tu et al. |
| 6,135,999 A | 10/2000 | Fanton et al. |
| 6,142,993 A | 11/2000 | Whayne et al. |
| 6,146,230 A | 11/2000 | Kim et al. |
| 6,146,380 A | 11/2000 | Racz et al. |
| 6,149,620 A | 11/2000 | Baker et al. |
| 6,161,048 A | 12/2000 | Sluijter et al. |
| 6,171,306 B1 | 1/2001 | Swanson et al. |
| 6,178,349 B1 | 1/2001 | Kieval |
| 6,190,353 B1 | 2/2001 | Makower et al. |
| 6,192,889 B1 | 2/2001 | Morrish |
| 6,205,361 B1 | 3/2001 | Kuzma et al. |
| 6,208,894 B1 | 3/2001 | Schulman et al. |
| 6,214,032 B1 | 4/2001 | Loeb et al. |
| 6,219,577 B1 | 4/2001 | Brown, III et al. |
| 6,224,592 B1 | 5/2001 | Eggers et al. |
| 6,238,702 B1 | 5/2001 | Berde et al. |
| 6,245,026 B1 | 6/2001 | Campbell et al. |
| 6,246,912 B1 | 6/2001 | Sluijter et al. |
| 6,251,130 B1 | 6/2001 | Dobak, III et al. |
| 6,254,598 B1 | 7/2001 | Edwards et al. |
| 6,258,087 B1 | 7/2001 | Edwards et al. |
| 6,259,952 B1 | 7/2001 | Sluijter et al. |
| 6,269,269 B1 | 7/2001 | Ottenhoff et al. |
| 6,272,377 B1 | 8/2001 | Sweeney et al. |
| 6,272,383 B1 | 8/2001 | Grey et al. |
| 6,273,886 B1 | 8/2001 | Edwards et al. |
| 6,280,377 B1 | 8/2001 | Talpade |
| 6,287,304 B1 | 9/2001 | Eggers et al. |
| 6,287,608 B1 | 9/2001 | Levin et al. |
| 6,292,692 B1 | 9/2001 | Skelton et al. |
| 6,292,695 B1 | 9/2001 | Webster, Jr. et al. |
| 6,304,777 B1 | 10/2001 | Ben-Haim et al. |
| 6,304,787 B1 | 10/2001 | Kuzma et al. |

(56) References Cited

U.S. PATENT DOCUMENTS

| | | |
|---|---|---|
| 6,306,423 B1 | 10/2001 | Donovan et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,326,020 B1 | 12/2001 | Kohane et al. |
| 6,326,177 B1 | 12/2001 | Schoenbach et al. |
| 6,328,699 B1 | 12/2001 | Eigler et al. |
| 6,334,069 B1 | 12/2001 | George et al. |
| 6,347,247 B1 | 2/2002 | Dev et al. |
| 6,353,763 B1 | 3/2002 | George et al. |
| 6,356,786 B1 | 3/2002 | Rezai et al. |
| 6,356,787 B1 | 3/2002 | Rezai et al. |
| 6,366,808 B1 | 4/2002 | Schroeppel et al. |
| 6,366,815 B1 | 4/2002 | Haugland et al. |
| 6,393,324 B2 | 5/2002 | Gruzdowich et al. |
| 6,400,982 B2 | 6/2002 | Sweeney et al. |
| 6,405,079 B1 | 6/2002 | Ansarinia |
| 6,405,732 B1 | 6/2002 | Edwards et al. |
| 6,413,255 B1 | 7/2002 | Stern |
| 6,415,183 B1 | 7/2002 | Scheiner et al. |
| 6,415,187 B1 | 7/2002 | Kuzma et al. |
| 6,438,423 B1 | 8/2002 | Rezai et al. |
| 6,442,424 B1 | 8/2002 | Ben-Haim et al. |
| 6,449,507 B1 | 9/2002 | Hill et al. |
| 6,450,942 B1 | 9/2002 | Lapanashvili et al. |
| 6,461,314 B1 | 10/2002 | Pant et al. |
| 6,464,687 B1 | 10/2002 | Ishikawa et al. |
| 6,473,644 B1 | 10/2002 | Terry, Jr. et al. |
| 6,482,619 B1 | 11/2002 | Rubinsky et al. |
| 6,488,679 B1 | 12/2002 | Swanson et al. |
| 6,506,189 B1 | 1/2003 | Rittman, III et al. |
| 6,508,774 B1 | 1/2003 | Acker et al. |
| 6,514,226 B1 | 2/2003 | Levin et al. |
| 6,516,211 B1 | 2/2003 | Acker et al. |
| 6,517,811 B2 | 2/2003 | John et al. |
| 6,522,926 B1 | 2/2003 | Kieval et al. |
| 6,522,932 B1 | 2/2003 | Kuzma et al. |
| 6,524,607 B1 | 2/2003 | Goldenheim et al. |
| 6,534,081 B2 | 3/2003 | Goldenheim et al. |
| 6,536,949 B1 | 3/2003 | Heuser |
| 6,542,781 B1 | 4/2003 | Koblish et al. |
| 6,562,034 B2 | 5/2003 | Edwards et al. |
| 6,564,096 B2 | 5/2003 | Mest |
| 6,571,127 B1 | 5/2003 | Ben-Haim et al. |
| 6,592,567 B1 | 7/2003 | Levin et al. |
| 6,599,256 B1 | 7/2003 | Acker et al. |
| 6,600,954 B2 | 7/2003 | Cohen et al. |
| 6,600,956 B2 | 7/2003 | Maschino et al. |
| 6,601,459 B1 | 8/2003 | Jenni et al. |
| 6,605,084 B2 | 8/2003 | Acker et al. |
| 6,613,045 B1 | 9/2003 | Laufer et al. |
| 6,615,071 B1 | 9/2003 | Casscells, III et al. |
| 6,616,624 B1 | 9/2003 | Kieval |
| 6,620,151 B2 | 9/2003 | Blischak et al. |
| 6,622,041 B2 | 9/2003 | Terry, Jr. et al. |
| 6,622,731 B2 | 9/2003 | Daniel et al. |
| 6,635,054 B2 | 10/2003 | Fjield et al. |
| 6,640,120 B1 | 10/2003 | Swanson et al. |
| 6,654,636 B1 | 11/2003 | Dev et al. |
| 6,666,845 B2 | 12/2003 | Hooper et al. |
| 6,669,655 B1 | 12/2003 | Acker et al. |
| 6,671,556 B2 | 12/2003 | Osorio et al. |
| 6,672,312 B2 | 1/2004 | Acker |
| 6,676,657 B2 | 1/2004 | Wood |
| 6,681,136 B2 | 1/2004 | Schuler et al. |
| 6,684,105 B2 | 1/2004 | Cohen et al. |
| 6,690,971 B2 | 2/2004 | Schauerte et al. |
| 6,692,738 B2 | 2/2004 | MacLaughlin et al. |
| 6,697,670 B2 | 2/2004 | Chomenky et al. |
| 6,711,444 B2 | 3/2004 | Koblish |
| 6,718,208 B2 | 4/2004 | Hill et al. |
| 6,735,471 B2 | 5/2004 | Hill et al. |
| 6,738,663 B2 | 5/2004 | Schroeppel et al. |
| 6,745,079 B2 | 6/2004 | King |
| 6,749,598 B1 | 6/2004 | Keren et al. |
| 6,752,805 B2 | 6/2004 | Maguire et al. |
| 6,786,904 B2 | 9/2004 | Doscher et al. |
| 6,795,728 B2 | 9/2004 | Chornenky et al. |
| 6,845,267 B2 | 1/2005 | Harrison et al. |
| 6,850,801 B2 | 2/2005 | Kieval et al. |
| 6,862,479 B1 | 3/2005 | Whitehurst et al. |
| 6,865,416 B2 | 3/2005 | Dev et al. |
| 6,869,431 B2 | 3/2005 | Maguire et al. |
| 6,885,888 B2 | 4/2005 | Rezai |
| 6,916,656 B2 | 7/2005 | Walters et al. |
| 6,917,834 B2 | 7/2005 | Koblish et al. |
| 6,923,808 B2 | 8/2005 | Taimisto |
| 6,927,049 B2 | 8/2005 | Rubinsky et al. |
| 6,936,047 B2 | 8/2005 | Nasab et al. |
| 6,939,345 B2 | 9/2005 | KenKnight et al. |
| 6,939,346 B2 | 9/2005 | Kannenberg et al. |
| 6,949,097 B2 | 9/2005 | Stewart et al. |
| 6,958,060 B2 | 10/2005 | Mathiesen et al. |
| 6,969,388 B2 | 11/2005 | Goldman et al. |
| 6,972,013 B1 | 12/2005 | Zhang et al. |
| 6,978,174 B2 | 12/2005 | Gelfand et al. |
| 6,985,774 B2 | 1/2006 | Kieval et al. |
| 6,994,700 B2 | 2/2006 | Elkins et al. |
| 6,994,706 B2 | 2/2006 | Chornenky et al. |
| 7,004,911 B1 | 2/2006 | Tu et al. |
| 7,054,685 B2 | 5/2006 | Dimmer et al. |
| 7,063,679 B2 | 6/2006 | Maguire et al. |
| 7,081,114 B2 | 7/2006 | Rashidi |
| 7,081,115 B2 | 7/2006 | Taimisto |
| 7,083,614 B2 | 8/2006 | Fjield et al. |
| 7,122,019 B1 | 10/2006 | Kesten et al. |
| 7,155,284 B1 | 12/2006 | Whitehurst et al. |
| 7,162,303 B2 | 1/2007 | Levin et al. |
| 7,191,015 B2 | 3/2007 | Lamson et al. |
| 7,373,204 B2 | 5/2008 | Gelfand et al. |
| 7,444,183 B2 | 10/2008 | Knudson et al. |
| 7,486,991 B2 | 2/2009 | Libbus et al. |
| 7,617,005 B2 | 11/2009 | Demarais et al. |
| 7,620,451 B2 | 11/2009 | Demarais et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,756,583 B2 | 7/2010 | Demarais et al. |
| 7,894,905 B2 | 2/2011 | Pless et al. |
| 8,131,371 B2 | 3/2012 | Demarals et al. |
| 8,131,372 B2 | 3/2012 | Levin et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,350,846 B2 | 1/2013 | Mejdrich et al. |
| 8,515,536 B2 | 8/2013 | Levin et al. |
| 8,788,065 B2 | 7/2014 | Rezai et al. |
| 8,805,512 B1 | 8/2014 | Greiner et al. |
| 8,938,297 B2 | 1/2015 | Greiner et al. |
| 8,942,808 B2 | 1/2015 | Peterson et al. |
| 8,942,816 B2 | 1/2015 | Greiner et al. |
| 8,954,143 B2 | 2/2015 | Thenuwara et al. |
| 8,965,511 B2 | 2/2015 | Greiner et al. |
| 8,996,125 B2 | 3/2015 | Greiner et al. |
| 9,066,845 B2 | 6/2015 | Peterson et al. |
| 9,078,801 B2 | 7/2015 | Greiner et al. |
| 9,089,716 B2 | 7/2015 | Peterson et al. |
| 9,173,811 B2 | 11/2015 | Greiner et al. |
| 9,198,828 B2 | 12/2015 | Greiner et al. |
| 2001/0044596 A1 | 11/2001 | Jaafar |
| 2002/0002329 A1 | 1/2002 | Avitall |
| 2002/0026222 A1 | 2/2002 | Schauerte et al. |
| 2002/0026228 A1 | 2/2002 | Schauerte |
| 2002/0032468 A1 | 3/2002 | Hill et al. |
| 2002/0038137 A1 | 3/2002 | Stein |
| 2002/0040204 A1 | 4/2002 | Dev et al. |
| 2002/0045853 A1 | 4/2002 | Dev et al. |
| 2002/0065541 A1 | 5/2002 | Fredricks et al. |
| 2002/0072782 A1 | 6/2002 | Osorio et al. |
| 2002/0107553 A1 | 8/2002 | Hill et al. |
| 2002/0116030 A1 | 8/2002 | Rezai |
| 2002/0120304 A1 | 8/2002 | Mest |

(56) References Cited

U.S. PATENT DOCUMENTS

| | | |
|---|---|---|
| 2002/0139379 A1 | 10/2002 | Edwards et al. |
| 2002/0165532 A1 | 11/2002 | Hill et al. |
| 2002/0165586 A1 | 11/2002 | Hill et al. |
| 2002/0169413 A1 | 11/2002 | Keren et al. |
| 2002/0177846 A1 | 11/2002 | Mulier et al. |
| 2002/0183682 A1 | 12/2002 | Darvish et al. |
| 2002/0183684 A1 | 12/2002 | Dev et al. |
| 2002/0183686 A1 | 12/2002 | Darvish et al. |
| 2002/0188325 A1 | 12/2002 | Hill et al. |
| 2002/0198512 A1 | 12/2002 | Seward |
| 2003/0004549 A1 | 1/2003 | Hill et al. |
| 2003/0009145 A1 | 1/2003 | Struijker-Boudier et al. |
| 2003/0018367 A1 | 1/2003 | DiLorenzo |
| 2003/0040774 A1 | 2/2003 | Terry et al. |
| 2003/0045909 A1 | 3/2003 | Gross et al. |
| 2003/0050635 A1 | 3/2003 | Truckai et al. |
| 2003/0050681 A1 | 3/2003 | Pianca et al. |
| 2003/0060848 A1 | 3/2003 | Kieval et al. |
| 2003/0060857 A1* | 3/2003 | Perrson ............... A61N 1/05 607/44 |
| 2003/0060858 A1 | 3/2003 | Kieval et al. |
| 2003/0074039 A1 | 4/2003 | Puskas |
| 2003/0100924 A1 | 5/2003 | Foreman et al. |
| 2003/0120270 A1 | 6/2003 | Acker |
| 2003/0125790 A1 | 7/2003 | Fastovsky et al. |
| 2003/0150464 A1 | 8/2003 | Casscells |
| 2003/0158584 A1 | 8/2003 | Cates et al. |
| 2003/0181897 A1 | 9/2003 | Thomas et al. |
| 2003/0181963 A1 | 9/2003 | Pellegrino et al. |
| 2003/0199747 A1 | 10/2003 | Michlitsch et al. |
| 2003/0199767 A1 | 10/2003 | Cespedes et al. |
| 2003/0199768 A1 | 10/2003 | Cespedes et al. |
| 2003/0199806 A1 | 10/2003 | Kieval |
| 2003/0199863 A1 | 10/2003 | Swanson et al. |
| 2003/0204161 A1 | 10/2003 | Ferek-Petric |
| 2003/0216792 A1 | 11/2003 | Levin et al. |
| 2003/0220521 A1 | 11/2003 | Reitz et al. |
| 2003/0229340 A1 | 12/2003 | Sherry et al. |
| 2003/0233099 A1 | 12/2003 | Danaek et al. |
| 2003/0236443 A1 | 12/2003 | Cespedes et al. |
| 2004/0010289 A1 | 1/2004 | Biggs et al. |
| 2004/0010303 A1 | 1/2004 | Bolea et al. |
| 2004/0019364 A1 | 1/2004 | Kieval et al. |
| 2004/0019371 A1 | 1/2004 | Jaafar et al. |
| 2004/0064090 A1 | 4/2004 | Keren et al. |
| 2004/0064091 A1 | 4/2004 | Keren et al. |
| 2004/0065615 A1 | 4/2004 | Hooper et al. |
| 2004/0073238 A1 | 4/2004 | Makower |
| 2004/0082978 A1 | 4/2004 | Harrison et al. |
| 2004/0101523 A1 | 5/2004 | Reitz et al. |
| 2004/0106953 A1 | 6/2004 | Yomtov et al. |
| 2004/0111080 A1 | 6/2004 | Harper et al. |
| 2004/0127942 A1 | 7/2004 | Yomtov et al. |
| 2004/0162590 A1 | 8/2004 | Whitehurst et al. |
| 2004/0163655 A1 | 8/2004 | Gelfand et al. |
| 2004/0167415 A1 | 8/2004 | Gelfand et al. |
| 2004/0176699 A1 | 9/2004 | Walker et al. |
| 2004/0176757 A1 | 9/2004 | Sinelnikov et al. |
| 2004/0193228 A1 | 9/2004 | Gerber |
| 2004/0215186 A1 | 10/2004 | Cornelius et al. |
| 2004/0220511 A1 | 11/2004 | Scott et al. |
| 2004/0243102 A1 | 12/2004 | Berg et al. |
| 2004/0243206 A1 | 12/2004 | Tadlock |
| 2004/0249416 A1 | 12/2004 | Yun et al. |
| 2004/0254616 A1 | 12/2004 | Rossing et al. |
| 2005/0010263 A1 | 1/2005 | Schauerte |
| 2005/0021092 A1 | 1/2005 | Yun et al. |
| 2005/0038409 A1 | 2/2005 | Segal et al. |
| 2005/0049542 A1 | 3/2005 | Sigg et al. |
| 2005/0065562 A1 | 3/2005 | Rezai |
| 2005/0065573 A1 | 3/2005 | Rezai |
| 2005/0065574 A1 | 3/2005 | Rezai |
| 2005/0075681 A1 | 4/2005 | Rezai et al. |
| 2005/0080409 A1 | 4/2005 | Young et al. |
| 2005/0080459 A1 | 4/2005 | Jacobson et al. |
| 2005/0096647 A1 | 5/2005 | Steinke et al. |
| 2005/0096710 A1 | 5/2005 | Kieval |
| 2005/0153885 A1 | 7/2005 | Yun et al. |
| 2005/0154418 A1 | 7/2005 | Kieval et al. |
| 2005/0171523 A1 | 8/2005 | Rubinsky et al. |
| 2005/0171574 A1 | 8/2005 | Rubinsky et al. |
| 2005/0171575 A1 | 8/2005 | Dev et al. |
| 2005/0187579 A1 | 8/2005 | Danek et al. |
| 2005/0197624 A1 | 9/2005 | Goodson et al. |
| 2005/0209548 A1 | 9/2005 | Dev et al. |
| 2005/0209642 A1 | 9/2005 | Palti |
| 2005/0228460 A1 | 10/2005 | Levin et al. |
| 2005/0234523 A1 | 10/2005 | Levin et al. |
| 2005/0240126 A1 | 10/2005 | Foley et al. |
| 2005/0240173 A1 | 10/2005 | Palti |
| 2005/0240228 A1 | 10/2005 | Palti |
| 2005/0240241 A1 | 10/2005 | Yun et al. |
| 2005/0245882 A1 | 11/2005 | Elkins et al. |
| 2005/0245892 A1 | 11/2005 | Elkins et al. |
| 2005/0251212 A1 | 11/2005 | Kieval et al. |
| 2005/0261672 A1 | 11/2005 | Deem et al. |
| 2005/0267010 A1 | 12/2005 | Goodson et al. |
| 2005/0282284 A1 | 12/2005 | Rubinsky et al. |
| 2006/0004417 A1 | 1/2006 | Rossing et al. |
| 2006/0004430 A1 | 1/2006 | Rossing et al. |
| 2006/0025821 A1 | 2/2006 | Gelfand et al. |
| 2006/0030814 A1 | 2/2006 | Valencia et al. |
| 2006/0036218 A1 | 2/2006 | Goodson et al. |
| 2006/0041277 A1 | 2/2006 | Deem et al. |
| 2006/0041283 A1 | 2/2006 | Gelfand et al. |
| 2006/0067972 A1 | 3/2006 | Kesten et al. |
| 2006/0069323 A1 | 3/2006 | Elkins et al. |
| 2006/0074453 A1 | 4/2006 | Kieval et al. |
| 2006/0079859 A1 | 4/2006 | Elkins et al. |
| 2006/0085046 A1 | 4/2006 | Rezai et al. |
| 2006/0085054 A1 | 4/2006 | Zikorus et al. |
| 2006/0089674 A1 | 4/2006 | Walters et al. |
| 2006/0095029 A1 | 5/2006 | Young et al. |
| 2006/0100618 A1 | 5/2006 | Chan et al. |
| 2006/0100667 A1 | 5/2006 | Machado et al. |
| 2006/0106429 A1 | 5/2006 | Libbus et al. |
| 2006/0111754 A1 | 5/2006 | Rezai et al. |
| 2006/0116720 A1 | 6/2006 | Knoblich |
| 2006/0121016 A1 | 6/2006 | Lee |
| 2006/0121610 A1 | 6/2006 | Rubinsky et al. |
| 2006/0135998 A1 | 6/2006 | Libbus et al. |
| 2006/0136004 A1 | 6/2006 | Cowan et al. |
| 2006/0149350 A1 | 7/2006 | Patel et al. |
| 2006/0155344 A1 | 7/2006 | Rezai et al. |
| 2006/0167437 A1 | 7/2006 | Valencia |
| 2006/0167498 A1 | 7/2006 | DiLorenzo |
| 2006/0167499 A1 | 7/2006 | Palti |
| 2006/0189941 A1 | 8/2006 | Seward et al. |
| 2006/0189960 A1 | 8/2006 | Kesten et al. |
| 2006/0206149 A1 | 9/2006 | Yun |
| 2006/0206150 A1 | 9/2006 | Demarais et al. |
| 2006/0212078 A1 | 9/2006 | Demarais et al. |
| 2006/0229677 A1 | 10/2006 | Moffitt et al. |
| 2006/0235474 A1 | 10/2006 | Demarais |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276852 A1 | 12/2006 | Demarais et al. |
| 2007/0066957 A1 | 3/2007 | Demarais et al. |
| 2007/0066972 A1 | 3/2007 | Ormsby et al. |
| 2007/0083239 A1 | 4/2007 | Demarais et al. |
| 2007/0118038 A1 | 5/2007 | Bodecker et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0142864 A1 | 6/2007 | Libbus et al. |
| 2007/0156200 A1 | 7/2007 | Kornet et al. |
| 2007/0173899 A1 | 7/2007 | Levin et al. |
| 2007/0208382 A1 | 9/2007 | Yun |
| 2007/0265687 A1 | 11/2007 | Deem et al. |
| 2007/0282376 A1 | 12/2007 | Shuros et al. |
| 2007/0288070 A1 | 12/2007 | Libbus et al. |
| 2008/0004673 A1 | 1/2008 | Rossing et al. |

(56) References Cited

U.S. PATENT DOCUMENTS

| | | |
|---|---|---|
| 2008/0015659 A1 | 1/2008 | Zhang et al. |
| 2008/0039904 A1 | 2/2008 | Bulkes et al. |
| 2008/0091255 A1 | 4/2008 | Caparso et al. |
| 2008/0140150 A1 | 6/2008 | Zhou et al. |
| 2008/0161701 A1 | 7/2008 | Bullens et al. |
| 2008/0213331 A1 | 9/2008 | Gelfand et al. |
| 2008/0215117 A1 | 9/2008 | Gross |
| 2008/0234790 A1 | 9/2008 | Bayer et al. |
| 2008/0255642 A1 | 10/2008 | Zarins et al. |
| 2008/0319513 A1 | 12/2008 | Pu et al. |
| 2009/0024195 A1 | 1/2009 | Rezai et al. |
| 2009/0036948 A1 | 2/2009 | Levin et al. |
| 2009/0062667 A1 | 3/2009 | Fayram et al. |
| 2009/0062873 A1 | 3/2009 | Wu et al. |
| 2009/0076409 A1 | 3/2009 | Wu et al. |
| 2009/0192558 A1 | 7/2009 | Whitehurst et al. |
| 2009/0204170 A1 | 8/2009 | Hastings et al. |
| 2010/0010567 A1 | 1/2010 | Deem et al. |
| 2010/0048983 A1 | 2/2010 | Ball et al. |
| 2010/0057150 A1 | 3/2010 | Demarais et al. |
| 2010/0137860 A1 | 6/2010 | Demarais et al. |
| 2010/0137952 A1 | 6/2010 | Demarais et al. |
| 2010/0168731 A1 | 7/2010 | Wu et al. |
| 2010/0168739 A1 | 7/2010 | Wu et al. |
| 2010/0174282 A1 | 7/2010 | Demarais et al. |
| 2010/0191112 A1 | 7/2010 | Demarais et al. |
| 2010/0222851 A1 | 9/2010 | Deem et al. |
| 2010/0222854 A1 | 9/2010 | Demarais et al. |
| 2010/0241183 A1 | 9/2010 | DiLorenzo |
| 2010/0249773 A1 | 9/2010 | Clark et al. |
| 2010/0268307 A1 | 10/2010 | Demarais et al. |
| 2011/0060324 A1 | 3/2011 | Wu et al. |
| 2011/0086257 A1 | 4/2011 | Pitteloud et al. |
| 2011/0112400 A1 | 5/2011 | Emery et al. |
| 2011/0137298 A1 | 6/2011 | Nguyen et al. |
| 2011/0200171 A1 | 8/2011 | Beetel et al. |
| 2011/0202098 A1 | 8/2011 | Demarais et al. |
| 2011/0257564 A1 | 10/2011 | Demarais et al. |
| 2011/0264011 A1 | 10/2011 | Wu et al. |
| 2011/0264075 A1 | 10/2011 | Leung et al. |
| 2012/0130345 A1 | 5/2012 | Levin et al. |
| 2012/0197252 A1 | 8/2012 | Deem et al. |
| 2013/0013024 A1 | 1/2013 | Levin et al. |
| 2013/0053732 A1 | 2/2013 | Heuser |
| 2013/0218029 A1 | 8/2013 | Cholette et al. |
| 2013/0237948 A1 | 9/2013 | Donders et al. |
| 2013/0237954 A1 | 9/2013 | Shuros et al. |
| 2013/0253603 A1 | 9/2013 | Levin et al. |
| 2013/0289650 A1 | 10/2013 | Karlsson et al. |
| 2013/0345606 A1 | 12/2013 | Ehrenreich et al. |
| 2013/0345608 A1 | 12/2013 | Ehrenreich et al. |
| 2014/0067003 A1 | 3/2014 | Vase et al. |
| 2014/0148883 A1 | 5/2014 | Stack et al. |
| 2014/0214112 A1 | 7/2014 | Greiner et al. |
| 2014/0214113 A1 | 7/2014 | Greiner et al. |
| 2014/0214117 A1 | 7/2014 | Greiner et al. |
| 2014/0214118 A1 | 7/2014 | Greiner et al. |
| 2014/0214119 A1 | 7/2014 | Greiner et al. |
| 2014/0214125 A1 | 7/2014 | Greiner et al. |
| 2014/0214126 A1 | 7/2014 | Greiner et al. |
| 2014/0214128 A1 | 7/2014 | Peterson et al. |
| 2014/0214134 A1 | 7/2014 | Peterson |
| 2014/0214144 A1 | 7/2014 | Peterson et al. |
| 2015/0012055 A1 | 1/2015 | Greiner et al. |
| 2015/0148864 A1 | 5/2015 | Peterson et al. |
| 2015/0196761 A1 | 7/2015 | Greiner et al. |
| 2015/0231030 A1 | 8/2015 | Greiner et al. |
| 2015/0265498 A1 | 9/2015 | Peterson et al. |
| 2015/0305974 A1 | 10/2015 | Ehrenreich et al. |
| 2015/0313750 A1 | 11/2015 | Greiner et al. |
| 2015/0321006 A1 | 11/2015 | Greiner et al. |
| 2015/0321007 A1 | 11/2015 | Greiner et al. |
| 2015/0321014 A1 | 11/2015 | Peterson et al. |
| 2015/0328460 A1 | 11/2015 | Greiner et al. |
| 2016/0008220 A1 | 1/2016 | Greiner et al. |
| 2016/0008221 A1 | 1/2016 | Greiner et al. |
| 2016/0008222 A1 | 1/2016 | Greiner et al. |

FOREIGN PATENT DOCUMENTS

| | | |
|---|---|---|
| EP | 0811395 | 12/1997 |
| EP | 1804905 | 7/2007 |
| EP | 2092957 | 8/2009 |
| WO | WO-8501213 | 3/1985 |
| WO | WO-9104725 | 4/1991 |
| WO | WO-9220291 | 11/1992 |
| WO | WO-9302740 | 2/1993 |
| WO | WO-9307803 | 4/1993 |
| WO | WO-9400188 | 1/1994 |
| WO | WO-9407446 | 4/1994 |
| WO | WO-9411057 | 5/1994 |
| WO | WO-9525472 | 9/1995 |
| WO | WO-9531142 | 11/1995 |
| WO | WO-9533514 | 12/1995 |
| WO | WO-9600039 | 1/1996 |
| WO | WO-9604957 | 2/1996 |
| WO | WO-9611723 | 4/1996 |
| WO | WO-9713463 | 4/1997 |
| WO | WO-9713550 | 4/1997 |
| WO | WO-9736548 | 10/1997 |
| WO | WO-9749453 | 12/1997 |
| WO | WO-9837926 | 9/1998 |
| WO | WO-9842403 | 10/1998 |
| WO | WO-9843700 | 10/1998 |
| WO | WO-9843701 | 10/1998 |
| WO | WO-9848888 | 11/1998 |
| WO | WO-9900060 | 1/1999 |
| WO | WO-9933407 | 7/1999 |
| WO | WO-9951286 | 10/1999 |
| WO | WO-9952424 | 10/1999 |
| WO | WO-0122897 | 4/2001 |
| WO | WO-0126729 | 4/2001 |
| WO | WO-0170114 | 9/2001 |
| WO | WO-0209808 | 2/2002 |
| WO | WO-0226314 | 4/2002 |
| WO | WO-02053207 | 7/2002 |
| WO | WO-02070039 | 9/2002 |
| WO | WO-02070047 | 9/2002 |
| WO | WO-02085192 | 10/2002 |
| WO | WO-02085448 | 10/2002 |
| WO | WO-03018108 | 3/2003 |
| WO | WO-03022167 | 3/2003 |
| WO | WO-03028802 | 4/2003 |
| WO | WO-03063692 | 8/2003 |
| WO | WO-03071140 | 8/2003 |
| WO | WO-03076008 | 9/2003 |
| WO | WO-03082080 | 10/2003 |
| WO | WO-03082403 | 10/2003 |
| WO | WO-2004026370 | 4/2004 |
| WO | WO-2004026371 | 4/2004 |
| WO | WO-2004026374 | 4/2004 |
| WO | WO-2004030718 | 4/2004 |
| WO | WO-2004032791 | 4/2004 |
| WO | WO-2004107965 | 12/2004 |
| WO | WO-2005014100 | 2/2005 |
| WO | WO-2005016165 | 2/2005 |
| WO | WO-2005030072 | 4/2005 |
| WO | WO-2005032646 | 4/2005 |
| WO | WO-2005041748 | 5/2005 |
| WO | WO-2005065284 | 7/2005 |
| WO | WO-2005084389 | 9/2005 |
| WO | WO-2005097256 | 10/2005 |
| WO | WO-2005110528 | 11/2005 |
| WO | WO-2005123183 | 12/2005 |
| WO | WO-2006007048 | 1/2006 |
| WO | WO-2006018528 | 2/2006 |
| WO | WO-2006022790 | 3/2006 |
| WO | WO-2006031899 | 3/2006 |
| WO | WO-2006041847 | 4/2006 |
| WO | WO-2006041881 | 4/2006 |
| WO | WO-2006105121 | 10/2006 |
| WO | WO-2007008954 | 1/2007 |
| WO | WO-2007035537 | 3/2007 |

(56) References Cited

FOREIGN PATENT DOCUMENTS

| | | |
|---|---|---|
| WO | WO-2007078997 | 7/2007 |
| WO | WO-2007086965 | 8/2007 |
| WO | WO-2007103879 | 9/2007 |
| WO | WO-2007103881 | 9/2007 |
| WO | WO-2007121309 | 10/2007 |
| WO | WO-2007146834 | 12/2007 |
| WO | WO-2008003058 | 1/2008 |
| WO | WO-2008049084 | 4/2008 |
| WO | WO-2008061150 | 5/2008 |
| WO | WO-2008061152 | 5/2008 |
| WO | WO-2008070413 | 6/2008 |
| WO | WO-2010078175 | 7/2010 |
| WO | WO-2013169930 | 11/2013 |

OTHER PUBLICATIONS

2003 European Society of Hypertension—European Society of Cardiology guidelines for the management of arterial hypertension, Guidelines Committee, Journal of Hypertension 2003, vol. 21, No. 6, pp. 1011-1053.
Aars, H. and S. Akre, Reflex Changes in Sympathetic Activity and Arterial Blood Pressure Evoked by Afferent Stimulation of the Renal Nerve, Feb. 26, 1999, Acta physiol. Scand., vol. 78, 1970, pp. 184-188.
Abramov, G.S. et al., Alteration in sensory nerve function following electrical shock, Burns vol. 22, No. 8, 1996 Elsevier Science Ltd., pp. 602-606.
Achar, Suraj, M.D., and Suriti Kundu, M.D., Principles of Office Anesthesia: Part I. Infiltrative Anesthesia, Office Procedures, American Family Physician, Jul. 1, 2002, vol. 66, No. 1, pp. 91-94.
Advanced Neuromodulation Systems' Comparison Chart, Dec. 16, 2008, pp. 1.
Advances in the role of the sympathetic nervous system in cardiovascular medicine, 2001 SNS Report, No. 3, Springer, Published with an educational grant from Servier, pp. 1-8.
Aggarwal, A. et al., Regional sympathetic effects of low-dose clonidine in heart failure. Hypertension. 2003;41:553-7.
Agnew, William F. et al., Evolution and Resolution of Stimulation-Induced Axonal Injury in Peripheral Nerve, May 21, 1999, Muscle & Nerve, vol. 22, Oct. 1999, John Wiley & Sons, Inc. 1999, pp. 1393-1402.
Ahadian, Farshad M., M.D., Pulsed Radiofrequency Neurotomy: Advances in Pain Medicine, Current Pain and Headache Reports 2004, vol. 8, 2004 Current Science Inc., pp. 34-40.
Alexander, B.T. et al., Renal denervation abolishes hypertension in low-birth-weight offspring from pregnant rats with reduced uterine perfusion, Hypertension, 2005; 45 (part 2): pp. 754-758.
Alford, J. Winslow, M.D. and Paul D. Fadale, M.D., Evaluation of Postoperative Bupivacaine Infusion for Pain Management After Anterior Cruciate Ligament Reconstruction, The Journal of Arthroscopic and Related Surgery, vol. 19, No. 8, Oct. 2003 Arthroscopy Association of North America, pp. 855-861.
Allen, E.V., Sympathectomy for essential hypertension, Circulation, 1952, 6:131-140.
Amersham Health. Hypaque-Cysto, 2003, 6 pages.
Andrews, B.T. et al., The use of surgical sympathectomy in the treatment of chronic renal pain. Br J Urol. 1997; 80: 6-10.
Antman, Elliott M. and Eugene Braunwald, Chapter 37—Acute Myocardial Infarction, Heart Disease—A Textbook of Cardiovascular Medicine, 5th Edition, vol. 2, 1997, Edited by Eugene Braunwald, pp. 1184-1288.
Archer, Steffen et al., Cell Reactions to Dielectrophoretic Manipulation, Mar. 1, 1999, Biochemical and Biophysical Research Communications, 1999 Academic Press, pp. 687-698.
Arentz, T. et al., Incidence of pulmonary vein stenosis 2 years after radiofrequency catheter ablation of refractory atrial fibrillation. European Heart Journal. 2003. 24; pp. 963-969.
Arias, M.D., Manuel J., Percutaneous Radio-Frequency Thermocoagulation with Low Temperature in the Treatment of Essential Glossopharyngeal Neuralgia, Surg. Neurol. 1986, vol. 25, 1986 Elsevier Science Publishing Co., Inc., pp. 94-96.
Aronofsky, David H., D.D.S., Reduction of dental postsurgical symptoms using nonthermal pulsed high-peak-power electromagnetic energy, Oral Surg., Nov. 1971, vol. 32, No. 5, pp. 688-696.
Aspelin, Peter, M.D., Ph.D. et al., Nephrotoxic Effects in High-Risk Patients Undergoing Angiography, Feb. 6, 2003, New England Journal of Medicine 2003, vol. 348, No. 6, 2003 Massachusetts Medical Society, pp. 491-499.
Atrial Fibrillation Heart and Vascular Health on Yahoo! Health. 2 pgs. <URL: http://health.yahoo.com/topic/heart/overview/article/healthwise/hw160872;_ylt=AiBT43Ey74HQ7ft3jAb4C.sPu7cF> Feb. 21, 2006.
Augustyniak, Robert A. et al., Sympathetic Overactivity as a Cause of Hypertension in Chronic Renal Failure, Aug. 14, 2001, Journal of Hypertension 2002, vol. 20, 2002 Lippincott Williams & Wilkins, pp. 3-9.
Awwad, Ziad M., FRCS and Bashir A. Atiyat, GBA, JBA, Pain relief using continuous bupivacaine infusion in the paravertebral space after loin incision, May 15, 2004, Saudi Med J 2004, vol. 25 (10), pp. 1369-1373.
Badyal, D. K., H. Lata and A.P. Dadhich, Animal Models of Hypertension and Effect of Drugs, Aug. 19, 2003, Indian Journal of Pharmacology 2003, vol. 35, pp. 349-362.
Baker, Carol E. et al., Effect of pH of Bupivacaine on Duration of Repeated Sciatic Nerve Blocks in the Albino Rat, Anesth Analg, 1991, vol. 72, The International Anesthesia Research Society 1991, pp. 773-778.
Balazs, Tibor, Development of Tissue Resistance to Toxic Effects of Chemicals, Jan. 26, 1974, Toxicology, 2 (1974), Elsevier/North-Holland, Amsterdam, pp. 247-255.
Barajas, L. Innervation of the renal cortex. Fex Proc. 1978;37:1192-201.
Barrett, Carolyn J. et al., Long-term control of renal blood flow: what is the role of the renal nerves?, Jan. 4, 2001, Am J Physiol Regulatory Integrative Comp Physiol 280, 2001, the American Physiological Society 2001, pp. R1534-R1545.
Barrett, Carolyn J. et al., What Sets the Long-Term Level of Renal Sympathetic Nerve Activity, May 12, 2003, Integrative Physiology, Circ Res. 2003, vol. 92, 2003 American Heart Association, pp. 1330-1336.
Bassett, C. Andrew L. et al., Augmentation of Bone Repair by Inductively Coupled Electromagnetic Fields, May 3, 1974, Science, vol. 184, pp. 575-577.
Bassett, C. Andrew L., Fundamental and Practical Aspects of Therapeutic Uses of Pulsed Electromagnetic Fields (PEMFs), Critical Reviews in Biomedical Engineering, vol. 17, Issue 5, 1989, pp. 451-514.
Beebe, Stephen J. et al., Nanosecond pulsed electric fields modulate cell function through intracellular signal transduction mechanisms, Apr. 8, 2004, Physiol. Meas. 25, 2004, IOP Publishing Ltd. 2004, pp. 1077-1093.
Beebe, Stephen J., et al., Nanosecond Pulsed Electric Field (nsPEF) Effects on Cells and Tissues: Apoptosis Induction and Tumor Growth Inhibition, Oct. 11, 2001, IEEE Transactions on Plasma Science, vol. 30, No. 1, Feb. 2002, IEEE 2002, pp. 286-292.
Bello-Reuss, E. et al., Acute unilateral renal denervation in rats with extracellular volume expansion, Departments of Medicine and Physiology, University of North Carolina School of Medicine. F26-F32 Jul. 1975.
Bello-Reuss, E. et al., Effect of renal sympathetic nerve stimulation on proximal water and sodium reabsorption, J Clin Invest, 1976;57:1104-1107.
Bello-Reuss, E. et al., Effects of Acute Unilateral Renal Denervation in the Rat, J Clin Invest, 1975;56:208-217.
Berde, C.et al., Local Anesthetics, Anesthesia, Chapter 13, 5th addition, Churchill-Livingston, Philadelphia 2000, pp. 491-521.
Bhadra, Niloy and Kevin L. Kilgore, Direct Current Electrical Conduction Block of Peripheral Nerve, Feb. 25, 2004, IEEE Transactions on Neural Systems and Rehabilitation Engineering, vol. 12, No. 3, Sep. 2004, pp. 313-324.

(56) References Cited

OTHER PUBLICATIONS

Bhandari, A. and Ellias, M., Loin pain hematuria syndrome: Pain control with RFA to the Splanchanic plexus, The Pain Clinic, 2000, vol. 12, No. 4, pp. 323-327.
Bhatt, Deepak L. et al., Rhabdomyolysis Due to Pulsed Electric Fields, May 11, 1989, Plastic and Reconstructive Surgery Jul. 1990, pp. 1-11.
Bichet, D., et al., Renal intracortical blood flow and renin secretion after denervation by 6-hydroxydopamine. Can J Physiol Pharmacol. 1982;60:184-92.
Bigler, D. et al., Tachyphylaxis during postoperative epidural analgesia—new insights, Apr. 15, 1987, Letter to the Editor, Acta Anaesthesiol Scand. 1987, vol. 31, pp. 664-665.
Binder, Allan et al., Pulsed Electromagnetic Field Therapy of Persistent Rotator Cuff Tendinitis, The Lancet, Saturday Mar. 31, 1984, The Lancet Ltd., pp. 695-698.
Black, M.D., Henry R., Resistant Hypertension 2004, presentation at Rush University Medical Center, Jul. 15, 2004, 40 pages.
Blad, B., et al., An Electrical Impedance index to Assess Electroporation in Tissue, Tissue and Organ (Therapy), 2001, Oslo, www.bl.uk <http://www.bl.uk> British Library, pp. 31-34.
Blair, M. L. et al, Sympathetic activation cannot fully account for increased plasma renin levels during water deprivation, Sep. 23, 1996, Am. J. Physiol., vol. 272, 1997, the American Physiological Society 1997, pp. R1197-R1203.
Blomberg, S.G., M.D., PhD, Long-Term Home Self-Treatment with High Thoracic Epidural Anesthesia in Patients with Severe Coronary Artery Disease, Mar. 29, 1994, Anesth Analg 1994, vol. 79, 1994 International Anesthesia Research Society, pp. 413-421.
Boehmer, J.P., Resynchronization Therapy for Chronic CHF: Indications, Devices and Outcomes. Penn State College of Medicine: Penn State Heart and Vascular Institute. Transcatheter Cardiovascular Therapeutics 2005, 31 slides.
Bourge, R.C., Heart Failure Monitoring Devices: Rationale and Status 28 pages, Feb. 2001.
Braunwald, E., Heart Disease, A Textbook of Cardiovascular Medicine, 5th Ed., vol. 2, 1997, pp. 480-481, 824-825, 1184-1288 and 1923-1925, W.B. Saunders Company.
Bravo, E.L., et al., Renal denervation for resistant hypertension, American Journal of Kidney Diseases, 2009, 3 pgs.
Bunch, Jared T. et al. Mechanisms of Phrenic Nerve Injury During Radiofrequency Ablation at the Pulmonary Vein Orifice. Journal of Cardiovascular Electrophysiclody. vol. 16, No. 12. pp. 1318-1325. Dec. 2005.
Burkhoff, D., Interventional Device-Based Therapy for CHF Will Redefine Current Treatment Paradigms. Columbia University. 2004. 32 slides.
Burns, J. et al., Relationship between central sympathetic drive and magnetic resonance imaging-determined left ventricular mass in essential hypertension. Circulation. 2007;115:1999-2005.
Cahana, A. et al., Acute Differential Modulation of Synaptic Transmission and Cell Survival During Exposure to Pulsed and Continuous Radiofrequency Energy, May 2003, The Journal of Pain, vol. 4, No. 4, © 2003 by the American Pain Society, pp. 197-202.
Cahana, Alex, M.D., Pulsed Radiofrequency: A Neurobiologic and Clinical Reality, May 17, 2005, Anesthesiology 2005, vol. 103, No. 6, Dec. 2005, 2005 American Society of Anesthesiologists, Inc. Lippincott Williams & Wilkins, Inc., p. 1311.
Calaresu, F.R. et al., Haemodynamic Responses and Renin Release During Stimulation of Afferent Renal Nerves in the Cat, Aug. 12, 1975, J. Physiol. 1976, vol. 255, pp. 687-700.
Cameron, Tracy. Micromodular Implants to Provide Electrical Stimulation of Paralyzed Muscles and Limbs. IEEE Transactions on Biomedical Engineering, vol. 44, No. 9, Sep. 1997. pp. 781-790.
Campese, V.M. et al., Renal afferent denervation prevents hypertension in rats with chronic renal failure. Hypertension. 1995;25:878-82.
Campese, V.M. et al., Renal Afferent Denervation Prevents the Progression of Renal Disease in the Renal Ablation Model of Chronic Renal Failure in the Rat, Am J Kidney Dis. 1995;26:861-5.

Campese, V.M., A new model of neurogenic hypertension caused by renal injury: pathophysiology and therapeutic implications, Clin Exp Nephrol (2003) 7: 167-171, Japanese Society of Nephrology 2003.
Campese, V.M., Neurogenic factors and hypertension in chronic renal failure, Journal of Nephrology, vol. 10, No. 4, 1997, Societa Italiana di Nefrologia, pp. 184-187.
Campese, V.M., Neurogenic factors and hypertension in renal disease. Kidney Int. 2000;57 Suppl 75:S2-3.
Canbaz, S. et al., Electrophysiological evaluation of phrenic nerve injury during cardiac surgery—a prospective, controlled clinical study. BioMed Central. 5 pgs. 2004.
Cardiac Glycosides, Heart Disease—A Textbook of Cardiovascular Medicine vol. 2, Edited by Eugene Braunwald, 5th Edition, 1997 WB Saunders Company, pp. 480-481.
Carls, G. et al., Electrical and magnetic stimulation of the intercostal nerves: a comparative study, Electromyogr, clin. Neurophysiol. 1997, vol. 37, pp. 509-512.
Carlson, Scott H. and J. Michael Wyss, e-Hypertension—Opening New Vistas, Introductory Commentary, Hypertension 2000, vol. 35, American Heart Association, Inc. 2000, p. 538.
Carson, P., Device-based Treatment for Chronic Heart Failure: Electrical Modulation of Myocardial Contractility. Transcatheter Cardiovascular Therapeutics 2005, 21 slides.
Chang, Donald C., Cell poration and cell fusion using an oscillating electric field, Biophysical Journal, vol. 56, Oct. 1989, Biophysical Society, pp. 641-652.
Chen, S.A. et al., Initiation of atrial fibrillation by ectopic beats originating from the pulmonary veins: electrophysiological characteristics, pharmacological responses, and effects of radiofrequency ablataion, Circulation, 1999, 100:1879-1886.
Chin, J.L. et al., Renal autotransplantation for the loin pain-hematuria syndrome: long term follow up of 26 cases, J Urol, 1998, vol. 160, pp. 1232-1236.
Chiou, C.W. et al., Efferent Vagal Innervation of the Canine Atria and Sinus and Atrioventricular Nodes. Circulation. Jun. 1997. 95(11):2573-2584. Abstract only. 2 pgs.
Chobanian, Aram V. et al., Seventh Report of the Joint National Committee on Prevention, Detection, Evaluation, and Treatment of High Blood Pressure, Nov. 6, 2003, Hypertension 2003, vol. 42, 2003 American Heart Association, Inc., pp. 1206-1252.
Clinical Trials in Hypertension and Renal Diseases, Slide Source, www.hypertensiononline.org, 33 pages Aug. 13, 2001.
Conradi, E. and Ines Helen Pages, Effects of Continous and Pulsed Microwave Irradiation on Distribution of Heat in the Gluteal Region of Minipigs, Scand J Rehab Med, vol. 21, 1989, pp. 59-62.
Converse, R.L., Jr. et al., Sympathetic Overactivity in Patients with Chronic Renal Failure, N Engl J Med. Dec. 31, 1992, vol. 327 (27), pp. 1912-1918.
Cosman, E.R., Jr. et al., Electric and Thermal Field Effects in Tissue Around Radiofrequency Electrodes, Pain Medicine, vol. 6, No. 6, 2005, American Academy of Pain Medicine, pp. 405-424.
Cosman, E.R., Ph.D., A Comment on the History of the Pulsed Radiofrequency Technique for Pain Therapy, Anesthesiology Dec. 2005, vol. 103, No. 6, 2005 American Society of Anesthesiologists, Inc. Lippincott Williams & Wilkins, Inc., p. 1312.
Crawford, William H. et al., Pulsed Radio Frequency Therapy of Experimentally Induced Arthritis in Ponies, Dec. 18, 1989, Can. J. Vet. Res. 1991, vol. 55, pp. 76-85.
Curtis, J.J. et al., Surgical therapy for persistent hypertension after renal transplantation, Transplantation, 1981, 31(2):125-128.
Dahm, Peter et al., Efficacy and Technical Complications of Long-Term Continuous Intraspinal Infusions of Opioid and/or Bupivacaine in Refractory Nonmalignant Pain . . . , Oct. 6, 1997, The Clinical Journal of Pain, vol. 14, No. 1, 1998, Lippincott-Raven Publishers 1998, pp. 4-16.
Dahm, Peter O. et al., Long-Term Intrathecal Infusion of Opioid and/or Bupivacaine in the Prophylaxis and Treatment of Phantom Limb Pain, Neuromodulation, vol. 1, No. 3, 1998, International Neuromodulation Society 1998, pp. 111-128.
Dang, Nicholas C. et al., A Novel Approach to Increase Total Urine Output in Heart Failure: Renal Nerve Blockade, ACC 2005 poster; 1 page.

(56) References Cited

OTHER PUBLICATIONS

Daniel, Alan and Honig, Carl R. Does Histamine Influence Vasodilation Caused by Prolonged Arterial Occlusion or Heavy Exercise? The Journal of Pharmacology and Experimental Therapeutics. vol. 215 No. 2. Aug. 21, 1980. pp. 533-538.
Davalos, R. et al., Electrical Impedance Tomography for Imaging Tissue Electroporation, Jul. 25, 2003, IEEE Transactions on Biomedical Engineering, vol. 51, No. 5, May 2004, IEEE 2004, pp. 761-767.
Davalos, R.V. et al., Tissue Ablation with Irreversible Electroporation, Sep. 7, 2004, Annals of Biomedical Engineering, Feb. 2005, vol. 33, No. 2, 2005 Biomedical Engineering Society, pp. 223-231.
De Leeuw, Peter W. et al., Renal Vascular Tachyphylaxis to Angiotensin II: Specificity of the Response for Angiotensin, Dec. 28, 1981, Life Sciences, vol. 30, 1982 Pergamon Press Ltd., pp. 813-819.
Deng, Jingdong et al., The Effects of Intense Submicrosecond Electrical Pulses on Cells, Nov. 26, 2002, Biophysical Journal, vol. 84, Apr. 2003, Biophysical Society 2003, pp. 2709-2714.
Denton, Kate M. et al., Differential Neural Control of Glomerular Ultrafiltration, Jan. 30, 2004, Proceedings of the Australian Physiological and Pharmacological Society Symposium: Hormonal, Metabolic and Neural Control of the Kidney, Clinical and Experimental Pharmacology and Physiology (2004) 31, pp. 380-386.
Dev, Nagendu B., Ph.D. et al., Intravascular Electroporation Markedly Attenuates Neointima Formation After Balloon Injury of the Carotid Artery in the Rat, Journal of Interventional Cardiology, vol. 13, No. 5, 2000, pp. 331-338.
Dev, Nagendu B., Ph.D. et al., Sustained Local Delivery of Heparin to the Rabbit Arterial Wall with an Electroporation Catheter, May 5, 1998, Catheterization and Cardiovascular Diagnosis, vol. 45, 1998, Wiley-Liss, Inc. 1998, pp. 337-345.
Devereaux, R.B. et al., Regression of Hypertensive Left Ventricular Hypertrophy by Losartan Compared With Atenolol: The Losartan Intervention for Endpoint Reduction in Hypertension (LIFE) Trial, Circulation, 2004, vol. 110, pp. 1456-1462.
DiBona, Gerald F. and Linda L. Sawin, Role of renal nerves in sodium retention of cirrhosis and congestive heart failure, Sep. 27, 1990, Am. J. Physiol. 1991, vol. 260, 1991 the American Physiological Society, pp. R298-R305.
DiBona, Gerald F. and Susan Y. Jones, Dynamic Analysis of Renal Nerve Activity Responses to Baroreceptor Denervation in Hypertensive Rats, Sep. 19, 2000, Hypertension Apr. 2001, American Heart Association, Inc. 2001, pp. 1153-1163.
DiBona, Gerald F. and Ulla C. Kopp, Neural Control of Renal Function, Physiological Reviews, vol. 77, No. 1, Jan. 1997, the American Physiological Society 1997, pp. 75-197.
DiBona, Gerald F. and Ulla C. Kopp, Role of the Renal Sympathetic Nerves in Pathophysiological States, Neural Control of Renal Function, vol. 77, pp. 142-197 Jan. 1997.
DiBona, Gerald F., Functionally Specific Renal Sympathetic Nerve Fibers: Role in Cardiovascular Regulation, Mar. 6, 2001, American Journal of Hypertension, 2001, vol. 14, 2001 American Journal of Hypertension, Ltd. Published by Elsevier Science Inc., pp. 163S-170S.
DiBona, Gerald F., L.L. Sawin, Effect of renal nerve stimulation on NaCI and H2O transport in Henle's loop of the rat,: 1982, American Physiological Society, F576-F580, 5 pgs.
DiBona, Gerald F., Nervous Kidney—Interaction Between Renal Sympathetic Nerves and the Renin-Angiotensin System in the Control of Renal Function, Jun. 21, 2000, Hypertension 2000, vol. 36, 2000 American Heart Association, Inc., pp. 1083-1088.
DiBona, Gerald F., Neural Control of the Kidney—Past, Present and Future, Nov. 4, 2002, Novartis Lecture, Hypertension 2003, 41 part 2, 2002 American Heart Association, Inc., pp. 621-624.
DiBona, Gerald F., Neural Control of the Kidney: Functionally Specific Renal Sympathetic Nerve Fibers, Starling Lecture, Am J Physiol Regulatory Integrative Comp Physiol, 2000, 279, 2000 The American Physiological Society, pp. R1517-R1524.
DiBona, Gerald F., Peripheral and Central Interactions between the Renin-Angiotensin System and the Renal Sympathetic Nerves in Control of Renal Function, Annals New York Academy of Sciences, pp. 395-406 Jan. 25, 2006.
DiBona, Gerald F., Renal Innervation and Denervation: Lessons from Renal Transplantation Reconsidered, Artificial Organs, vol. 11, No. 6, Raven Press, Ltd., 1987 International Society for Artificial Organs, pp. 457-462.
DiBona, Gerald F., Sympathetic Nervous System and the Kidney in Hypertension, Current Opinion in Nephrology and Hypertension 2002, vol. 11, 2002 Lippincott Williams & Wilkins, pp. 197-200.
DiBona, Gerald F., The Sympathetic Nervous System and Hypertension, Dec. 4, 2003, Hypertension Highlights, Hypertension Feb. 2004, vol. 43, 2004 American Heart Association, Inc., pp. 147-150.
DiBona, Gerald, LL Sawin, Effect of renal denervation on dynamic autoregulation of renal blood flow, Feb. 12, 2004, AmJ Physiol Renal Physiol 286, pp. F1209-F1218.
Dong, Jun et al. Incidence and Predictors of Pulmonary Vein Stenosis Following Catheter Ablation of Atrial Fibrillation Using the Anatomic Pulmonary Vein Ablation Approach: Results from Paired Magnetic Resonance Imaging. Journal of Cardiovascular Electrophysiology. vol. 16, No. 8, Aug. 2005. pp. 845-852.
Dorros, Gerald, M.D., Renal Artery Stenting State of the Art, presentation, TCT, Washington D.C., Sep. 2003, 27 pages.
Dueck, Ron, M.D., Noninvasive Cardiac Output Monitoring, The Cardiopulmonary and Critical Care Journal, Chest, vol. 120, sec. 2, Aug. 2001, American College of Chest Physicians 2005, pp. 339-341, 5 pages.
Dunn, Matthew D. et al., Laparoscopic Nephrectomy in Patients With End-Stage Renal Disease and Autosomal Dominant Polycystic Kidney Disease,Oct. 25, 1999, American Journal of Kidney Diseases, vol. 35, No. 4 Apr. 2000, National Kidney Foundation, Inc. 2000, pp. 720-725.
Durand, D.M., Electric Field Effects in Hyperexcitable Neural Tissue: A Review, Radiation Protection Dosimetry, vol. 106, No. 4, 2003 Nuclear Technology Publishing, pp. 325-331.
Effects of Renal Failure on the Cardiovascular System, 5th Edition Heart Disease, a Textbook of Cardiovascular Medicine, vol. 2, Edited by Eugene Braunwald, 1997, W.B. Saunders Company, pp. 1923-1925.
Electrical Stimulation for the Treatment of Chronic Wounds, Radiation Protection Standard, Maximum Exposure Levels to Radiofrequency Fields—3 KHz to 300 GHz, Radiation Protection Series No. 3, Australian Radiation Protection and Nuclear Safety Agency, Apr. 1996, 322 pgs.
Electropermeabilization (Electroporation), Cyto Pulse Sciences, Inc., http://www.cytopulse.com/electroporation.html (last accessed Mar. 3, 2005), 3 pgs.
Electroporation based Technologies and Treatments, ESPE Newsletter No. 6, QLK 02002-2003, Jan. 2005, www.cliniporator.com, 4 pgs.
End-stage renal disease payment policies in traditional Medicare, Chapter 8, Report to the Congress: Medicare Payment Policy, Mar. 2001, Medpac, pp. 123-138.
Epidemiology of Renal Disease in Hypertension, slide presentation by hypertensiononline.org, 21 pages Mar. 30, 2001.
Erdine, Serap and Alev ARAT-OZKAN, Resistant Hypertension, European Society of Hypertension Scientific Newsletter: Update on Hypertension Management 2003, vol. 4, No. 15, 2 pages.
Esler, M. et al., Mechanism of elevated plasma noradrenaline in the course of essential hypertension. J Cardiovasc Pharmacol. 1986;8:S39-43.
Esler, M. et al., Noradrenaline release and the pathophysiology of primary human hypertension. Am J Hypertens. 1989; 2:140S-146S.
Esler, M. et al., Sympathetic nerve biology in essential hypertension, Clin and Exp Pharmacology and Physiology, 2001, 28:986-989.
European Examination Report; European Patent Application No. 07799148.7; Applicant: Ardian, Inc.; dated Jan. 19, 2010, 4 pgs.
European Examination Report; European Patent Application No. 09156661.2; Applicant: Ardian, Inc.; dated Jan. 19, 2010, 6 pgs.
European Search Report; European Patent Application No. 05806045.0; Applicant: Ardian, Inc.; dated Sep. 22, 2009, 8 pgs.

(56) References Cited

OTHER PUBLICATIONS

European Search Report; European Patent Application No. 05811851.4; Applicant: Ardian, Inc.; dated Oct. 1, 2009, 7 pgs.
European Search Report; European Patent Application No. 06847926.0; Applicant: Ardian, Inc.; dated Feb. 10, 2010, 6 pgs.
European Search Report; European Patent Application No. 07757925.8; Applicant: Ardian, Inc.; dated Apr. 29, 2010, 9 pgs.
European Search Report; European Patent Application No. 07798341.9; Applicant: Ardian, Inc.; dated Aug. 4, 2011; 6 pgs.
European Search Report; European Patent Application No. 07799148.7; Applicant: Ardian, Inc.; dated Jul. 23, 2009, 6 pgs.
European Search Report; European Patent Application No. 07868755.5; Applicant: Ardian, Inc.; dated Jul. 28, 2010, 7 pgs.
European Search Report; European Patent Application No. 09156661.2; Applicant: Ardian, Inc.; dated Jul. 23, 2009, 6 pgs.
European Search Report; European Patent Application No. 09167937.3; Applicant: Ardian, Inc.; dated Nov. 11, 2009, 6 pgs.
European Search Report; European Patent Application No. 09168202.1; Applicant: Ardian, Inc.; dated Nov. 11, 2009, 5 pgs.
European Search Report; European Patent Application No. 09168204.7; Applicant: Ardian, Inc.; dated Nov. 19, 2009, 6 pgs.
Evelyn, K.A. et al., Effect of thoracolumbar sympathectomy on the clinical course of primary (essential) hypertension, Am J Med, 1960;28:188-221.
Ex parte Quayle Office Action; U.S. Appl. No. 11/144,173, dated May 28, 2009, 4 pgs.
Fact Book Fiscal Year 2003, National Institutes of Health National Heart, Lung, and Blood Institute, Feb. 2004, 197 pgs.
Fajardo, J. et al., Effect of chemical sympathectomy on renal hydroelectrolytic handling in dogs with chronic caval constriction. Clin Physiol Biochem. 1986;4:252-6.
Fareed, Jawed, Ph.D. et al., Some Objective Considerations for the Use of Heparins and Recombinant Hirudin in Percutaneous Transluminal Coronary Angoplasty, Seminars in Thrombosis and Hemostasis 1991, vol. 17, No. 4, 1991 by Thieme Medical Publishers, Inc., pp. 455-470.
Ferguson, D.R. et al., Responses of the pig isolated renal artery to transmural electrical stimulation and drugs, Dec. 7, 1984, Br. J. Pharmac. 1985, vol. 84, The Macmillan Press Ltd. 1985, pp. 879-882.
Fernandez-Ortiz, Antonio, et al., A New Approach for Local Intravascular Drug Delivery—Iontophoretic Balloon, Intravascular Iontophoretic Local Delivery, Circulation, vol. 89, No. 4, Apr. 1994, pp. 1518-1522.
Fields, Larry E. et al., The Burden of Adult Hypertension in the United States 1999 to 2000—A Rising Tide, May 18, 2004, American Heart Association 2004, Hypertension Oct. 2004, pp. 1-7.
Final Office Action; U.S. Appl. No. 11/233,814; dated Jan. 29, 2009, 11 pgs.
Final Office Action; U.S. Appl. No. 11/266,993; dated Jan. 8, 2010, 7 pgs.
Final Office Action; U.S. Appl. No. 11/363,867; dated May 1, 2009, 8 pgs.
Final Office Action; U.S. Appl. No. 11/451,728; dated Jan. 13, 2009, 7 pgs.
Final Office Action; U.S. Appl. No. 11/599,649; dated Jan. 15, 2009, 10 pgs.
Final Office Action; U.S. Appl. No. 11/599,723; dated Apr. 5, 2010, 17 pgs.
Final Office Action; U.S. Appl. No. 11/599,890; dated Apr. 29, 2009, 9 pgs.
Fischell, Tim A. et al., Ultrasonic Energy: Effects on Vascular Function and Integrity, Circulation: Journal of the American Heart Association. 1991. 84;pp. 1783-1795.
Freeman, Scott A. et al., Theory of Electroporation of Planar Bilayer Membranes: Predictions of the Aqueous Area, Change in Capacitance, and Pore-Pore Separation, Feb. 23, 1994, Biophysical Journal, Jul. 1994, vol. 67, 1994 by the Biophysical Society, pp. 42-56.

Fukuoka, Yuko et al., Imaging of neural conduction block by neuromagnetic recording, Oct. 16, 2002, Clinical Neurophysiology, vol. 113, 2002, Elsevier Science Ireland Ltd. 2002, pp. 1985-1992.
Fuster, Valentin et al. ACC/AHA/ESC Practice Guidelines: ACA/AHA/ESC 2006 Guidelines for the Management of Patients with Atrial Fibrillation. JACC vol. 48, No. 4, Aug. 15, 2006.
Gami, Apoor S., M.D. and Vesna D. Garovic, M.D., Contrast Nephropathy After Coronary Angiography, Mayo Clin Proc. 2004, vol. 79, 2004 Mayo Foundation for Medical Education and Research, pp. 211-219.
Gattone II, Vincent H. et al., Contribution of Renal Innervation to Hypertension in Polycystic Kidney Disease in the Rat, University of Chicago Section of Urology, 16 pages, Mar. 17, 2008.
Gaylor, D.C. et al., Significance of Cell Size and Tissue Structure in Electrical Trauma, Jan. 26, 1988, J. theor. Biol. 1988, vol. 133, 1988 Academic Press Limited, pp. 223-237.
Gazdar, A.F. and G.J. Dammin, Neural degeneration and regeneration in human renal transplants, NEJM, Jul. 30, 1970, 283:222-244.
Gehl, Julie et al., In Vivo Electroporation of Skeletal Muscle: Threshold, Efficacy and Relation to Electric Field Distribution, Biochimica et Biophysica Acta, 1428, 1999, Elsevier Science B.V. 1999, pp. 233-240, www.elsevier.com/locate/bba <http:www.elsevier.com/locate/bba>.
Getts, R.T. al., Regression of left ventricular hypertrophy after bilateral nephrectomy, Nephrol Dial Transplant, 2006, vol. 21, pp. 1089-1091.
Ghoname, El-sayed A. et al., Percutaneous electrical nerve stimulation: an alternative to Tens in the management of sciatica, Apr. 26, 1999, Pain 1999, vol. 83, 1999 International Association for the Study of Pain / Published by Elsevier Science B.V., pp. 193-199.
Gimple, M.D., Lawrence et al., Effect of Chronic Subcutaneous or Intramural Administration of Heparin on Femoral Artery Restenosis After Balloon Angioplasty in Hypercholesterolemic Rabbits, Laboratory Investigation, Circulation, vol. 86, No. 5, Nov. 1992, pp. 1536-1546.
Goldberger, Jeffrey J. et al., New technique for vagal nerve stimulation, Jun. 2, 1999, Journal of Neuroscience Methods 91, 1999, Elsevier Science B.V. 1999, pp. 109-114.
Gorbunov, F.E. et al., The Use of Pulsed and Continuous Short Wave Diathermy (Electric Field) in Medical Rehabilitation of the Patients with Guillan-Barre Syndrome and Other Peripheral Myelinopathies, May 6, 1994, 5 pages (most of article in Russian language).
Gottschalk, C.W., Renal nerves and sodium excretion, Ann. Rev. Physiol., 1979, 41:229-240.
Greenwell, T.J. et al., The outcome of renal denervation for managing loin pain haematuria syndrome. BJU International, 2004; 4 pgs.
Gruberg, Luis, M.D. et al., The Prognostic Implications of Further Renal Function Deterioration Within 48 h of Interventional Coronary Procedures in Patients with Pre-existent Chronic Renal Insufficiency, Jun. 19, 2000, Journal of the American College of Cardiology 2000, vol. 36, No. 5, 2000 by the American College of Cardiology, pp. 1542-1548.
Guimaraes, Sarfim. Vascular Adrenoceptors: An Update. pp. 319-356, Jun. 1, 2001.
Haissaguerre, M. et al., Spontaneous initiation of atrial fibrillation by ectopic beats orginating in the pulmonary veins, New England Journal of Medicine, 1998, 339: 659-666.
Hajjar, Ihab, M.D., M.S. and Theodore A. Kotchen, M.D., Trends in Prevalence, Awareness, Treatment, and Control of Hypertension in the United States, 1988-2000, JAMA, Jul. 9, 2003, vol. 290, No. 2, pp. 199-206.
Hammer, Leah W. Differential Inhibition of Functional Dilation of Small Arterioles by Indomethacin and Glibenclamide. Hypertension. Feb. 2001 Part II. pp. 599-603.
Hampers, C.L. et al., A hemodynamic evaluation of bilateral nephrectomy and hemodialysis in hypertensive man, Circulation. 1967;35:272-288.
Hamza, M.D., Mohamed A. et al., Effect of the Duration of Electrical Stimulation on the Analgesic Response in Patients with Low Back Pain, Anesthesiology, vol. 91, No. 6, Dec. 1999, American Society of Anesthesiologists, Inc. 1999, pp. 1622-1627.

(56) References Cited

OTHER PUBLICATIONS

Han, Hyo-Kyung and Gordon L. Amidon, Targeted Prodrug Design to Optimize Drug Delivery, Mar. 21, 2000, AAPS Pharmsci 2000, 2 (1) article 6, pp. 1-11.
Hansen, J.M. et al., The transplanted human kidney does not achieve functional reinnervation, Clin Science, 1994, vol. 87, pp. 13-20.
Hasking, G.J. et al., Norepinephrine spillover to plasma in patients with congestive heart failure: evidence of increased overall and cardiorenal sympathetic nervous activity. Circulation. 1986;73:615-21.
Hausberg, M. et al., Sympathetic nerve activity in end-stage renal disease, Circulation, 2002, 106: 1974-1979.
Heart Arrhythmia Heart and Vascular Health on Yahoo! Health. 13 pgs. <URL: http://health.yahoo.com/topic/heart/overview/article/mayoclinic/21BBE2B0-128D-4AA2-A5CE215065586678;_ylt=Aqd9M5rNyHD0sbPOmHXFhLcPu7cF> Feb. 16, 2005.
Heart Disease and Stroke Statistics—2004 Update, American Heart Association, American Stroke Association, Dallas, Texas, 2003 American Heart Association, 52 pgs.
Heida, Tjitske, et al., Investigating Membrane Breakdown of Neuronal Cells Exposed to Nonuniform Electric Fields by Finite-Element Modeling and Experiments, May 9, 2002, IEEE Transactions on Biomedical Engineering, vol. 49, No. 10, Oct. 2002, IEEE 2002, pp. 1195-1203.
Heuer, G.J., The surgical treatment of essential hypertension, Annals of Surgery, 1936; 104 (4): 771-786.
Higuchi, Yoshinori, M.D., Ph.D. et al, Exposure of the Dorsal Root Ganglion in Rats to Pulsed Radiofrequency Currents Activates Dorsal Horn Lamina I and II Neurons, Dec. 4, 2001, Experimental Studies, Neurosurgery, vol. 50, No. 4, Apr. 2002, pp. 850-856.
Hildebrand, Keith R., D.V.M., Ph.D. et al., Stability, Compatibility, and Safety of Intrathecal Bupivacaine Administered Chronically via an Implantable Delivery System, May 18, 2001, The Clinical Journal of Pain, vol. 17, No. 3, 2001 Lippincott Williams & Wilkins, Inc., pp. 239-244.
Hing, Esther, M.P.H. and Kimberly Middleton, B.S.N., M.P.H., National Hospital Ambulatory Medical Care Survey: 2001 Outpatient Department Summary, Aug. 5, 2003, Advance Data from Vital and Health Statistics, No. 338, CDC, 32 pages.
Hodgkin, Douglas D. et al., Electrophysiologic Characteristics of a Pulsed Iontophoretic Drug-Delivery System in Coronary Arteries, Journal of Cardiovascular Pharmacology. 29(1):pp. 39-44, Jan. 1997, Abstract, 2 pgs.
Hopp, F.A. et al., Respiratory Responses to Selective Blockade of Carotid Sinus Baroreceptors in the Dog, Jun. 22, 2005, Am J Physiol Regul Integr Comp Physiol 1998, vol. 275, 2005 American Physiological Society, pp. R10-R18.
Hortobagyi, Gabriel N., Randomized Trial of High-Dose Chemotherapy and Blood Cell Autographs for High-Risk Primary Breast Carcinoma, Journal of the National Cancer Institute, vol. 92, No. 3, Feb. 2, 2000, pp. 225-233.
Horwich, Tamara, M.D., New Advances in the Diagnosis and Management of Acute Decompensated Heart Failure, the heart.org satellite program, Rapid Review, CME Symposium presented on Nov. 8, 2004 at the Sheraton New Orleans Hotel, 4 pages.
Huang, Wann-Chu et al. Renal Denervation Prevents and Reverses Hyperinsulinemia-Induced Hypertension in Rats, Mar. 25, 1998, Hypertension 1998, vol. 32, 1998 American Heart Association, pp. 249-254.
Huang, Yifei et al., Remodeling of the chronic severely failing ischemic sheep heart after coronary microembolization: functional, energetic, structural and cellular responses, Jan. 8, 2004, Am J Physiol. Heart Circ. Physiol. 2004, vol. 286, 2004 the American Physiological Society, pp. H2141-H2150.
Hughes, Gordon B., M.D. et al., A Comparative Study of Neuropathologic Changes Following Pulsed and Direct Current Stimulation of the Mouse Sciatic Nerve, Jun. 27, 1980, American Journal of Otolaryngology, Nov. 1980, vol. 1, No. 5, pp. 378-384.
Hypertension and Renal Disease: Mechanisms, Slide Show by www.hypertensiononline.org, 22 pages Mar. 30, 2001.
Hypertension Incidence and Prevalence, Age-Specific Rates, by Gender, B.C., 2001/2002, Graph, Chronic Disease Management, May 2003, British Columbia Ministry of Health Services, 1 page.
Implantable Neurostimulation Systems, Medtronic Neurological, http://medtronic.com/neuro/paintherapies/pain_treatment_ladder/pdf/implantable_brochure.pdf; 1999, 6 pages.
Implantable Pump—The Medtronic MiniMed 2007 Implantable Insulin Pump System, Medtronic MiniMed, 2006, 5 pgs.
International Search Report and Written Opinion for PCT/US2009/069334; Applicant: Ardian, Inc.; dated Mar. 1, 2010, 10 pgs.
International Search Report and Written Opinion, PCT/US05/35693, dated Mar. 8, 2006, Applicant: Ardian, Inc., 29 pgs.
International Search Report and Written Opinion, PCT/US05/35757, dated Dec. 27, 2006, Applicant: Ardian, Inc., 8 pgs.
International Search Report and Written Opinion, PCT/US06/36120, dated Jun. 25, 2008, Applicant: Ardian, Inc., 10 pgs.
International Search Report and Written Opinion, PCT/US06/41889, dated Oct. 20, 2008, Applicant: Ardian, Inc., 7 pgs.
International Search Report and Written Opinion, PCT/US06/48822, dated Aug. 15, 2008, Applicant: Ardian, Inc., 12 pgs.
International Search Report and Written Opinion, PCT/US07/63322, dated Mar. 3, 2008, Applicant: Ardian, Inc., 10 pgs.
International Search Report and Written Opinion, PCT/US07/63324, dated Oct. 10, 2008, Applicant: Ardian, Inc., 10 pgs.
International Search Report and Written Opinion, PCT/US07/66539, dated Jan. 28, 2008, Applicant: Ardian, Inc., 6 pgs.
International Search Report and Written Opinion, PCT/US07/70799, dated Jul. 2, 2008, Applicant: Ardian, Inc., 7 pgs.
International Search Report and Written Opinion, PCT/US07/72396, dated Aug. 27, 2008, Applicant: Ardian, Inc., 9 pgs.
International Search Report and Written Opinion, PCT/US07/84701, dated Aug. 21, 2008, Applicant: Ardian, Inc., 11 pgs.
International Search Report and Written Opinion, PCT/US07/84705, dated Jul. 28, 2008, Applicant: Ardian, Inc., 12 pgs.
International Search Report and Written Opinion, PCT/US07/84708, dated Aug. 11, 2008, Applicant: Ardian, Inc., 9 pgs.
International Search Report, PCT/US02/0039, dated Sep. 11, 2002, Applicant: Advanced Neuromodulation Systems, Inc.
International Search Report, PCT/US02/25712, dated Apr. 23, 2003, Applicant: Cyberonics, Inc.
International Search Report, PCT/US03/08014, dated Sep. 23, 2003, Applicant: The General Hospital Corporation.
International Search Report, PCT/US03/09764, dated Oct. 28, 2003, Applicant: CVRX, Inc.
International Search Report, PCT/US04/38498, dated Feb. 18, 2005, Applicant: G & L Consulting, LLC, 4 pgs.
Introduction to Autonomic Pharmacology, Chapter 3, Part 2 Autonomic Pharmacology, pp. 18-26, May 24, 2002.
Isovue: Data Sheet. Regional Health Limited. 8 pgs. Mar. 11, 2003.
Israili, Z.H., Clinical pharmacokinetics of angiotensin II (AT) receptor blockers in hypertension, Journal of Human Hypertension, 2000, Macmillan Publishers Ltd., vol. 14, pp. S73-S86.
Janda, J., Impact of the electrical stimulation apparatus rebox on the course of ischemic renal damage in rats, British Library—The world's knowledge pp. 252-254 (translated and untranslated versions) 1996.
Janssen, Ben J.A. et al., Effects of complete renal denervation and selective afferent renal denervation on the hypertension induced by intrarenal norepinephrine infusion in conscious rats, Jan. 4, 1989, Journal of Hypertension 1989, vol. 7, No. 6, Current Science Ltd, pp. 447-455.
Jia, Jianping et al., Cold injury to nerves is not due to ischaemia alone, Brain. 121;pp. 989-1001. 1998.
Jia Jianping et al.., The pathogenesis of non-freezing cold nerve injury: Observations in the rat, Brain. 120; pp. 631-646. 1997.
Jin, Yuanzhe et al., Pulmonary Vein Stenosis and Remodeling After Electrical Isolation for Treatment of Atrial Fibrillation: Short- and Medium-Term Follow-Up, PACE, vol. 27., Oct. 2004, pp. 1362-1370.
Johansson, Bjorn, Electrical Membrane Breakdown, a Possible Mediator of the Actions of Electroconvulsive Therapy, Medical Hypotheses 1987, vol. 24, Longman Group UK Ltd 1987, pp. 313-324.

(56) References Cited

OTHER PUBLICATIONS

Joles J.A. et al., Causes and Consequences of Increased Sympathetic Activity in Renal Disease. Hypertension. 2004;43:699-706.
Jorgensen, William A. et al., Electrochemical Therapy of Pelvic Pain: Effects of Pulsed Electromagnetic Fields (PEMF) on Tissue Trauma, Eur J Surg 1994, Suppl 574, vol. 160, 1994 Scandinavian University Press, pp. 83-86.
Joshi, R. P. and K. H. Schoenbach, Mechanism for membrane electroporation irreversibility under high-intensity, ultrashort electrical pulse conditions, Nov. 11, 2002, Physical Review E 66, 2002, The American Physical Society 2002, pp. 052901-1-052901-4.
Joshi, R. P. et al., Improved energy model for membrane electroporation in biological cells subjected to electrical pulses, Apr. 9, 2002, Physical Review E, vol. 65, 041920-1, 2002 The American Physical Society, 8 pages.
Joshi, R. P. et al., Self-consistent simulations of electroporation dynamics in biological cells subjected to ultrashort electrical pulses, Jun. 21, 2001, Physical Review E, vol. 64, 011913, 2001 The American Physcial Society, pp. 1-10.
Kanduser, Masa et al., Effect of surfactant polyoxyethylene glycol (C12E8) on electroporation of cell line DC3F, Aug. 20, 2002, Colloids and Surfaces A: Physicochem. Eng. Aspects 214, 2003, Elsevier Science B.V. 2002, pp. 205-217.
Kassab, S. et al., Renal denervation attenuates the sodium retention and hypertension associated with obesity, Hypertension, 1995, 25:893-897.
Katholi, R.E. et al., Importance of the renal nerves in established two-kidney, one clip Goldblatt hypertension, Hypertension, 1982, 4 (suppl II): II-166-II-174.
Katholi, R.E. et al., Role of the renal nerves in the pathogenesis of one-kidney renal hypertension in the rat, Hypertension, 1981, 3(4) 404-409.
Katholi, R.E., Renal nerves and hypertension: an update, Fed Proc., 1985, 44:2846-2850.
Katholi, Richard E., Renal nerves in the pathogenesis of hypertension in experimental animals and humans, Am. J. Physiol. vol. 245, 1983, the American Physiological Society 1983, pp. F1-F144.
Kaye, D.M. et al., Functional and neurochemical evidence for partial cardiac sympathetic reinnervation after cardiac transplantation in humans, Circulation, 1993, vol. 88, pp. 1101-1109.
Kelleher, Catherine L. et al., Characteristics of Hypertension in Young Adults with Autosomal Dominant Polycystic Kidney Disease Compared with the General U.S. Population, Jun. 9, 2004, American Journal of Hypertension 2004, pp. 1029-1034.
King, Ronald W. P., Nerves in a Human Body Exposed to Low-Frequency Electromagnetic Fields, Jun. 7, 1999, IEEE Transactions on Biomedical Engineering, vol. 46, No. 12, Dec. 1999, IEEE 1999, pp. 1426-1431.
Kinney, Brian M., M.D., High-Tech Healing—The evolution of therapeutic electromagnetic fields in plastic surgery, Plastic Surgery Products, Jun. 2004, pp. 32-36, 3 pages.
Kirchheim, H. et al., Sympathetic modulation of renal hemodynamics, renin release and sodium excretion, Klin Wochenschr, 1989, 67:858-864.
Klein, K. et al., Impaired autofeedback regulation of hypothalamic norepinephrine release in experimental uremia. J Am Soc Nephrol. 2005;16:2081-7.
Knot, H. J. et al., Regulation of arterial diameter and wall [Ca2+] in cerebral arteries of rat by membrane potential and intravascular pressure. The Journal of Physiology. 1998. 508; pp. 199-209.
Kok, Lai Chow et al. Effect of Heating on Pulmonary Veins: How to Avoid Pulmonary Vein Stenosis. Journal of Cardiovascular Electrophysiology. vol. 14, No. 3, Mar. 2003. pp. 250-254.
Kok, R. J. et al., Specific Delivery of Captopril to the Kidney with the Prodrug Captopril-Lysozyme, Aug. 16, 1998, Journal of Pharmacology and Experimental Therapeutics, vol. 288, No. 1, 1999 by The American Society for Pharmacology and Experimental Therapeutics, pp. 281-285.
Kon, V. Neural Control of Renal Circulation, Miner Electrolyte Metab. 1989;15:33-43.
Koomans, H.A., et al., Sympathetic hyperactivity in chronic renal failure: a wake-up call. J Am Soc Nephrol. 2004;15:524-37.
Kopp, U. et al., Dietary sodium loading increases arterial pressure in afferent renal-denervated rats, Hypertension, 2003, 42:968-973.
Kopp, U.C. et al., Renal sympathetic nerve activity modulates afferent renal nerve activity by PGE2-dependent activation of alpha1- and alpha2—adrenoceptors on renal sensory nerve fibers. Am J Physiol Regul Integr Comp Physiol. 2007;293:R1561-72.
Koyama, Shozo et al., Relative Contribution of Renal Nerve and Adrenal Gland to Renal Vascular Tone During Prolonged Canine Hemorrhagic Hypotension, Sep. 24, 1992, Circulatory Shock 1993, vol. 39, Wiley-Liss, Inc. 1993, pp. 269-274.
Kozak, Lola Jean, Ph.D et al., National Hospital Discharge Survey: 2001 Annual Summary with Detailed Diagnosis and Procedure Data, Vital and Health Statistics, Serices 13 No. 156, Jun. 2004, CDC, 206 pages.
Kumagai, K. et al. New Approach to Pulmonary Vein Isolation for Atrial Fibrillation Using a Multielectrode Basket Catheter. Circulation Journal. 2006;70:88-93.
Lafayette, Richard A., M.D., How Does Knocking Out Angiotensin II Activity Reduce Renal Injury in Mice?, Jun. 14, 1999, Journal Club, American Journal of Kidney Diseases, vol. 35, No. 1, Jan. 2000, National Kidney Foundation, Inc. 2000, pp. 166-172.
Lavie, Peretz, Ph.D. and Victor Hoffstein, M.D., Sleep Apnea Syndrome: A Possible Contributing Factor to Resistant Hypertension, Jun. 2001, Sleep 2001, vol. 24, No. 6, pp. 721-725.
Le Noble, J.L. et al., Pharmacological evidence for rapid destruction of efferent renal nerves in rats by intrarenal infusion of 6-hydroxydopamine. J Hypertens Suppl. 1985;3:S137-40.
Lee, Michael A. (editor). SportsMed. Connecticut State Medical Society Committee on the Medical Aspects of Sports. Fall/Winter 2005. 10 pgs.
Lee Raphael C. et al., Biophysical Injury Mechanisms in Electronic Shock Trauma, Annu. Rev. Biomed. Eng., 2000, vol. 2, Copyright © 2000 by Annual Reviews, pp. 477-509.
Lee, Raphael C. et al., Clinical Sequelae Manifested in Electrical Shock Survivors, Presentation by the Electrical Trauma Research Program, The University of Chicago, 37 pages Dec. 24, 2004.
Lee Raphael C. et al., Membrane Biology and Biophysics, Chapter 25, Surgical Research, 2001 Academic Press, pp. 297-305.
Lee, Raphael C., M.D., Sc.D. and Michael S. Kolodney, S.B., Electrical Injury Mechanisms: Electrical Breakdown of Cell Membranes, Oct. 1, 1986, Plastic and Reconstructive Surgery, Nov. 1987, vol. 80, No. 5, pp. 672-679.
Lenoble, L.M. et al., Selective efferent chemical sympathectomy of rat kidneys. Am J Physiol. 1985;249:R496-501.
Ligtenberg, Gerry M.D. et al., Reduction of Sympathetic Hyperactivity by Enalapril in Patients with Chronic Renal Failure, Apr. 29, 1999, New England Journal of Medicine 1999, vol. 340, No. 17, 1999 Massachusetts Medical Society, pp. 1321-1328.
Lin, Vernon W. H. et al., High intensity magnetic stimulation over the lumbosacral spine evokes antinociception in rats, Apr. 16, 2002, Clinical Neurophysiology, vol. 113, 2002 Elsevier Science Ireland Ltd., pp. 1006-1012.
Lipfert, Peter, M.D. et al., Tachyphylaxis to Local Anesthetics Does Not Result form Reduced Drug Effectiveness at the Nerve Itself, Aug. 3, 1988, Anesthesiology 1989, vol. 70, pp. 71-75.
Lohmeier, Thomas E. and Drew A. Hildebrandt, Renal Nerves Promote Sodium Excretion in Angiotensin-Induced Hypertension, Oct. 20, 1997, Hypertension 1998, vol. 31, part 2, 1998 American Heart Association, Inc., pp. 429-434.
Lohmeier, Thomas E. et al., Prolonged Activation of the Baroreflex Produces Sustained Hypotension, Harry Goldblatt Award, Nov. 26, 2003, Hypertension 2004, vol. 43, Part 2, 2004 American Heart Association, Inc., pp. 306-311.
Lohmeier, Thomas E. et al., Renal Nerves Promote Sodium Excretion During Long-Term Increases in Salt Intake, Oct. 23, 1998, Hypertension 1999, vol. 33, part II, 1999 American Heart Association, Inc., pp. 487-492.
Lohmeier, Thomas E. et al., Sustained influence of the renal nerves to attenuate sodium retention in angiotensin hypertension, Apr. 13, 2001, Am J Physiol Regulatory Integrative Comp Physiol, vol. 281, 2001 the American Physiological Society, pp. R434-R443.

(56) References Cited

OTHER PUBLICATIONS

Lohmeier, Thomas E., et al., Baroreflexes prevent neurally induced sodium retention in angiotensin hypertension, American Journal Physiol Regulatory Integrative Comp Physiol, vol. 279, 2000 the American Physiological Society, pp. R1437-R1448.
Lohmeier, Thomas E., Interactions Between Angiotensin II and Baroreflexes in Long-Term Regulation of Renal Sympathetic Nerve Activity, Circulation Research, Jun. 27, 2003, American Heart Association, Inc.2003, pp. 1282-1284.
Luff, S.E. et al., Two types of sympathetic axon innervating the juxtaglomerular arterioles of the rabbit and rat kidney differ structurally from those supplying other arteries, May 1, 1991, Journal of Neurocytology 1991, vol. 20, 1991 Chapman and Hall Ltd., pp. 781-795.
Luippold, G. et al., Chronic renal denervation prevents glomerular hyperfiltration in diabetic rats, Nephrol Dial Transplant (2004) 19:342-347.
Lundborg, C. et al., Clinical experience using intrathecal (IT) bupivacaine infusion in three patients with complex regional pain syndrome type I (CRPS-I), Acta Anaesthesiol Scand 1999, vol. 43, pp. 667-678.
Maeder, Micha, M.D. et al., Contrast Nephropathy: Review Focusing on Prevention, Jun. 22, 2004, Journal of the American College of Cardiology Nov. 2, 2004, vol. 44, No. 9, 2004 by the American College of Cardiology Foundation, pp. 1763-1771.
Malpas, Simon C., What sets the long-term level of sympathetic nerve activity: is there a role for arterial baroreceptors?, Invited Review, Am J Physiol Regul Integr Comp Physiol 2004, vol. 286, 2004 the American Physiological Society, pp. R1-R12.
Mancia, G., Grassi, G., Giannattasio, C., Seravalle, G., Sympathetic actrivation of pathogenesis of hypertension and progression of organ damage, Hypertension 1999, 34 (4 Pt 2): 724-728.
Marenzi, Giancarlo, M.D. et al., The Prevention of Radiocontrast-Agent-Induced Nephropathy by Hemofiltration, New England Journal of Medicine, Oct. 2, 2003, vol. 349 (14), 2003 Massachusetts Medical Society, pp. 1333-1340.
Market for infusion pumps grows with an aging population, NWL 97-01, The BBI Newsletter, vol. 20, No. 2, Feb. 1, 1997, American Health Consultants, Inc., pp. 6.
Martin, Jason B. et al., Gene Transfer to Intact Mesenteric Arteries by Electroporation, Mar. 27, 2000, Journal of Vascular Research 2000, vol. 37, 2000 S. Karger AG, Basel, pp. 372-380.
McCreery, Douglas B. et al., Charge Density and Charge Per Phase as Cofactors in Neural Injury Induced by Electrical Stimulation, IEEE Transactions on Biomedical Engineering, vol. 17, No. 10, Oct. 1990, pp. 996-1000.
McCullough, Peter A., M.D., Mph et al., Acute Renal Failure after Coronary Intervention: Incidence, Risk Factors and Relationship to Mortality, Apr. 14, 1997, Am J Med. 1997, vol. 103, 1997 Excerpta Medica, Inc., pp. 368-375.
McMurray, John J.V., M.D. and Eileen O'Meara, M.D., Treatment of Heart Failure with Spironolactone—Trial and Tribulations, Aug. 5, 2004, New England Journal of Medicine, vol. 351, No. 6, 2004 Massachusetts Medical Society, pp. 526-528.
McRobbie, D. and M.A. Foster, Thresholds for biological effects of time-varying magnetic fields, Dec. 16, 1983, Clin. Phys. Physiol. Meas. 1984, vol. 5, No. 2, 1984 The Institute of Physics, pp. 67-78.
Medtronic Neurostimulation Systems, Expanding the Array of Pain Control Solutions, informational pamphlet, 1999 Medtronic, Inc., 6 pages.
Medtronic, Spinal Cord Stimulation, Patient Management Guidelines for Clinicians, Medtronic, Inc. 1999, 115 pages.
Medtronic, SynchroMed Infusion System—Clinical Reference Guide for Pain Therapy, Medtronic, Inc. 1998, 198 pages.
Mehran, Roxana, Renal insufficiency and contrast nephropathy: The most common, least understood risk factor, Cardiovascular Research Foundation, Columbia University Medical Center, 2005, 86 slides.
Mess, Sarah A., M.D. et al., Implantable Baclofen Pump as an Adjuvant in Treatment of Pressure Sores, Mar. 1, 2003, Annals of Plastic Surgery, vol. 51, No. 5, Nov. 2003, Lippincott Williams & Wilkins 2003, pp. 465-467.
Micro ETS Hyperhidrosis USA Hyperhidrosis USA. 2 pgs. <URL: http://www.hyperhidrosis-usa.com/Index.html>. Nov. 6, 2006.
Mihran, Richard T. et al., Temporally-Specific Modification of Myelinated Axon Excitability in Vitro Following a Single Ultrasound Pulse, Sep. 25, 1989, Ultrasound in Med. & Biol. 1990, vol. 16, No. 3, pp. 297-309.
Miklavčič, D. et al, A Validated Model of in Vivo Electric Field Distribution in Tissues for Electrochemotherapy and for DNA Electrotransfer for Gene Therapy, Biochimica et Biophysica Acta, 1523, 2000, pp. 73-83, <http:www.elsevier.com/locate/bba>.
Mitchell, G. A. G., The Nerve Supply of the Kidneys, Aug. 20, 1949, Acta Anatomica, vol. X, Fasc. ½, 1950, pp. 1-37.
Morrisey, D.M. et al., Sympathectomy in the treatment of hypertension: Review of 122 cases, Lancet. 1953;1:403-408.
Moss, Nicholas G., Renal function and renal afferent and efferent nerve activity, Am. J. Physiol. 1982, vol. 243, 1982 the American Physiological Society, pp. F425-F433.
Munglani, Rajesh, The longer term effect of pulsed radiofrequency for neuropathic pain, Jun. 8, 1998, Pain 80, 1999, International Association for the Study of Pain 1999, Published by Elsevier Science B.V., pp. 437-439.
Naropin (ropivacaine HCl) Injection, RX only Description, AstraZeneca 2001, 3 pages.
National High Blood Pressure Education Program, 1995 Update of the Working Group Reports on Chronic Renal Failure and Renovascular Hypertension, presentation, 13 pages.
National Kidney Foundation, Are You At Increased Risk for Chronic Kidney Disease?, 2002 National Kidney Foundation, Inc., 14 pages.
Nelson, L. et al., Neurogenic Control of Renal Function in Response to Graded Nonhypotensive Hemorrahage in Conscious Dogs, Sep. 13, 1992, Am J. Physiol. 264, 1993, American Physiological Society 1993, pp. R661-R667.
Nikolsky, Eugenia, M.D. et al., Radiocontrast Nephropathy: Identifying the High-Risk Patient and the Implications of Exacerbating Renal Function, Rev Cardiovasc Med. 2003, vol. 4, Supp. 1, 2003 MedReviews, LLC, pp. S7-S14.
Non-Final Office Action; U.S. Appl. No. 10/408,665; dated Mar. 21, 2006, 14 pgs.
Non-Final Office Action; U.S. Appl. No. 11/129,765; dated May 18, 2007, 10 pgs.
Non-Final Office Action; U.S. Appl. No. 11/129,765; dated Sep. 10, 2007, 5 pgs.
Non-Final Office Action; U.S. Appl. No. 11/129,765; dated Oct. 6, 2006, 30 pgs.
Non-Final Office Action; U.S. Appl. No. 11/133,925; dated Oct. 8, 2008, 41 pgs.
Non-Final Office Action; U.S. Appl. No. 11/144,173; dated Apr. 5, 2007, 33 pgs.
Non-Final Office Action; U.S. Appl. No. 11/144,173; dated Sep. 10, 2007, 5 pgs.
Non-Final Office Action; U.S. Appl. No. 11/144,298; dated Oct. 29, 2009, 8 pgs.
Non-Final Office Action; U.S. Appl. No. 11/144,298; dated Apr. 5, 2007, 33 pgs.
Non-Final Office Action; U.S. Appl. No. 11/144,298; dated Sep. 10, 2007, 5 pgs.
Non-Final Office Action; U.S. Appl. No. 11/144,298; dated Dec. 29, 2008, 7 pgs.
Non-Final Office Action; U.S. Appl. No. 11/145,122; dated Apr. 11, 2007, 33 pgs.
Non-Final Office Action; U.S. Appl. No. 11/145,122; dated Sep. 10, 2007, 5 pgs.
Non-Final Office Action; U.S. Appl. No. 11/189,563; dated May 28, 2009, 5 pgs.
Non-Final Office Action; U.S. Appl. No. 11/233,814; dated Jun. 17, 2008, 12 pgs.
Non-Final Office Action; U.S. Appl. No. 11/252,462; dated Feb. 22, 2010, 6 pgs.

(56) References Cited

OTHER PUBLICATIONS

Non-Final Office Action; U.S. Appl. No. 11/266,993; dated Jul. 8, 2009, 5 pgs.
Non-Final Office Action; U.S. Appl. No. 11/266,993; dated Dec. 30, 2008, 7 pgs.
Non-Final Office Action; U.S. Appl. No. 11/363,867; dated Sep. 25, 2008, 10 pgs.
Non-Final Office Action; U.S. Appl. No. 11/368,553; dated May 18, 2010, 4 pgs.
Non-Final Office Action; U.S. Appl. No. 11/368,553; dated Oct. 7, 2009, 5 pgs.
Non-Final Office Action; U.S. Appl. No. 11/368,809; dated Dec. 3, 2009, 4 pgs.
Non-Final Office Action; U.S. Appl. No. 11/368,949; dated Jun. 11, 2010, 6 pgs.
Non-Final Office Action; U.S. Appl. No. 11/368,971; dated Aug. 24, 2010, 9 pgs.
Non-Final Office Action; U.S. Appl. No. 11/451,728; dated Jun. 12, 2008, 41 pgs.
Non-Final Office Action; U.S. Appl. No. 11/451,728; dated Jul. 2, 2009, 5 pgs.
Non-Final Office Action; U.S. Appl. No. 11/451,728; dated Dec. 28, 2009, 7 pgs.
Non-Final Office Action; U.S. Appl. No. 11/504,117; dated Mar. 31, 2009, 10 pgs.
Non-Final Office Action; U.S. Appl. No. 11/599,649; dated Mar. 30, 2009, 10 pgs.
Non-Final Office Action; U.S. Appl. No. 11/599,649; dated Jun. 23, 2008, 9 pgs.
Non-Final Office Action; U.S. Appl. No. 11/599,723; dated Jun. 26, 2009, 17 pgs.
Non-Final Office Action; U.S. Appl. No. 11/599,723; dated Oct. 15, 2010, 16 pgs.
Non-Final Office Action; U.S. Appl. No. 11/599,882; dated Jun. 6, 2009, 13 pgs.
Non-Final Office Action; U.S. Appl. No. 11/688,178; dated Jun. 28, 2010, 5 pgs.
Non-Final Office Action; U.S. Appl. No. 11/840,142; dated Apr. 3, 2009, 13 pgs.
Non-Final Office Action; U.S. Appl. No. 12/567,521; dated Sep. 3, 2010, 9 pgs.
Non-Final Office Action; U.S. Appl. No. 12/725,375; dated Oct. 12, 2010, 14 pgs.
Nozawa, T.et al., Effects of Long Term Renal Sympathetic Denervation on Heart Failure After Myocardial Infarction in Rats, Sep. 22, 2001, Heart Vessels, 2002, 16, Springer-Verlag 2002, pp. 51-56.
O'Hagan, K.P. et al., Renal denervation decreases blood pressure in DOCA-treated miniature swine with established hypertension, Am J Hypertens., 1990, 3:62-64.
Onesti, G. et al., Blood pressure regulation in end-stage renal disease and anephric man, Circ Res Suppl., 1975, 36 & 37: 145-152.
Osborn, et al., Effect of renal nerve stimulation on renal blood flow autoregulation and antinatriuresis during reductions in renal perfusion pressure, in Proceedings of the Society for Experimental Biology and Medicine, vol. 168, 77-81, 1981. (Abstract).
Packer, Douglas L. et al., Clinical Presentation, Investigation, and Management of Pulmonary Vein Stenosis Complication Ablation for Atrial Fibrillation, Circulation: Journal of the American Heart Association. Feb. 8, 2005. pp. 546-554.
Page, I.H. et al., The Effect of Renal Denervation on the Level of Arterial Blood Pressure and Renal Function in Essential Hypertension. J Clin Invest. 1934;14:27-30.
Page, I.H., et al., The Effect of Renal Efficiencyof Lowering Arterial Blood Pressure in Cases of Essential Nephritis, Hospital of the Rockefeller Institue, Jul. 12, 1934, 7 pgs.
Palmer, Biff, F., M.D., Managing Hyperkalemia Caused by Inhibitors of the Renin-Angiotensin-Aldosterone System, Aug. 5, 2004, The New England Journal of Medicine 2004, vol. 351;6, 2004 Massachusetts Medical Society, pp. 585-592.
Pappone, Carlo et al., [2005][P2-70] Safety Report of Circumferential Pulmonary Vein Ablation. A 9-Year Single-Center Experience on 6,442 Patients with Atrial Fibrillation, Abstract only. 1 page, May 2005.
Pappone, Carlo et al., [2004][759] Pulmonary Vein Denervation Benefits Paroxysmal Atrial Fibrillation Patients after Circumferential Ablation, Abstract only. 1 page, Jan. 5, 2004.
Pappone, Carol and Santinelli, Vincenzo. Multielectrode basket catheter: A new tool for curing atrial fibrillation? Heart Rhythm, vol. 3, Issue 4, pp. 385-386. Apr. 2006.
Peacock, J.M. and R. Orchardson, Action potential conduction block of nerves in vitro by potassium citrate, potassium tartrate and potassium oxalate, May 6, 1998, Journal of Clinical Periodontology, Munksgaard 1999, vol. 26, pp. 33-37.
Petersson, M. et al., Long-term outcome in relation to renal sympathetic activity in patients with chronic heart failure. Eur Heart J. 2005;26:906-13.
Pettersson, A. et al., Renal interaction between sympathetic activity and ANP in rats with chronic ischaemic heart failure, Nov. 25, 1988, Acta Physiol Scand 1989, 135, pp. 487-492.
PHCL 762 Pharmacology of the Autonomic Nervous System, Chapter 2 and 6.8 in Mosby, http://www.kumc.edu/research/medicine/pharmacology/CAI/phcl762.html, last accessed Aug. 24, 2004, 14 pgs.
Pitt, B. et al., Effects of Eplerenone, Enalapril, and Eplerenone/Enalapril in Patients With Essential Hypertension and Left Ventricular Hypertrophy: The 4E-Left Ventricular Hypertrophy Study, Circulation, 2003, vol. 108, pp. 1831-1838.
Pliquett, U., Joule heating during solid tissue electroporation, Oct. 22, 2002, Med. Biol. Eng. Comput., 2003, vol. 41, pp. 215-219.
Podhajsky R.J. et al, The Histologic Effects of Pulsed and Continuous Radiofrequency Lesions at 42 C to Rat Dorsal Root Ganglion and Sciatic Nerve, Spine, vol. 30, No. 9, 2005, Lippincott Williams & Wilkins Inc., pp. 1008-1013.
Pope, Jill. Fixing a Hole: Treating Injury by Repairing Cells. The New York Academy of Sciences. Jul. 6, 2006. 6 pgs.
Popovic, Jennifer R. and Margaret J. Hall, 1999 National Hospital Discharge Survey, Apr. 24, 2001, Advance Data, No. 319, CDC, pp. 1-17 & 20.
Practice Guidelines Writing Committee and ESH/ESC Hypertension Guidelines Committee, Practice Guidelines for Primary Care Physicians: 2003 ESH/ESC Hypertension Guidelines, Published in Journal of Hypertension 2003, vol. 21, No. 10: 1011-1053, European Society of Hypertension 2003, pp. 1779-1786.
Programmable Infusion System, Pumps and Pump Selection, Medtronic Pain Therapies, Medtronic, Inc. Sep. 5, 2001, 2 pgs.
Pucihar, Gorazd et al., The influence of medium conductivity on electropermeabilization and survival of cells in vitro, May 31, 2001, Bioelectrochemistry, vol. 54, 2001, Elsevier Science B.V. 2001, pp. 107-115.
Pulmonary Concepts in Critical Care Breath Sounds, http://rnbob.tripod.com/breath.htm, last accessed Aug. 23, 2004, 5 pages.
Pulmonary Function Testing, http://jan.ucc.nau.edu/~daa/lecture/pft.htm, last accessed Aug. 23, 2004, 8 pages.
Purerfellner, Helmut and Martinek, Martin. Pulmonary vein stenosis following catheter ablation of atrial fibrillation. Current Opinion in Cardiology. 20; pp. 484-490. 2005.
Purerfellner, Helmut et al., Pulmonary Vein Stenosis by Ostial Irrigated-Tip Ablation: Incidence, Time Course, and Prediction, Journal of Cardiovascular Electrophysiology. vol. 14, No. 2, Feb. 2003. pp. 158-164.
Raji, A. R. M. and R. E. M. Bowden, Effects of High-Peak Pulsed Electromagnetic Field on the Degeneration and Regeneration of the Common Peroneal Nerve in Rats, The Journal of Bone and Joint Surgery Aug. 1983, vol. 65-B, No. 4, 1983 British Editorial Society of Bone and Joint Surgery, pp. 478-492.
Ram, C. Venkata S., M.D., Understanding refractory hypertension, May 15, 2004, Patient Care May 2004, vol. 38, pp. 12-16, 7 pages from http://www.patientcareonline.com/patcare/content/printContentPopup.jsp?id=108324.
Ravalia, A. et al., Tachyphylaxis and epidural anaesthesia, Edgware General Hospital, Correspondence, p. 529, Jun. 1989.

(56) References Cited

OTHER PUBLICATIONS

Renal Parenchymal Disease, Ch. 26, 5th Edition Heart Disease, a Textbook of Cardiovascular Medicine vol. 2, Edited by Eugene Braunwald, WB Saunders Company, pp. 824-825 1997.
Ribstein, Jean and Michael H. Humphreys, Renal nerves and cation excretion after acute reduction in functioning renal mass in the rat, Sep. 22, 1983, Am. J. Physiol., vol. 246, 1984 the American Physiological Society, pp. F260-F265.
Richebe, Philippe, M.D. et al., Immediate Early Genes after Pulsed Radiofrequency Treatment: Neurobiology in Need of Clinical Trials, Oct. 13, 2004, Anesthesiology Jan. 2005, vol. 102, No. 1, 2004 American Society of Anesthesiologists, Inc. Lippincott Williams & Wilkins, Inc., pp. 1-3.
Rihal, Charanjit S. et al., Incidence and Prognostic Importance of Acute Renal Failure After Percutaneous Coronary Intervention, Mar. 6, 2002, Circulation May 14, 2002, vol. 10, 2002 American Heart Association, Inc., pp. 2259-2264.
Rosen S.M. et al., Relationship of Vascular Reactivity to Plasma Renin Concentration in Patients with Terminal Renal Failure, Proc. Dialysis Transplant Forum 1974, pp. 45-47.
Roth, Bradley J. and Peter J. Basser, A Model of the Stimulation of a Nerve Fiber by Electromagnetic Induction, IEEE Transactions on Biomedical Engineering, vol. 37, No. 6, Jun. 1990, pp. 588-597.
Rudin, Asa, M.D. et al., Postoperative Epidural or Intravenous Analgesia after Major Abdominal or Thoraco-Abdominal Surgery, The Journal of the American Society of Anesthesiologists, Inc., Anesthesiology 2001, vol. 95, A-970, 1 page.
Rudnick, Michael R. et al., Contrast-induced nephropathy: How it develops, how to prevent it, Cleveland Clinic Journal of Medicine Jan. 2006, vol. 73, No. 1, pp. 75-87.
Rump, L.C., The Role of Sympathetic Nervous Activity in Chronic Renal Failure, J Clinical Basic Cardiology 2001, vol. 4, pp. 179-182.
Ruohonen, Jarmo et al., Modeling Peripheral Nerve Stimulation Using Magnetic Fields, Journal of the Peripheral Nervous System, vol. 2, No. 1, 1997, Woodland Publications 1997, pp. 17-29.
Saad, Eduardo B. et al., Pulmonary Vein Stenosis After Radiofrequency Ablation of Atrial Fibrillation: Functional Characterization, Evolution, and Influence of the Ablation Strategy, Circulation. 108; pp. 3102-3107. 2003.
Sabbah, Hani N., Animal Models for Heart Failure and Device Development, Henry Ford Health System. 24 slides, Oct. 17, 2005.
Schauerte, P et al., Focal atrial fibrillation: experimental evidence for a pathophysiologic role of the autonomic nervous system, Journal of Cardiovascular Electrophysiology. 12(5). May 2001. Abstract only. 2 pgs.
Schauerte, P et al., Catheter ablation of cardiac autonomic nerves for prevention of vagal atrial fibrillation, Circulation. 102(22). Nov. 28, 2000. Abstract only. 2 pgs.
Schauerte, P et al., Transvenous parasympathetic nerve stimulation in the inferior vena cava and atrioventricular conduction, Journal of Cardiovascular Electrophysiology. 11(1). Jan. 2000. Abstract only. 2 pgs.
Scheiner, Avram, Ph.D., The design, development and implementation of electrodes used for functional electrial stimulation, Thesis paper, Case Western Reserve University, May 1992, 220 pages.
Scherlag, BJ and Po, S., The intrinsic cardiac nervous system and atrial fibrillation, Current Opinion in Cardiology. 21(1):51-54, Jan. 2006. Abstract only. 2 pgs.
Schlaich, M.P. et al., Relation between cardiac sympathetic activity and hypertensive left ventricular hypertrophy. Circulation. 2003;108:560-5.
Schlaich, M.P. et al., Sympathetic augmentation in hypertension: role of nerve firing, norepinephrine reuptake, and angiotensin neuromodulation, Hypertension, 2004, 43:169-175.
Schmitt, Joseph et al., Intravascular Optical Coherence Tomography—Opening a Window into Coronary Artery Disease, LightLab Imaging, Inc. Business Briefing: European Cardiology 2005.

Schoenbach, Karl H. et al, Intracellular Effect of Ultrashort Electrical Pulses, Dec. 26, 2000, Bioelectromagnetics, vol. 22, 2001, Wiley-Liss, Inc. 2001, pp. 440-448.
Schrier, Robert et al., Cardiac and Renal Effects of Standard Versus Rigorous Blood Pressure Control in Autosomal-Dominant Polycistic Kidney Disease, Mar. 23, 2002, Journal of the American Society of Nephrology, American Society of Nephrology 2002, pp. 1733-1739.
Scremin, Oscar U., M.D., Ph.D. and Daniel P. Holschneider, M.D., 31 & 32 . . . An Implantable Bolus Infusion Pump for the Neurosciences, FRP, Apr. 2005, 3 pages.
Sensorcaine—MPF Spinal Injection, informational document, AstraZeneca 2001, 2 pgs.
Shah, D.C., Haissaguerre, M., Jais, P., Catheter ablation of pulmonary vein foci for atrial fibrillation: pulmonary vein foci ablation for atrial firbrillation, Thorac Cardiovasc Surg, 1999, 47 (suppl. 3): 352-356.
Shannon, J.L. et al., Studies on the innervation of human renal allografts, J Pathol. 1998, vol. 186, pp. 109-115.
Shlipak, M.G. et al., The clinical challenge of cardiorenal syndrome. Circulation. 2004;110:1514-7.
Shupak, Naomi M., Therapeutic Uses of Pulsed Magnetic-Field Exposure: A Review, Radio Science Bulletin Dec. 2003, No. 307, pp. 9-32.
Shu-Qing, Liu et al., Old spinal cord injury treated by pulsed electric stimulation, General Hospital of Beijing Command, Beijing, Dec. 6, 1990, 5 pages (full article in Chinese; abstract on last page).
Siegel, RJ et al., Clinical demonstration that catheter-delivered ultrasound energy reverses arterial vasoconstriction, Journal of the American College of Cardiology. 1992. 20; 732-735. Summary only. 2 pgs.
Simpson, B. et al., Implantable spinal infusion devices for chronic pain and spasticity: an accelerated systematic review, ASERNIP-S Report No. 42, Adelaide, South Australia, ASERNIP-S, May 2003, 56 pages.
Sisken, B.F. et al., 229.17 Influence of Non-Thermal Pulsed Radiofrequency Fields (PRF) on Neurite Outgrowth, Society for Neuroscience, vol. 21, 1995, 2 pages.
Skeie, B. et al., Effect of chronic bupivacaine infusion on seizure threshold to bupivacaine, Dec. 28, 1986, Acta Anaesthesiol Scand 1987, vol. 31, pp. 423-425.
Skopec, M., A Primer on Medical Device Interactions with Magnetic Resonance Imaging Systems, Feb. 4, 1997, CDRH Magnetic Resonance Working Group, U.S. Department of Heatlh and Human Services, Food and Drug Administration, Center for Devices and Radiological Health, Updated May 23, 1997, 17 pages, http://www.fda.gov/cdrh/ode/primerf6.html, (last accessed Jan. 23, 2006.
Slappendel, Robert et al., The efficacy of radiofrequency lesioning of the cervical spinal dorsal root ganglion in a double blinded randomized study, Jun. 26, 1997, Pain 73, 1997 International Association for the Study of Pain, Elsevier Science B.V., pp. 159-163.
Sluijter, M.D., Ph.D., Pulsed Radiofrequency, May 17, 2005, Anesthesiology Dec. 2005, vol. 103, No. 6, 2005 American Society of Anesthesiologists, Inc. Lippincott Williams & Wilkins, Inc., pp. 1313-1314.
Sluijter, M.D., Ph.D., Radiofrequency Part 1: The Lumbosacral Region, Chapter 1 Mechanisms of Chronic Pain and part of Chapter 2 Spinal Pain, 2001 FlivoPress SA, Meggen (LU), Switzerland, pp. 1-26.
Sluijter, M.D., Ph.D., Radiofrequency Part 2: Thoracic and Cervical Region, Headache and Facial Pain, various pages from, FlivoPress SA, Meggen (LU), Switzerland, 13 pages 2002.
Sluijter, M.D., Ph.D., The Role of Radiofrequency in Failed Back Surgery Patients, Current Review of Pain 2000, vol. 4, 2000 by Current Science Inc., pp. 49-53.
Smithwick, R.H. et al., Hypertension and associated cardiovascular disease: comparison of male and female mortality rates and their influence on selection of therapy, JAMA, 1956, 160:1023-1033.
Smithwick, R.H. et al., Splanchnicectomy for essential hypertension, Journal Am Med Assn, 1953;152:1501-1504.
Smithwick, R.H., Surgical treatment of hypertension, Am J Med 1948, 4:744-759.

(56) References Cited

OTHER PUBLICATIONS

Sobotka, Paul A., Treatment Strategies for Fluid Overload, CHF Patients, CHF Solutions. Transcatheter Cardiovascular Therapeutics 2005. 20 slides.

Solis-Herruzo, J.A. et al., Effects of lumbar sympathetic block on kidney function in cirrhotic patients with hepatorenal syndrome, Journal of Hepatology, 1987; 5: 167-173.

Souza, D.R.B. et al., Chronic experimental myocardial infarction produces antinatriuresis by a renal nerve-dependent mechanism, Oct. 14, 2003, Brazilian Journal of Medical and Biological Research 2004, vol. 37, pp. 285-293.

Standl, Thomas, M.D., et al., Patient-controlled epidural analgesia reduces analgesic requirements compared to continuous epidural infusion after major abdominal surgery, Aug. 29, 2002, Canada Journal of Anesthesia 2003, vol. 50 (3), pp. 258-264.

Steffen, W. et al., Catheter-delivered high intensity, low frequency ultrasound induces vasodilation in vivo, European Heart Journal. 1994. 15; pp. 369-376.

Steg, PG et al., Pulsed ultraviolet laser irradiation produces endothelium-independent relaxation of vascular smooth muscle, Circulation: Journal of the American Heart Association. 1989. pp. 189-197.

Stone, Gregg W., M.D. et al., Fenoldopam Mesylate for the Prevention of Contrast-Induced Nephropathy, JAMA Nov. 5, 2003, vol. 290, No. 17, 2003 American Medical Association, pp. 2284-2291.

Strojek, K. et al., Lowering of microalbuminuria in diabetic patients by a sympathicoplegic agent: novel approach to prevent progression of diabetic nephropathy? J Am Soc Nephrol. 2001;12:602-5.

Summary, Critical Reviews in Biomedical Engineering, vol. 17, Issue 5, 1989, pp. 515-529.

Sung, Duk Hyun, M.D. et al., Phenol Block of Peripheral Nerve Conduction: Titrating for Optimum Effect, Jun. 27, 2000, Arch. Phys. Med. Rehabil. vol. 82, May 2001, pp. 671-676.

Taka, Tomomi et al., Impaired Flow-Mediated Vasodilation in vivo and Reduced Shear-Induced Platelet Reactivity in vitro in Response to Nitric Oxide in Prothrombotic, Stroke-Prone Spontaneously Hypertensive Rats, Pathophysiology of Haemostasis and Thrombosis. Dec. 23, 2002. pp. 184-189.

Taler, Sandra J. et al., Resistant Hypertension, Comparing Hemodynamic Management to Specialist Care, Mar. 12, 2002, Hypertension 2002, vol. 39, 2002 American Heart Association, Inc., pp. 982-988.

Tamborero, David et al., Incidence of Pulmonary Vein Stenosis in Patients Submitted to Atrial Fibrillation Ablation: A Comparison of the Selective Segmental Ostial Ablation vs. the Circumferential Pulmonary Veins Ablation, Journal of Intervocational Cardiac Electrophysiology. 14; pp. 41-25. 2005.

Tay, Victoria KM, et al., Computed tomography fluoroscopy-guided chemical lumbar sympathectomy: Simple, safe and effective, Oct. 31, 2001, Diagnostic Radiology, Australasian Radiology 2002, vol. 46, pp. 163-166.

Terashima, Mitsuyasu et al. Feasibility and Safety of a Novel CryoPlasty™ System. Poster. 1 page, Mar. 15, 2002.

Thatipelli et al., CT Angiography of Renal Artery Anatomy for Evaluating Embolic Protection Devices, Journal of Vascular and Interventional Radiology, Jul. 2007, pp. 842-846.

The Antihypertensive and Lipid-Lowering Treatment to Prevent Heart Attack Trial, AllHat Research Group, JAMA, 2002, vol. 288, pp. 2981-2997.

Thomas, John R. and Oakley, E. Howard N. Chapter 15: Nonfreezing Cold Injury Medical Aspects of Harsh Environments, vol. 1. pp. 467-490, 2001.

Thompson, Gregory W., et al., Bradycardia Induced by Intravascular Versus Direct Stimulation of the Vagus Nerve, Aug. 24, 1997, The Society of Thoracic Surgeons 1998, pp. 637-642.

Thrasher, Terry N., Unloading arterial baroreceptors causes neurogenic hypertension, Dec. 4, 2001, Am J. Physiol Regulatory Integrative Comp Physiol, vol. 282, 2002 the American Physiological Society, pp. R1044-R1053.

Tokuno, Hajime A. et al., Local anesthetic effects of cocaethylene and isopropylcocaine on rat peripheral nerves, Oct. 7, 2003, Brain Research 996, 2004, Elsevier B.V. 2003, pp. 159-167.

Trapani, Angelo J. et al., Neurohumoral interactions in conscious dehydrated rabbit, Am. J. Physiol. 254, 1988, the American Physiological Society 1988, pp. R338-R347.

Trock, David H. et al., The Effect of Pulsed Electromagnetic Fields in the Treatment of Osteoarthritis of the Knee and Cervical Spine. Report of Randomized, Double Blind, Placebo Controlled Trials, Mar. 22, 1994, The Journal of Rheumatology 1994, vol. 21, pp. 1903-1911.

Troiano, Gregory C. et al., The Reduction in Electroporation Voltages by the Addition of a Surfactant to Planar Lipid Bilayers, May 12, 1998, Biophysical Journal, vol. 75, Aug. 1998, the Biophysical Society 1998, pp. 880-888.

Trumble, Dennis R. and James A. MaGovern, Comparison of Dog and Pig Models for Testing Substernal Cardiac Compression Devices, Nov. 2003, ASAIO Journal 2004, pp. 188-192.

Tsai, E., Intrathecal drug delivery for pain indications, technique, results, Pain Lecture presentation, Jun. 8, 2001, 31 pages.

Uematsu, Toshihiko, M.D., Ph.D., F.I.C.A. et al., Extrinsic Innervation of the Canine Superior Vena Cava, Pulmonary, Portal and Renal Veins, Angiology—Journal of Vascular Diseases, Aug. 1984, pp. 486-493.

United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.

Upadhyay, Pramod, Electroporation of the skin to deliver antigen by using a piezo ceramic gas igniter, Jan. 27, 2001, International Journal of Pharmaceutics, vol. 217, 2001 Elsevier Science B.V., pp. 249-253.

Valente, John F. et al., Laparoscopic renal denervation for intractable ADPKD-related pain, Aug. 24, 2000, Nephrol Dial Transplant 2001, vol. 16, European Renal Association-European Dialysis and Transplant Association, p. 160.

Van Antwerp, Bill and Poonam Gulati, Protein Delivery from Mechanical Devices Challenges and Opportunities, Medtronic presentation, 19 pages, Jul. 2003.

Velazquez, Eric J., An international perspective on heart failure and left ventricular systolic dysfunction complicating myocardial infarction: the Valiant registry, Aug. 5, 2004, European Heart Journal vol. 25, 2004 Elsevier, pp. 1911-1919.

Velez-Roa, Sonia, M.D. et al., Peripheral Sympathetic Control During Dobutamine Infusion: Effects of Aging and Heart Failure, Jul. 7, 2003, Journal of the American College of Cardiology, vol. 42, No. 9, 2003, American College of Cardiology Foundation 2003, pp. 1605-1610.

Villarreal, Daniel et al., Effects of renal denervation on postprandial sodium excretion in experimental heart failure, Oct. 29, 1993, Am J Physiol 266, 1994, pp. R1599-R1604.

Villarreal, Daniel et al., Neurohumoral modulators and sodium balance in experimental heart failure, Nov. 6, 1992, Am. J. Physiol, vol. 264, 1993, pp. H1187-H1193.

Vonend, O. et al., Moxonidine treatment of hypertensive patients with advanced renal failure. J Hypertens. 2003;21:1709-17.

Wagner, C.D. et al., Very low frequency oscillations in arterial blood pressure after autonomic blockade in conscious dogs, Feb. 5, 1997, Am J Physiol Regul Integr Comp Physiol 1997, vol. 272, 1997 the American Physiological Society, pp. 2034-2039.

Wald, Jan D., Ph.D, et al., Cardiology Update: 2003, Sep. 11, 2003, AG Edwards 2003, 120 pages.

Wang, Xi et al., Alterations of adenylyl cyclase and G proteins in aortocaval shunt-induced heart failure, Jul. 2004, Am J Physiol Heart Circ Physiol vol. 287, 2004 the American Physiological Society, pp. H118-H125.

Weaver, James C., Chapter 1 Electroporation Theory, Concepts and Mechanisms, Methods in Molecular Biology, vol. 55, Plant Cell Electroporation and Electrofusion Protocols, Edited by J.A. Nickoloff, Humana Press Inc., pp. 3-28, 1995.

Weaver, James C., Electroporation: A General Phenomenon for Manipulating Cells and Tissues, Oct. 22, 1992, Journal of Cellular Biochemistry, vol. 51, 1993 Wiley-Liss, Inc., pp. 426-435.

(56) References Cited

OTHER PUBLICATIONS

Weiner, Richard L., M.D., Peripheral nerve neurostimulation, Neurosurg. Clin. N. Am. vol. 14, 2003, Elsevier, Inc. 2003, pp. 401-408.
Weisbord, Steven D., M.D. and Paul M. Palevsky, M.D., Radiocontrast-Induced Acute Renal Failure, Jul. 10, 2004, Journal of Intensive Care Medicine 2005, vol. 20 (2), 2005 Sage Publications, pp. 63-75.
Whitelaw, G.P., Kinsey, D., Smithwick, R.H., Factors influencing the choice of treatment in essential hypertension: surgical, medical, or a combination of both, Am J Surg, 1964, 107:220-231.
Wilson, D.H. et al., The Effects of Pulsed Electromagnetic Energy on Peripheral Nerve Regeneration, Annals New York Academy of Sciences, Oct. 1974, pp. 575-585.
Wolinsky, Harvey, M.D. PhD and Swan N. Thung, M.D., Use of a Perforated Balloon Catheter to Deliver Concentrated Heparin Into the Wall of the Normal Canine Artery, Aug. 30, 1989, JACC 1990, vol. 15, 1990 by the American College of Cardiology, pp. 475-481.
Wyss, J. Michael et al., Neuronal control of the kidney: Contribution to hypertension, Apr. 8, 1991, Can. J. Physiol. Pharmacol. 1992;70: 759-770.
Yamaguchi, Jun-ichi, M.D. et al., Prognostic Significance of Serum Creatinine Concentration for in-Hospital Mortality in Patients with Acute Myocardial Infarction Who Underwent Successful Primary Percutaneous Coronary Intervention (from the Heart Institute of Japan Acute Myocardial Infarction [HIJAMI] Registry), Feb. 24, 2004, The American Journal of Cardiology vol. 93, Jun. 15, 2004, 2004 by Excerpta Medica, Inc., pp. 1526-1528.
Ye, Richard D., M.D., Ph.D., Pharmacology of the Peripheral Nervous System, E-425 MSB, 6 pages, Jan. 2000.
Ye, S. et al., A limited renal injury may cause a permanent form of neurogenic hypertension. Am J Hypertens. 1998;11:723-8.
Ye, Shaohua et al., Renal Injury Caused by Intrarenal Injection of Pheno Increases Afferent and Efferent Renal Sympathetic Nerve Activity, Mar. 12, 2002, American Journal of Hypertension, Aug. 2002, vol. 15, No. 8, 2002 the American Journal of Hypertension, Ltd. Published by Elsevier Science Inc., pp. 717-724.
Yong-Quan, Dong et al., The therapeutic effect of pulsed electric field on experimental spinal cord injury, Beijing Army General Hospital of People's Liberation Army, Beijing, 5 pages (full article in Chinese; abstract on last page) Mar. 30, 1992.
Young, James B., M.D., FACC, Management of Chronic Heart Failure: What Do Recent Clinical Trials Teach Us?, Reviews in Cardiovascular Medicine, vol. 5, Suppl. 1, 2004, MedReviews, LLC 2004, pp. S3-S9.
Yu, Wen-Chung et al. Acquired Pulmonary Vein Stenosis after Radiofrequency Catheter Ablation of Paroxysmal Atrial Fibrillation. Journal of Cardiovascular Electrophysiology. vol. 12, No. 8. Aug. 2001. pp. 887-892.
Zanchetti, A. et al., Neural Control of the Kidney—Are There Reno-Renal Reflexes?, Clin. and Exper. Hyper. Theory and Practice, A6 (1&2), 1984, Marcel Dekker, Inc. 1984, pp. 275-286.
Zanchetti, A. et al., Practice Guidelines for Primary Care Physicians: 2003 ESH/ESC Hypertension Guidelines, Journal of Hypertension, vol. 21, No. 10, 2003, pp. 1779-1786.
Zanchetti, A.S., Neural regulation of renin release: Experimental evidence and clinical implications in arterial hypertension, Circulation, 1977, 56(5) 691-698.
Zimmermann, Ulrich, Electrical Breakdown, Electropermeabilization and Electrofusion, Rev. Physiol. Biochem. Pharmacol., vol. 105, Springer-Verlag 1986, pp. 175-256.
Zoccali, C. et al., Plasma norepinephrine predicts survival and incident cardiovascular events in patients with end-stage renal disease. Circulation. 2002;105:1354-9.
Zundert, Jan Van, M.D. Fipp and Alex Cahana, M.D. DAAPM, Pulsed Radiofrequency in Chronic Pain Management: Looking for the Best Use of Electrical Current, Pain Practice 2005, vol. 5, Issue 2, 2005 World Institute of Pain, pp. 74-76.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter,"Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. 2465470, dated Oct. 28, 2015, Date of Opposition dated Jul. 27, 2016, 34 pp.
Opposition to European Patent No. EP1802370, dated Jan. 5, 2011, Date of Opposition dated Oct. 5, 2011, 20 pages.
Opposition to European Patent No. EP2037840, dated Dec. 7, 2011, Date of Opposition dated Sep. 7, 2012, 25 pages.
Opposition to European Patent No. EP2092957, dated Jan. 5, 2011, Date of Opposition dated Oct. 5, 2011, 26 pages.
Oz, Mehmet, Pressure Relief, Time, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper, et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.
Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pgs.
U.S. Appl. No. 60/852,787, filed Oct. 18, 2006, 112 pgs.
Ureter, https://en.wikipedia.org/wiki/Ureter, Jun. 2016, 6 pgs.

(56) References Cited

OTHER PUBLICATIONS

Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Associatio3766merica Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news--latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global Symplicity registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Curtis, J.J., et al., "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62, No. 3, 2013, 11 pages.
Demarais et al., Reexamination U.S. Appl. No. 95/002,110 U.S. Pat. No. 7717948 filed Aug. 29, 2012.
DeMarais et al., Reexamination U.S. Appl. No. 95/002,253 U.S. Pat. No. 8131371 filed Sep. 13, 2012.
DeMarais et al., Reexamination U.S. Appl. No. 95/002,255 U.S. Pat. No. 7617005 filed Sep. 13, 2012.
DeMarais et al., Reexamination U.S. Appl. No. 95/002,292 U.S. Pat. No. 8175711 filed Sep. 14, 2012.
DeMarais et al., Reexamination U.S. Appl. No. 95/002,335 U.S. Pat. No. 8150520 filed Sep. 14, 2012.
DeMarais et al., Reexamination U.S. Appl. No. 95/002,356 U.S. Pat. No. 8150519 filed Sep. 14, 2012.
DeMarias et al., Reexamination U.S. Appl. No. 95/002,327 U.S. Pat. No. 8145317 filed Sep. 14, 2012.
DiBona, G.F. "Sympathetic nervous system and kidney in hypertension." Nephrol and Hypertension, 11: 197-200 (2002).
DiBona, G.F., et al. "Neural control of renal function." Physiol Rev, 77:75-197 (1997).
Doumas, Michael et al., "Renal Nerve Ablation for Resistant Hypertension: The Dust Has Not Yet Settled." The Journal of Clinical Hypertension. 2014; vol. 16, No. 6, 2 pages.
Dubuc, M., et al., "Feasibility of cardiac cryoablation using a transvenous steerable electrode catheter." J Intery Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H et al. "Combined embolization and percutaneous radiofrequency ablation of a solid renal tumor." Am. J. Roentgenol,174: 1592-1594 (2000).
Han, Y.-M, et al., "Renal artery embolization with diluted hot contrast medium: An experimental study." J Vasc Intery Radiol, 12: 862-868 (2001).
Hansen, J. M., et al. "The transplanted human kidney does not achieve functional reinnervation." Clin. Sci, 87: 13-19 (1994).

(56) References Cited

OTHER PUBLICATIONS

Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Levin et al. Reexamination U.S.Appl. No. 95/002,209 U.S. Pat. No. 8150518 filed Sep. 13, 2012.
Levin et al., Reexamination U.S. Appl. No. 95/002,233 U.S. Pat. No. 8131372 filed Sep. 13, 2012.
Levin et al., Reexamination U.S. Appl. No. 95/002,243 U.S. Pat. No. 7162303 filed Sep. 13, 2012.
Levin et al., Reexamination U.S. Appl. No. 95/002,336 U.S. Pat. No. 7647115 filed Sep. 14, 2012.
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Messerli, Franz H. et al. "Renal Denervation for Resistant Hypertension: Dead or Alive?" Healio: Cardiology today's Intervention, May/Jun. 2014, 2 pages.
Millard, F. C., et al, "Renal Embolization for ablation of function in renal failure and hypertension." Postgraduate Medical Journal, 65, 729-734, (1989).
Miller, Reed, "Finding a Future for Renal Denervation With Better Controlled Trials." Pharma & Medtech Business Intelligence, Article # 01141006003, Oct. 6, 2014, 4 pages.
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Intium" (Doubt Is the Beginning of Wisdom)", Circulation Research, 2014; 115: 211-214.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter Ablation of Cardiac Autonomic Nerves for Prevention of Vagal Atrial Fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversable renal denervation on haemodynamic and excretory functions on the ipsilateral and contralateral kidney in the cat." Hypertension, 4: 181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." pace, 21:2517-2521 (1998).
Valente, J.F. "Laparoscopic renal denervation for intractable ADPKD-related pain." Nephrol Dial Transplant, 16: 160 (2001).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.

(56) References Cited

OTHER PUBLICATIONS

Worthley, Stephen, "The St. Jude Renal Denervation System Technology and Clinical Review." The University of Adelaide Australia, 2012, 24 pages.

Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.

Grassi, et al. "Baroreflex Control of Sympathetic Nerve Activity in Essential and Secondary Hypertension", Hypertension, 1998, vol. 31, pp. 68-72.

Kawada, et al. "Differential Dynamic Baroreflex Regulation of Cardiac and Renal Sympathetic Nerve Activities" American Journal of Physiology-Heart and Circulatory Physiology, 2001, vol. 280, H1581-H1590.

Potkay, "Long Term, Implantable Blood Pressure Monitoring Systems" Biomed Microdevices 2008, vol. 10, pp. 379-392.

Rea, et al."Baroreflex Control of Muscle Sympathetic Nerve Activity in Borderline Hypertension", Circulation, 1990, vol. 82 (3), pp. 856-862.

Search Report and Written Opinion dated Mar. 8, 2006 for PCT Application No. PCT/US2005/035693.

Search Report dated Oct. 17, 2013 for European Application No. 13159256.

\* cited by examiner

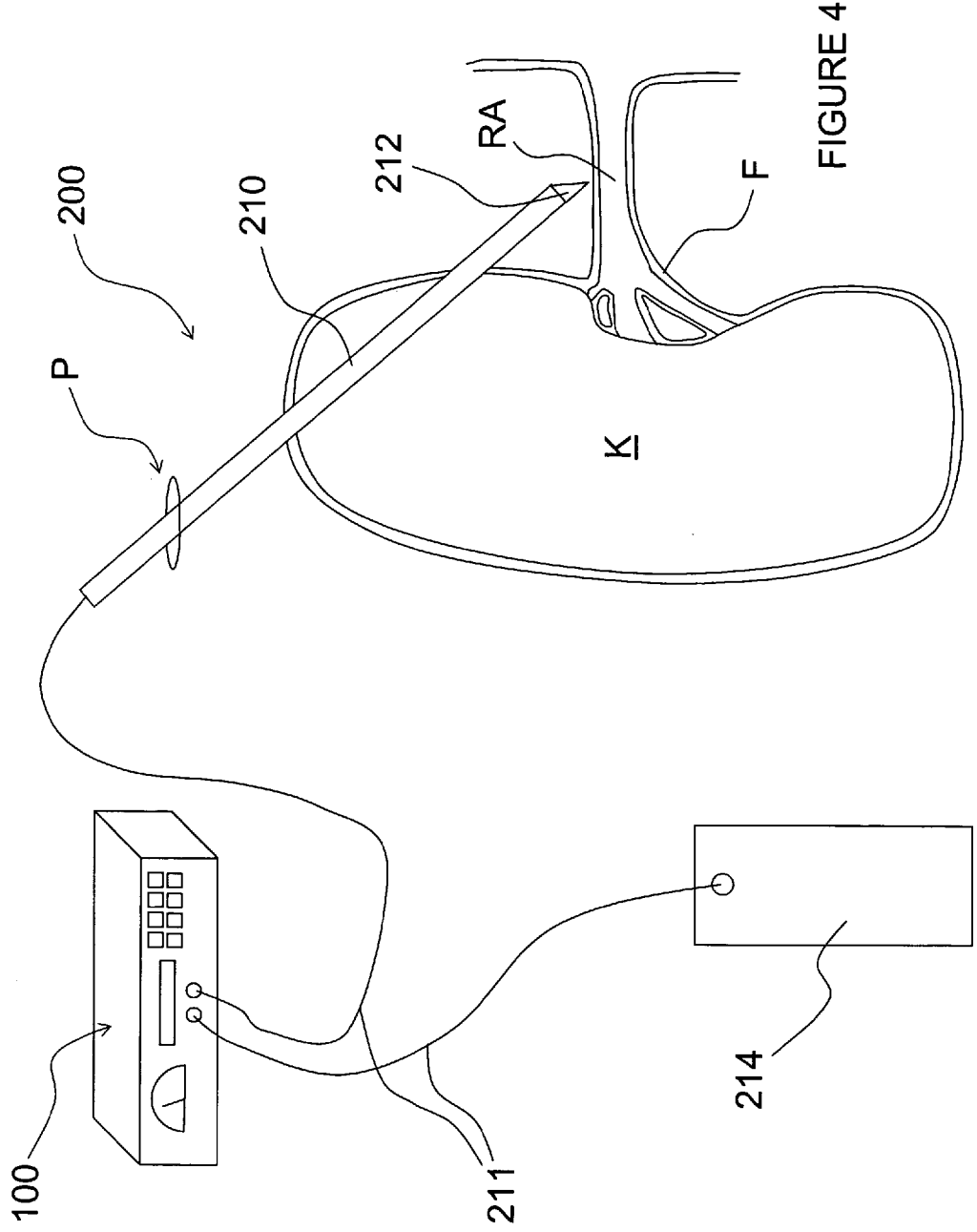

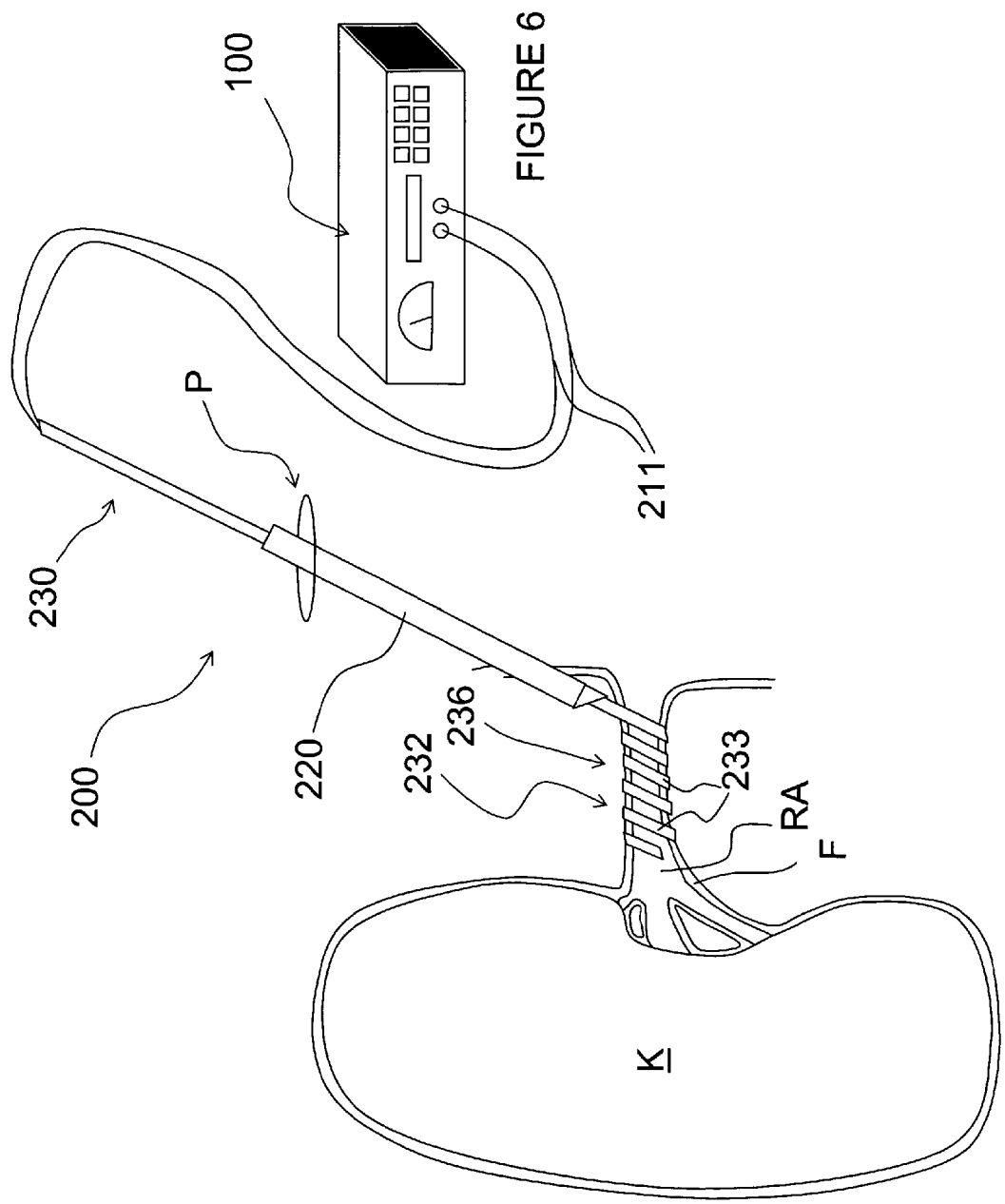

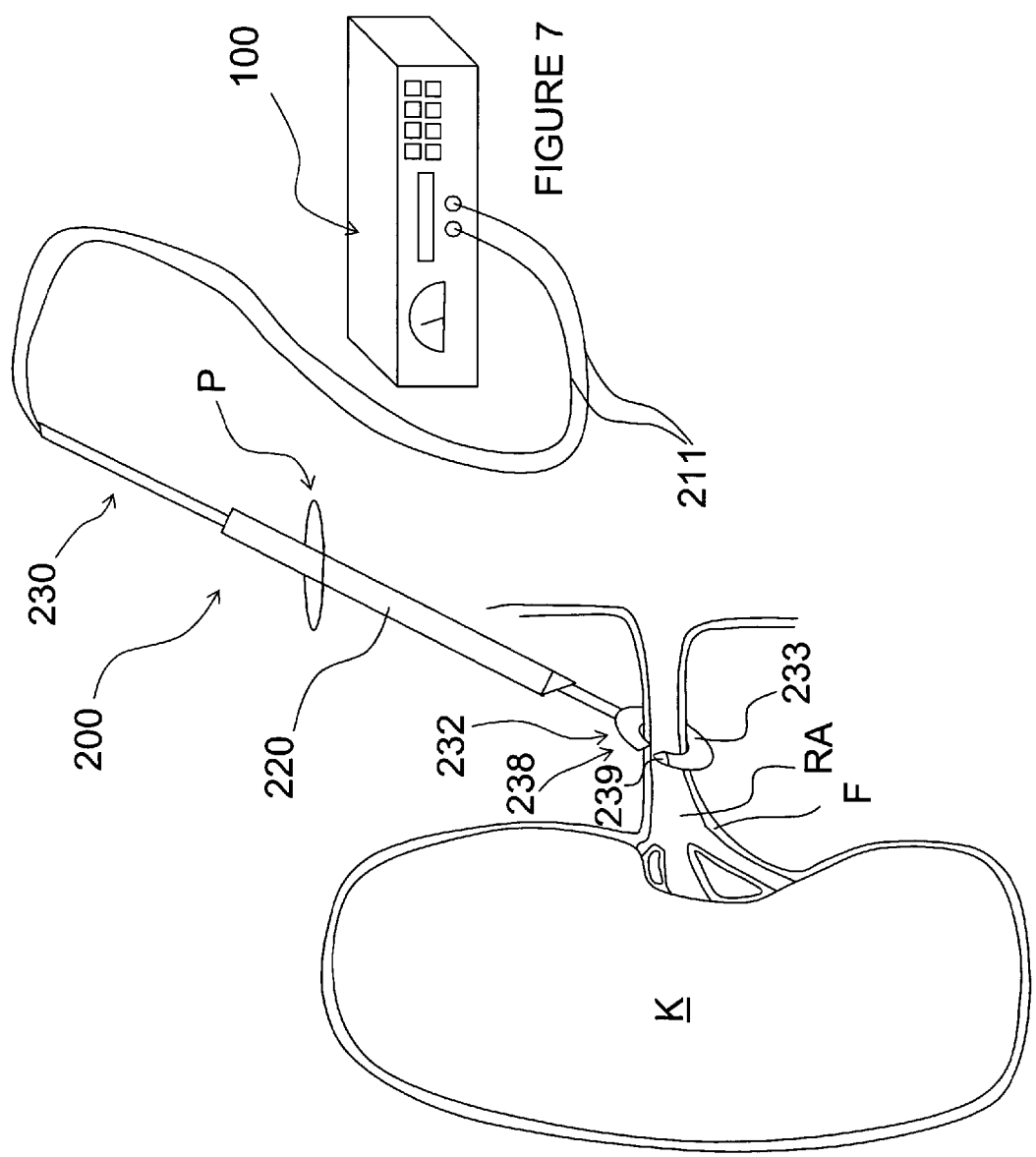

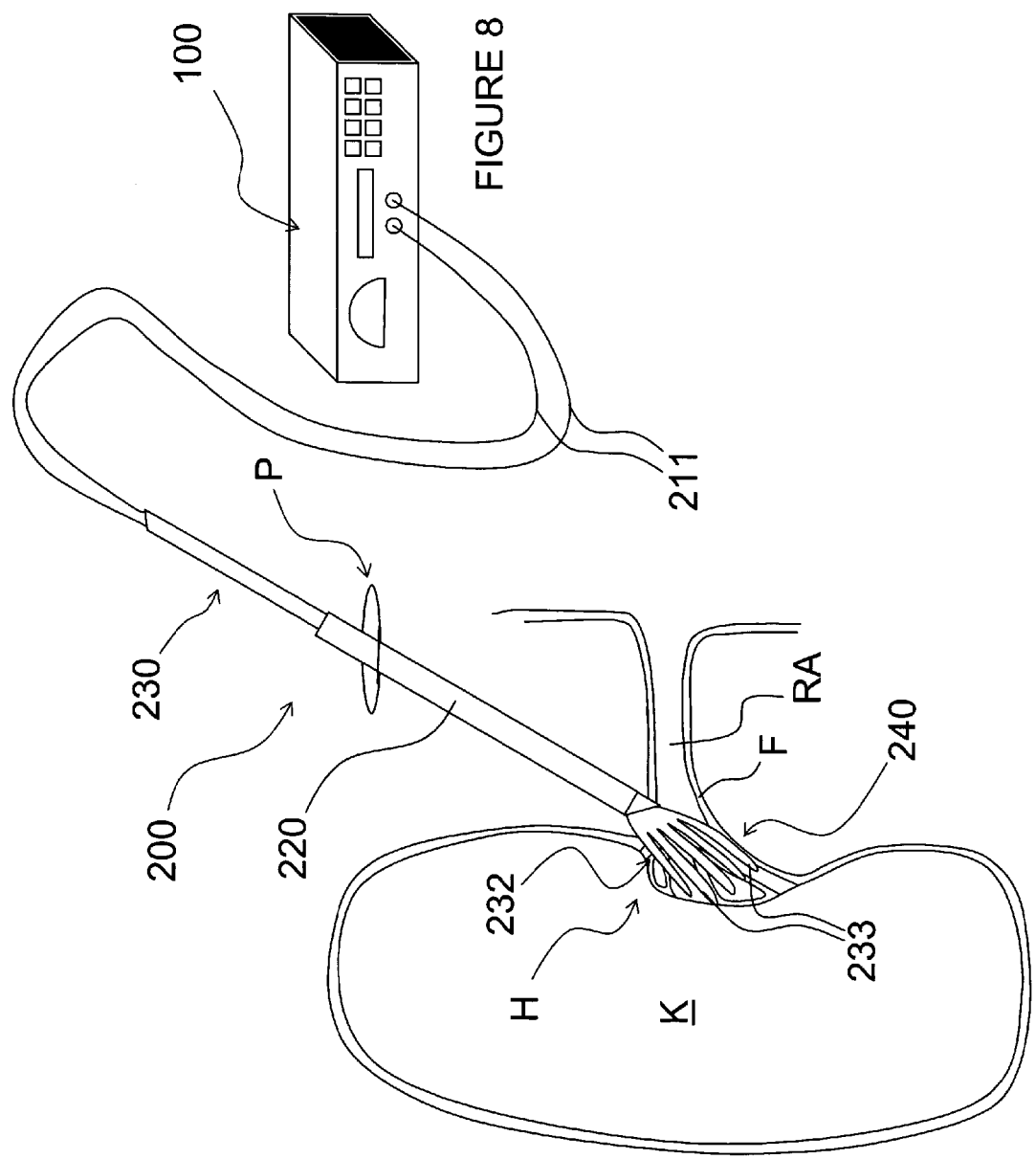

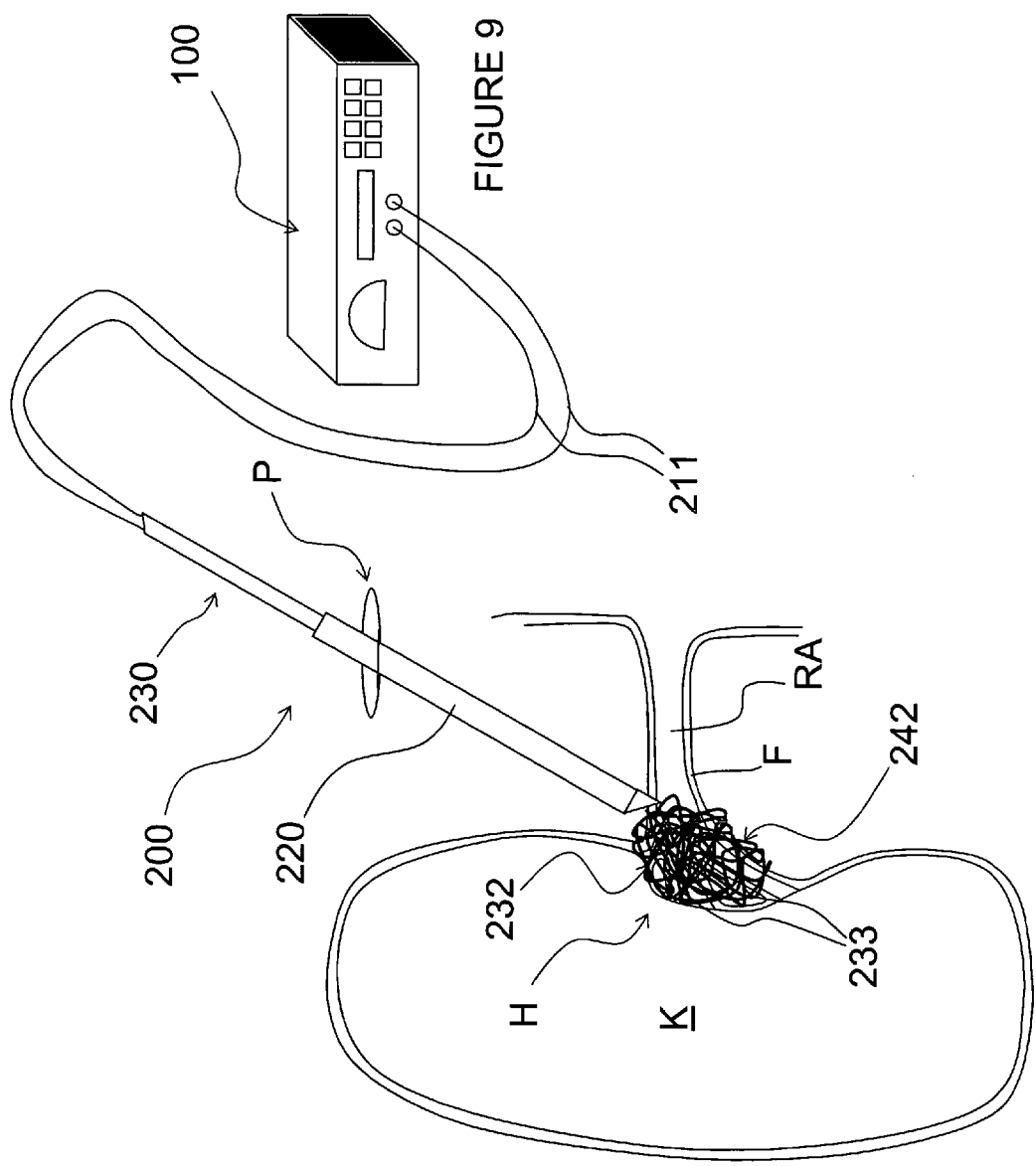

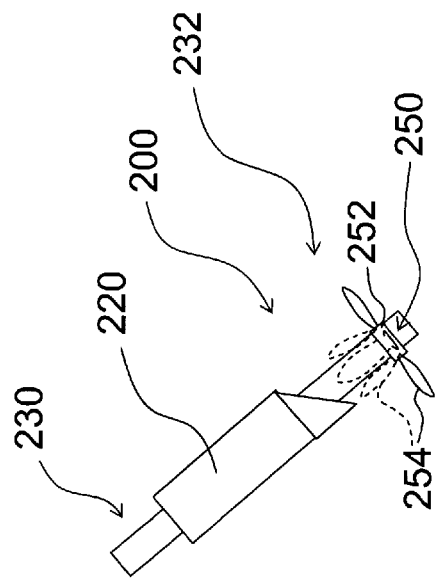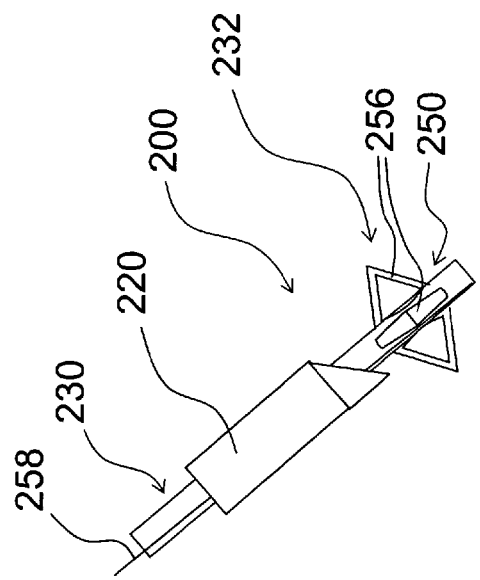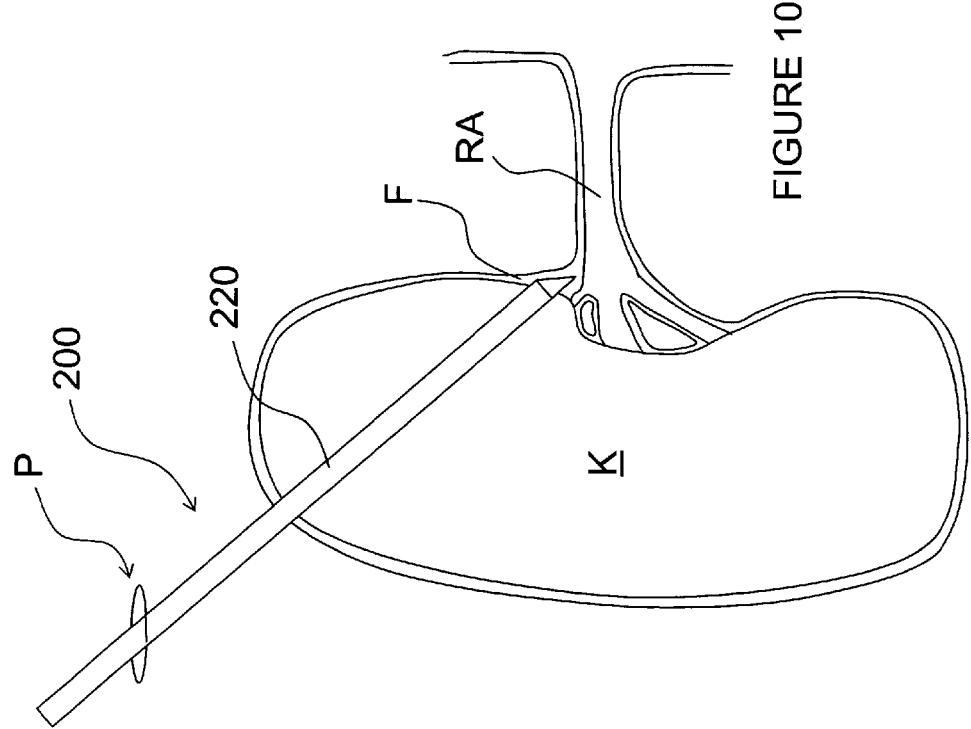

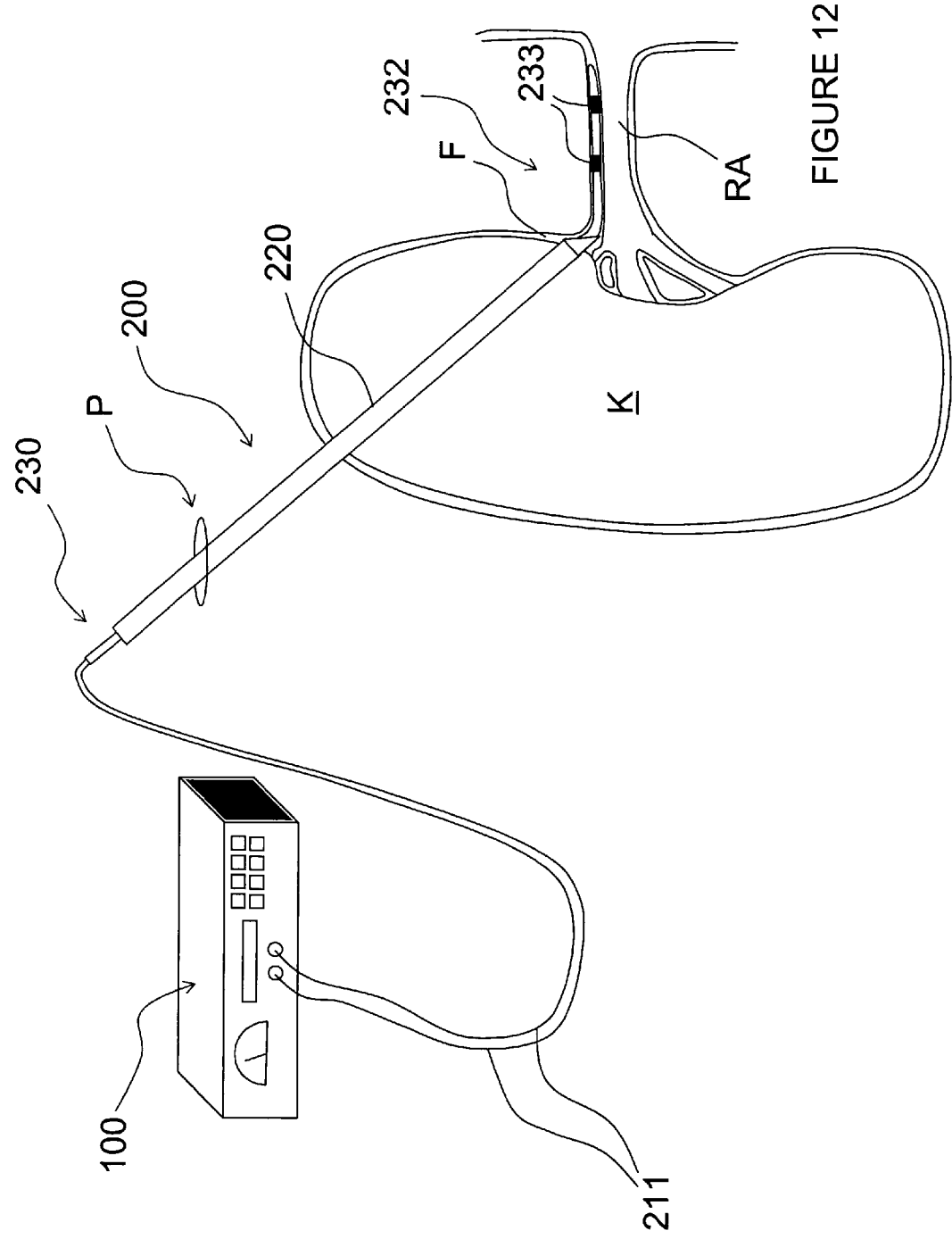

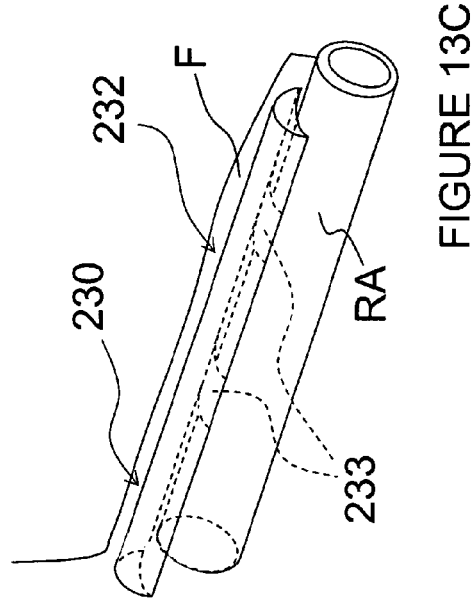
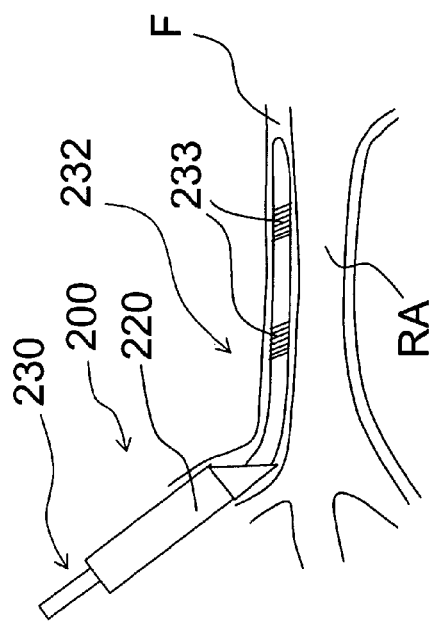
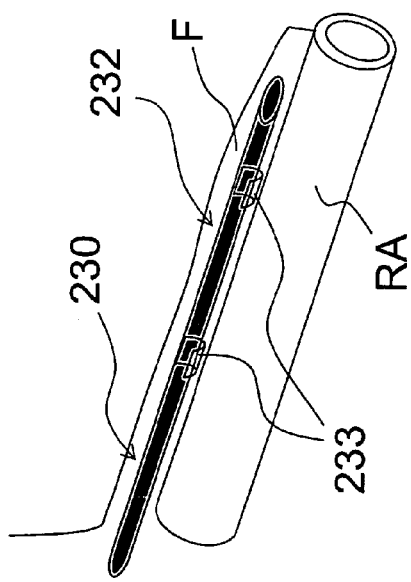
FIGURE 13A
FIGURE 13B
FIGURE 13C

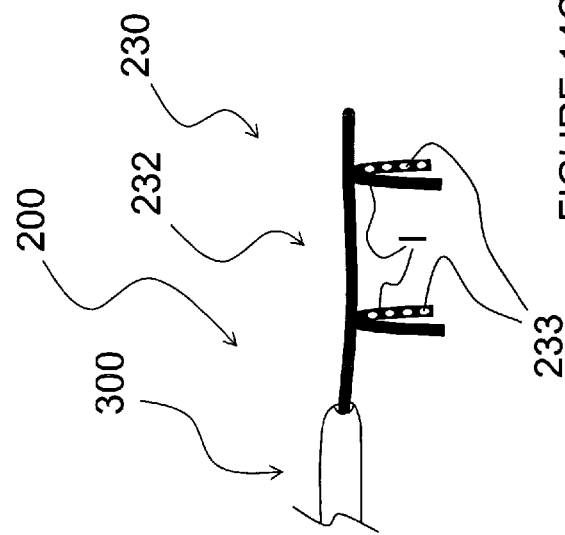
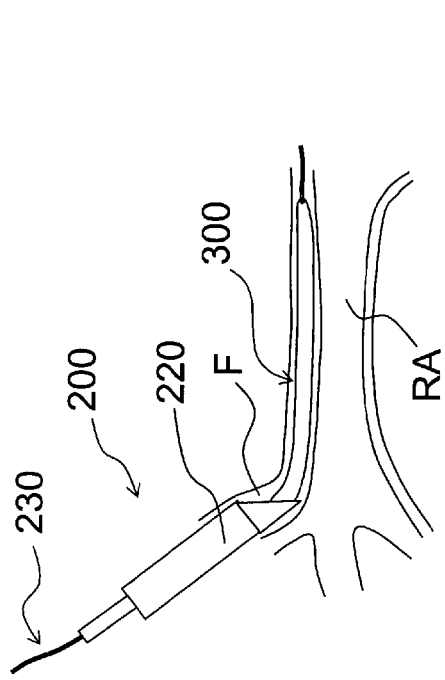
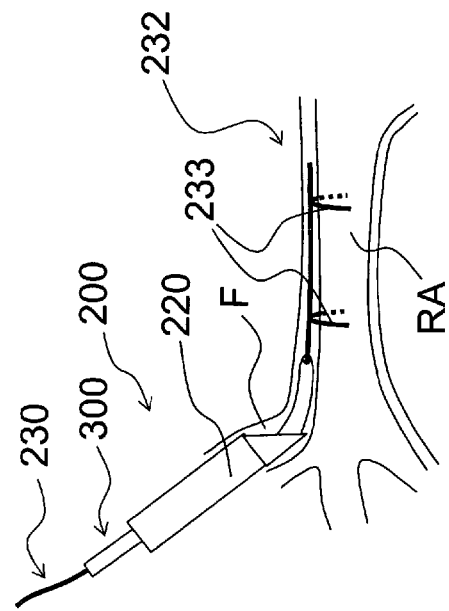

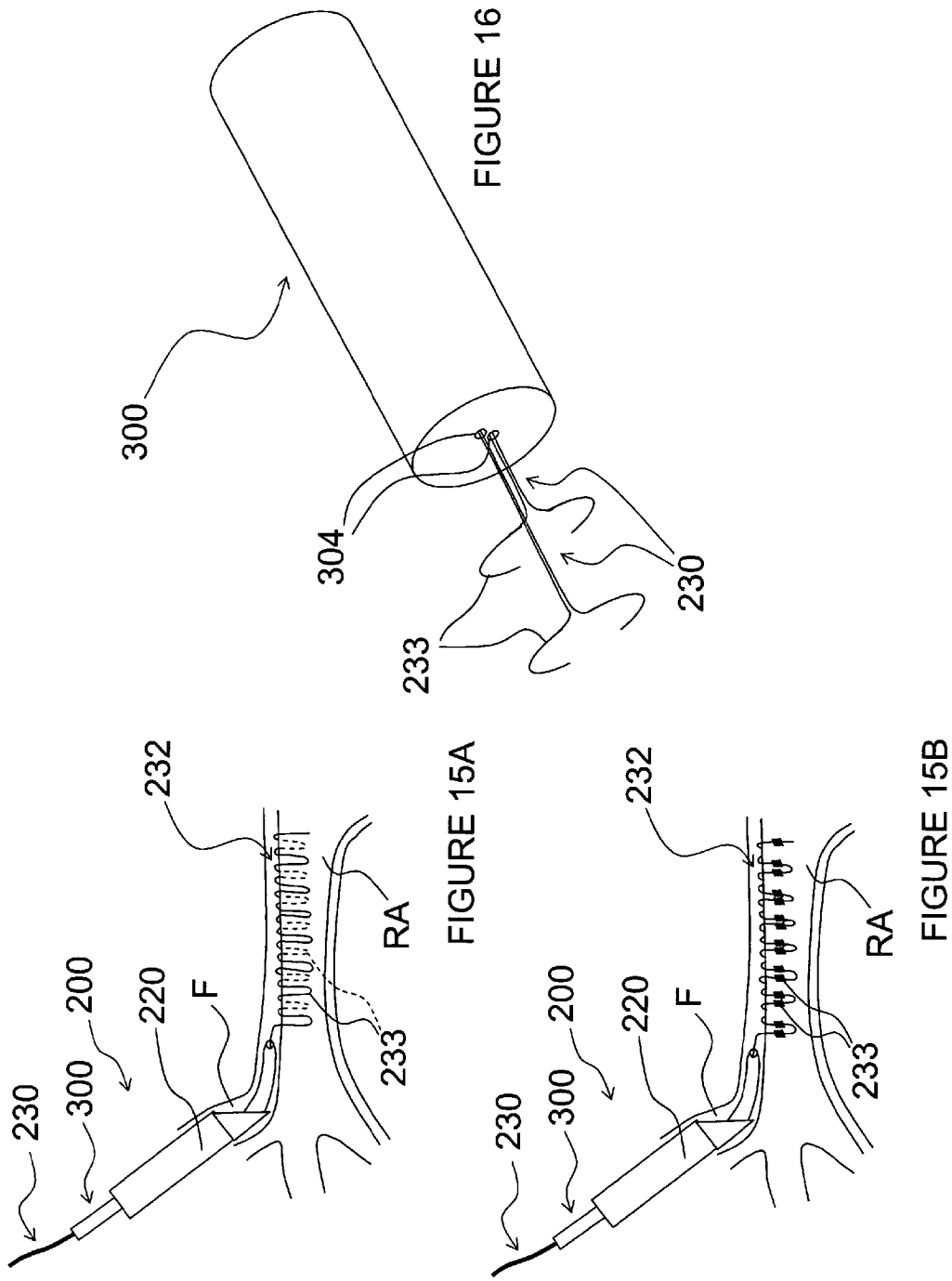

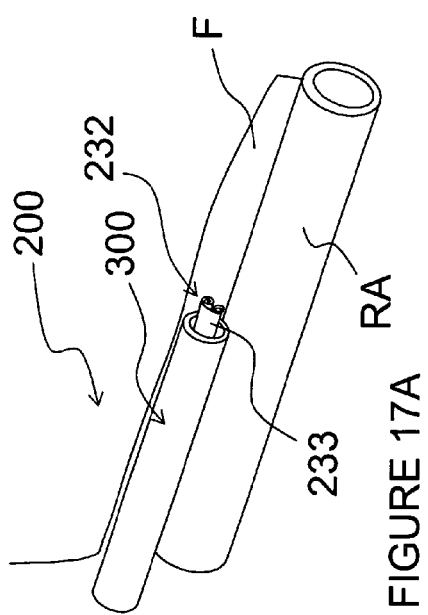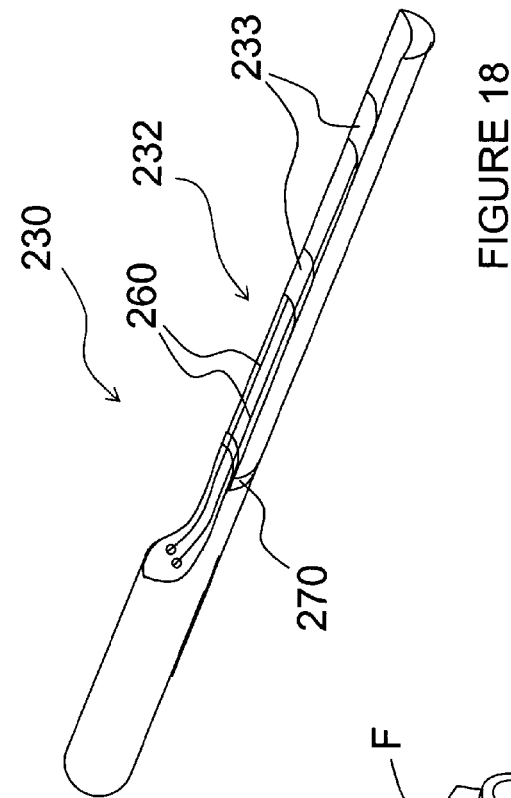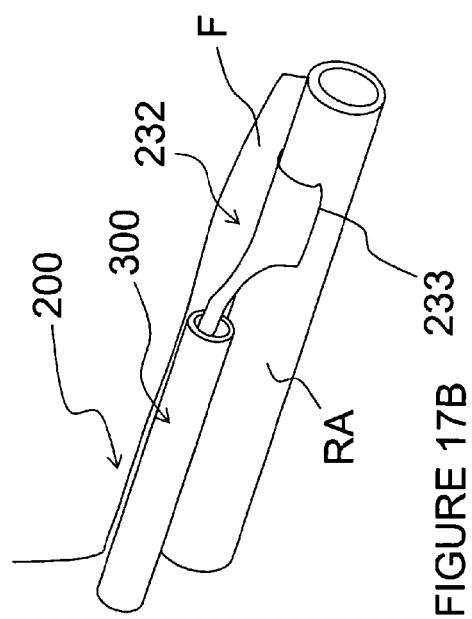

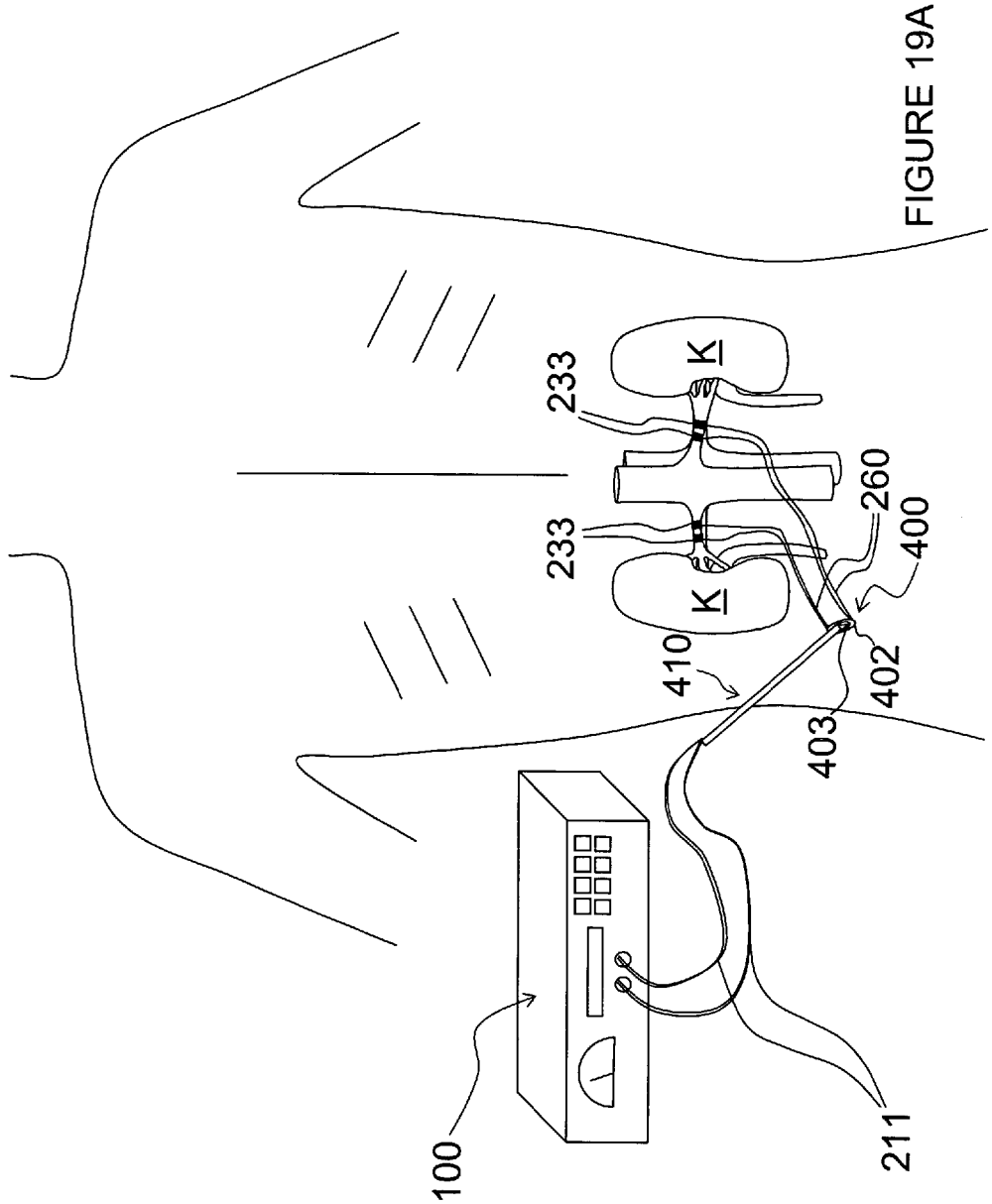

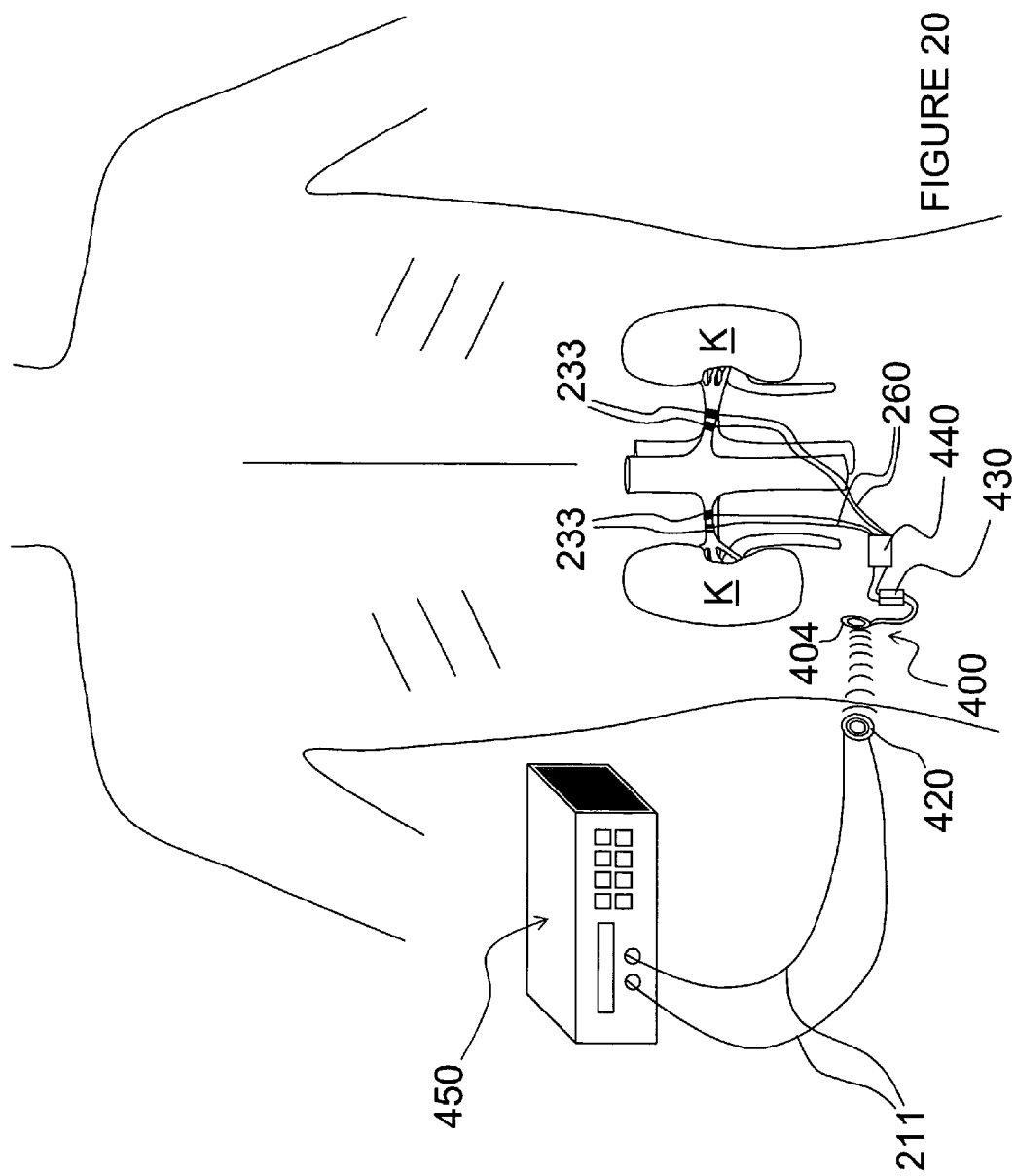

METHODS FOR RENAL NEUROMODULATION

CROSS-REFERENCE TO RELATED APPLICATION(S)

This application is a continuation of U.S. patent application Ser. No. 14/878,898, filed on Oct. 8, 2015, now U.S. Pat. No. 9,463,066, which is a continuation of U.S. patent application Ser. No. 14/279,023, filed on May 15, 2014, now U.S. Pat. No. 9,186,213, which is a continuation of U.S. patent application Ser. No. 13/942,223, filed on Jul. 15, 2013, now U.S. Pat. No. 9,072,527, which is a continuation of U.S. patent application Ser. No. 13/361,542, filed on Jan. 30, 2012, now abandoned, which is a divisional of U.S. patent application Ser. No. 11/189,563, filed on Jul. 25, 2005, now U.S. Pat. No. 8,145,316, which is a continuation-in-part of U.S. patent application Ser. No. 11/129,765, filed on May 13, 2005, now U.S. Pat. No. 7,653,438, which claims the benefit of U.S. Provisional Patent Application Ser. No. 60/616,254, filed Oct. 5, 2004; and U.S. Provisional Patent Application Ser. No. 60/624,793, filed Nov. 2, 2004, all of which are incorporated herein by reference in their entireties. Furthermore, U.S. patent application Ser. No. 11/189,563, now U.S. Pat. No. 8,145,316, is also a continuation-in-part of U.S. patent application Ser. No. 10/900,199, filed Jul. 28, 2004, now U.S. Pat. No. 6,978,174, and U.S. patent application Ser. No. 10/408,665, filed Apr. 8, 2003, now U.S. Pat. No. 7,162,303; both of which claim the benefit of U.S. Provisional Patent Application Ser. No. 60/370,190, filed Apr. 8, 2002; U.S. Provisional Patent Application Ser. No. 60/415,575, filed Oct. 3, 2002; and U.S. Provisional Patent Application Ser. No. 60/442,970, filed Jan. 29, 2003, all of which are incorporated herein by reference in their entireties.

INCORPORATION BY REFERENCE

All publications and patent applications mentioned in this specification are herein incorporated by reference to the same extent as if each individual publication or patent application was specifically and individually' indicated to be incorporated by reference.

TECHNICAL FIELD

The present invention relates to methods and apparatus for renal neuromodulation. More particularly, the present invention relates to methods and apparatus for achieving renal neuromodulation via a pulsed electric field and/or electroporation or electrofusion.

BACKGROUND

Congestive Heart Failure ("CHF") is a condition that occurs when the heart becomes damaged and reduces blood flow to the organs of the body. If blood flow decreases sufficiently, kidney function becomes impaired and results in fluid retention, abnormal hormone secretions and increased constriction of blood vessels. These results increase the workload of the heart and further decrease the capacity of the heart to pump blood through the kidney and circulatory system.

This reduced capacity further reduces blood flow to the kidney. It is believed that progressively decreasing perfusion of the kidney is a principal non-cardiac cause perpetuating the downward spiral of CHF. Moreover, the fluid overload and associated clinical symptoms resulting from these physiologic changes are predominant causes for excessive hospital admissions, terrible quality of life and overwhelming costs to the health care system due to CHF.

While many different diseases may initially damage the heart, once present, CHF is split into two types: Chronic CHF and Acute (or Decompensated-Chronic) CHF. Chronic Congestive Heart Failure is a longer term, slowly progressive, degenerative disease. Over years, chronic congestive heart failure leads to cardiac insufficiency. Chronic CHF is clinically categorized by the patient's ability to exercise or perform normal activities of daily living (such as defined by the New York Heart Association Functional Class). Chronic CHF patients are usually managed on an outpatient basis, typically with drugs.

Chronic CHF patients may experience an abrupt, severe deterioration in heart function, termed Acute Congestive Heart Failure, resulting in the inability of the heart to maintain sufficient blood flow and pressure to keep vital organs of the body alive. These Acute CHF deteriorations can occur when extra stress (such as an infection or excessive fluid overload) significantly increases the workload on the heart in a stable chronic CHF patient. In contrast to the stepwise downward progression of chronic CHF, a patient suffering acute CHF may deteriorate from even the earliest stages of CHF to severe hemodynamic collapse. In addition, Acute CHF can occur within hours or days following an Acute Myocardial Infarction ("AMI"), which is a sudden, irreversible injury to the heart muscle, commonly referred to as a heart attack.

As mentioned, the kidneys play a significant role in the progression of CHF, as well as in Chronic Renal Failure ("CRF"), End-Stage Renal Disease ("ESRD"), hypertension (pathologically high blood pressure) and other cardio-renal diseases. The functions of the kidney can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions resulting from reduced renal function or renal failure (kidney failure) are believed to increase the workload of the heart. In a CHF patient, renal failure will cause the heart to further deteriorate as the water build-up and blood toxins accumulate due to the poorly functioning kidneys and, in turn, cause the heart further harm.

The primary functional unit of the kidneys that is involved in urine formation is called the "nephron." Each kidney consists of about one million nephrons. The nephron is made up of a glomerulus and its tubules, which can be separated into a number of sections: the proximal tubule, the medullary loop (loop of Henle), and the distal tubule. Each nephron is surrounded by different types of cells that have the ability to secrete several substances and hormones (such as renin and erythropoietin). Urine is formed as a result of a complex process starting with the filtration of plasma water from blood into the glomerulus. The walls of the glomerulus are freely permeable to water and small molecules but almost impermeable to proteins and large molecules. Thus, in a healthy kidney, the filtrate is virtually free of protein and has no cellular elements. The filtered fluid that eventually becomes urine flows through the tubules. The final chemical composition of the urine is determined by the secretion into, and re-absorption of substances from, the urine required to maintain homeostasis.

Receiving about 20% of cardiac output, the two kidneys filter about 125 ml of plasma water per minute. Filtration occurs because of a pressure gradient across the glomerular membrane. The pressure in the arteries of the kidney pushes plasma water into the glomerulus causing filtration. To keep the Glomerulur Filtration Rate ("GFR") relatively constant, pressure in the glomerulus is held constant by the constriction or dilatation of the afferent and efferent arterioles, the muscular walled vessels leading to and from each glomerulus.

In a CHF patient, the heart will progressively fail, and blood flow and pressure will drop in the patient's circulatory system. During acute heart failure, short-term compensations serve to maintain perfusion to critical organs, notably the brain and the heart that cannot survive prolonged reduction in blood flow. However, these same responses that initially aid survival during acute heart failure become deleterious during chronic heart failure.

A combination of complex mechanisms contribute to deleterious fluid overload in CHF. As the heart fails and blood pressure drops, the kidneys cannot function and become impaired due to insufficient blood pressure for perfusion. This impairment in renal function ultimately leads to the decrease in urine output. Without sufficient urine output, the body retains fluids, and the resulting fluid overload causes peripheral edema (swelling of the legs), shortness of breath (due to fluid in the lungs), and fluid retention in the abdomen, among other undesirable conditions in the patient.

In addition, the decrease in cardiac output leads to reduced renal blood flow, increased neurohormonal stimulus, and release of the hormone renin from the juxtaglomerular apparatus of the kidney. This results in avid retention of sodium and, thus, volume expansion. Increased renin results in the formation of angiotensin, a potent vasoconstrictor. Heart failure and the resulting reduction in blood pressure also reduce the blood flow and perfusion pressure through organs in the body other than the kidneys. As they suffer reduced blood pressure, these organs may become hypoxic, resulting in a metabolic acidosis that reduces the effectiveness of pharmacological therapy and increases a risk of sudden death.

This spiral of deterioration that physicians observe in heart failure patients is believed to be mediated, at least in part, by activation of a subtle interaction between heart function and kidney function, known as the renin-angiotensin system. Disturbances in the heart's pumping function results in decreased cardiac output and diminished blood flow. The kidneys respond to the diminished blood flow as though the total blood volume was decreased, when in fact the measured volume is normal or even increased. This leads to fluid retention by the kidneys and formation of edema, thereby causing the fluid overload and increased stress on the heart Systemically, CHF is associated with an abnormally elevated peripheral vascular resistance and is dominated by alterations of the circulation resulting from an intense disturbance of sympathetic nervous system function. Increased activity of the sympathetic nervous system promotes a downward vicious cycle of increased arterial vasoconstriction (increased resistance of vessels to blood flow) followed by a further reduction of cardiac output, causing even more diminished blood flow to the vital organs.

In CHF via the previously explained mechanism of vasoconstriction, the heart and circulatory system dramatically reduce blood flow to the kidneys. During CHF, the kidneys receive a command from higher neural centers via neural pathways and hormonal messengers to retain fluid and sodium in the body. In response to stress on the heart, the neural centers command the kidneys to reduce their filtering functions. While in the short term, these commands can be beneficial, if these commands continue over hours and days they can jeopardize the person's life or make the person dependent on artificial kidney for life by causing the kidneys to cease functioning.

When the kidneys do not fully filter the blood, a huge amount of fluid is retained in the body, which results in bloating (fluid retention in tissues) and increases the workload of the heart. Fluid can penetrate into the lungs, and the patient becomes short of breath. This odd and self-destructive phenomenon is most likely explained by the effects of normal compensatory mechanisms of the body that improperly perceive the chronically low blood pressure of CHF as a sign of temporary disturbance, such as bleeding.

In an acute situation, the body tries to protect its most vital organs, the brain and the heart, from the hazards of oxygen deprivation. Commands are issued via neural and hormonal pathways and messengers. These commands are directed toward the goal of maintaining blood pressure to the brain and heart, which are treated by the body as the most vital organs. The brain and heart cannot sustain low perfusion for any substantial period of time. A stroke or a cardiac arrest will result if the blood pressure to these organs is reduced to unacceptable levels. Other organs, such as the kidneys, can withstand somewhat longer periods of ischemia without suffering long-term damage. Accordingly, the body sacrifices blood supply to these other organs in favor of the brain and the heart.

The hemodynamic impairment resulting from CHF activates several neurohormonal systems, such as the renin-angiotensin and aldosterone system, sympatho-adrenal system and vasopressin release. As the kidneys suffer from increased renal vasoconstriction, the GFR drops, and the sodium load in the circulatory system increases. Simultaneously, more renin is liberated from the juxtaglomerular of the kidney. The combined effects of reduced kidney functioning include reduced glomerular sodium load, an aldosterone-mediated increase in tubular reabsorption of sodium, and retention in the body of sodium and water. These effects lead to several signs and symptoms of the CHF condition, including an enlarged heart, increased systolic wall stress, an increased myocardial oxygen demand, and the formation of edema on the basis of fluid and sodium retention in the kidney. Accordingly, sustained reduction in renal blood flow and vasoconstriction is directly responsible for causing the fluid retention associated with CHF.

CHF is progressive, and as of now, not curable. The limitations of drug therapy and its inability to reverse or even arrest the deterioration of CHF patients are clear. Surgical therapies are effective in some cases, but limited to the end-stage patient population because of the associated risk and cost. Furthermore, the dramatic role played by kidneys in the deterioration of CHF patients is not adequately addressed by current surgical therapies.

The autonomic nervous system is recognized as an important pathway for control signals that are responsible for the regulation of body functions critical for maintaining vascular fluid balance and blood pressure. The autonomic nervous system conducts information in the form of signals from the body's biologic sensors such as baroreceptors (responding to pressure and volume of blood) and chemoreceptors (responding to chemical composition of blood) to the central nervous system via its sensory fibers. It also conducts command signals from the central nervous system that control the various innervated components of the vascular system via its motor fibers.

Experience with human kidney transplantation provided early evidence of the role of the nervous system in kidney function. It was noted that after transplant, when all the kidney nerves were totally severed, the kidney increased the excretion of water and sodium. This phenomenon was also observed in animals when the renal nerves were cut or chemically destroyed. The phenomenon was called "denervation diuresis" since the denervation acted on a kidney similar to a diuretic medication. Later the "denervation diuresis" was found to be associated with vasodilatation of the renal arterial system that led to increased blood flow through the kidney. This observation was confirmed by the observation in animals that reducing blood pressure supplying the kidneys reversed the "denervation diuresis."

It was also observed that after several months passed after the transplant surgery in successful cases, the "denervation diuresis" in transplant recipients stopped and the kidney function returned to normal. Originally, it was believed that the "renal diuresis" was a transient phenomenon and that the nerves conducting signals from the central nervous system to the kidney were not essential to kidney function. Later discoveries suggested that the renal nerves had a profound ability to regenerate and that the reversal of "denervation diuresis" could be attributed to the growth of new nerve fibers supplying the kidneys with necessary stimuli.

Another body of research focused on the role of the neural control of secretion of the hormone renin by the kidney. As was discussed previously, renin is a hormone responsible for the "vicious cycle" of vasoconstriction and water and sodium retention in heart failure patients. It was demonstrated that an increase or decrease in renal sympathetic nerve activity produced parallel increases and decreases in the renin secretion rate by the kidney, respectively.

In summary, it is known from clinical experience and the large body of animal research that an increase in renal sympathetic nerve activity leads to vasoconstriction of blood vessels supplying the kidney, decreased renal blood flow, decreased removal of water and sodium from the body, and increased renin secretion. It is also known that reduction of sympathetic renal nerve activity, e.g., via denervation, may reverse these processes.

It has been established in animal models that the heart failure condition results in abnormally high sympathetic stimulation of the kidney. This phenomenon was traced back to the sensory nerves conducting signals from baroreceptors to the central nervous system. Baroreceptors are present in the different locations of the vascular system. Powerful relationships exist between baroreceptors in the carotid arteries (supplying the brain with arterial blood) and sympathetic nervous stimulus to the kidneys. When arterial blood pressure was suddenly reduced in experimental animals with heart failure, sympathetic tone increased. Nevertheless, the normal baroreflex likely is not solely responsible for elevated renal nerve activity in chronic CHF patients. If exposed to a reduced level of arterial pressure for a prolonged time, baroreceptors normally "reset," i.e., return to a baseline level of activity, until a new disturbance is introduced. Therefore, it is believed that in chronic CHF patients, the components of the autonomic-nervous system responsible for the control of blood pressure and the neural control of the kidney function become abnormal. The exact mechanisms that cause this abnormality are not fully understood, but its effects on the overall condition of the CHF patients are profoundly negative.

End-Stage Renal Disease is another condition at least partially controlled by renal neural activity. There has been a dramatic increase in patients with ESRD due to diabetic nephropathy, chronic glomerulonephritis and uncontrolled hypertension. Chronic Renal Failure slowly progresses to ESRD. CRF represents a critical period in the evolution of ESRD. The signs and symptoms of CRF are initially minor, but over the course of 2-5 years, become progressive and irreversible. While some progress has been made in combating the progression to, and complications of, ESRD, the clinical benefits of existing interventions remain limited.

It has been known for several decades that renal diseases of diverse etiology (hypotension, infection, trauma, autoimmune disease, etc.) can lead to the syndrome of CRF characterized by systemic hypertension, proteinuria (excess protein filtered from the blood into the urine) and a progressive decline in GFR ultimately resulting in ESRD. These observations suggest that CRF progresses via a common pathway of mechanisms and that therapeutic interventions inhibiting this common pathway may be successful in slowing the rate of progression of CRF irrespective of the initiating cause.

To start the vicious cycle of CRF, an initial insult to the kidney causes loss of some nephrons. To maintain normal GFR, there is an activation of compensatory renal and systemic mechanisms resulting in a state of hyperfiltration in the remaining nephrons. Eventually, however, the increasing numbers of nephrons "overworked" and damaged by hyperfiltration are lost. At some point, a sufficient number of nephrons are lost so that normal GFR can no longer be maintained. These pathologic changes of CRF produce worsening systemic hypertension, thus high glomerular pressure and increased hyperfiltration. Increased glomerular hyperfiltration and permeability in CRF pushes an increased amount of protein from the blood, across the glomerulus and into the renal tubules. This protein is directly toxic to the tubules and leads to further loss of nephrons, increasing the rate of progression of CRF. This vicious cycle of CRF continues as the GFR drops with loss of additional nephrons leading to further hyperfiltration and eventually to ESRD requiring dialysis. Clinically, hypertension and excess protein filtration have been shown to be two major determining factors in the rate of progression of CRF to ESRD.

Though previously clinically known, it was not until the 1980s that the physiologic link between hypertension, proteinuria, nephron loss and CRF was identified. In the 1990s the role of sympathetic nervous system activity was elucidated. Afferent signals arising from the damaged kidneys due to the activation of mechanoreceptors and chemoreceptors stimulate areas of the brain responsible for blood pressure control. In response, the brain increases sympathetic stimulation on the systemic level, resulting in increased blood pressure primarily through vasoconstriction of blood vessels. When elevated sympathetic stimulation reaches the kidney via the efferent sympathetic nerve fibers, it produces major deleterious effects in two forms. The kidneys are damaged by direct renal toxicity from the release of sympathetic neurotransmitters (such as norepinephrine) in the kidneys independent of the hypertension. Furthermore, secretion of renin that activates Angiotensin II is increased, which increases systemic vasoconstriction and exacerbates hypertension.

Over time, damage to the kidneys leads to a further increase of afferent sympathetic signals from the kidney to the brain. Elevated Angiotensin II further facilitates internal renal release of neurotransmitters. The feedback loop is therefore closed, which accelerates deterioration of the kidneys.

In view of the foregoing, it would be desirable to provide methods and apparatus for the treatment of congestive heart failure, renal disease, hypertension and/or other cardio-renal diseases via renal neuromodulation and/or denervation.

SUMMARY

The present invention provides methods and apparatus for renal neuromodulation (e.g., denervation) using a pulsed electric field (PEF). Several aspects of the invention apply a pulsed electric field to effectuate electroporation and/or electrofusion in renal nerves, other neural fibers that contribute to renal neural function, or other neural features. Several embodiments of the invention are extravascular devices for inducing renal neuromodulation. The apparatus and methods described herein may utilize any suitable electrical signal or field parameters that achieve neuromodulation, including denervation, and/or otherwise create an electroporative and/or electrofusion effect. For example, the electrical signal may incorporate a nanosecond pulsed electric field (nsPEF) and/or a PEF for effectuating electroporation. One specific embodiment comprises applying a first course of PEF electroporation followed by a second course of nsPEF electroporation to induce apoptosis in any cells left intact after the PEF treatment, or vice versa. An alternative embodiment comprises fusing nerve cells by applying a PEF in a manner that is expected to reduce or eliminate the ability of the nerves to conduct electrical impulses. When the methods and apparatus are applied to renal nerves and/or other neural fibers that contribute to renal neural functions, the inventors of the present invention believe that urine output will increase, renin levels will decrease, urinary sodium excretion will increase and/or blood pressure will be controlled in a manner that will prevent or treat CHF, hypertension, renal system diseases, and other renal anomalies.

Several aspects of particular embodiments can achieve such results by selecting suitable parameters for the PEFs and/or nsPEFs. Pulsed electric field parameters can include, but are not limited to, field strength, pulse width, the shape of the pulse, the number of pulses and/or the interval between pulses (e.g., duty cycle). Suitable field strengths include, for example, strengths of up to about 10,000 V/cm. Suitable pulse widths include, for example, widths of up to about 1 second. Suitable shapes of the pulse waveform include, for example, AC waveforms, sinusoidal waves, cosine waves, combinations of sine and cosine waves, DC waveforms, DC-shifted AC waveforms, RF waveforms, square waves, trapezoidal waves, exponentially-decaying waves, combinations thereof, etc. Suitable numbers of pulses include, for example, at least one pulse. Suitable pulse intervals include, for example, intervals less than about 10 seconds. Any combination of these parameters may be utilized as desired. These parameters are provided for the sake of illustration and should in no way be considered limiting. Additional and alternative waveform parameters will be apparent.

Several embodiments are directed to extravascular systems for providing longlasting denervation to minimize acute myocardial infarct ("AMI") expansion and for helping to prevent the onset of morphological changes that are affiliated with congestive heart failure. For example, one embodiment of the invention comprises treating a patient for an infarction, e.g., via coronary angioplasty and/or stenting, and performing an extravascular pulsed electric field renal denervation procedure under, for example, Computed Tomography ("CT") guidance. PEF therapy can, for example, be delivered in a separate session soon after the AMI has been stabilized. Renal neuromodulation also may be used as an adjunctive therapy to renal surgical procedures. In these embodiments, the anticipated increase in urine output, decrease in renin levels, increase in urinary sodium excretion and/or control of blood pressure provided by the renal PEF therapy is expected to reduce the load on the heart to inhibit expansion of the infarct and prevent CHF.

Several embodiments of extravascular pulsed electric field systems described herein may denervate or reduce the activity of the renal nervous supply immediately post-infarct, or at any time thereafter, without leaving behind a permanent implant in the patient. These embodiments are expected to increase urine output, decrease renin levels, increase urinary sodium excretion and/or control blood pressure for a period of several months during which the patient's heart can heal. If it is determined that repeat and/or chronic neuromodulation would be beneficial after this period of healing, renal PEF treatment can be repeated as needed and/or a permanent implant may be provided.

In addition to efficaciously treating AMI, several embodiments of systems described herein are also expected to treat CHF, hypertension, renal failure, and other renal or cardio-renal diseases influenced or affected by increased renal sympathetic nervous activity. For example, the systems may be used to treat CHF at any time by extravascularly advancing the PEF system to a treatment site, for example, under CT-guidance. Once properly positioned, a PEF therapy may be delivered to the treatment site. This may, for example, modify a level of fluid offload.

The use of PEF therapy for the treatment of CHF, hypertension, end-stage renal disease and other cardio-renal diseases is described in detail hereinafter in several different extravascular system embodiments. The systems can be introduced into the area of the renal neural tissue under, for example, CT, ultrasonic, angiographic or laparoscopic guidance, or the systems can be surgically implanted using a combination of these or other techniques. The various elements of the system may be placed in a single operative session, or in two or more staged sessions. For instance, a percutaneous therapy might be conducted under CT or CTI/angiographic guidance. For a partially or fully implantable system, a combination of CT, angiographic or laparoscopic implantation of leads and nerve contact elements might be paired with a surgical implantation of the subcutaneous contact element or control unit. The systems may be employed unilaterally or bilaterally as desired for the intended clinical effect. The systems can be used to modulate efferent or afferent nerve signals, as well as combinations of efferent and afferent signals.

In one variation, PEF therapy is delivered at a treatment site to create a nonthermal nerve block, reduce neural signaling, or otherwise modulate neural activity. Alternatively or additionally, cooling, cryogenic, pulsed RF, thermal RF, thermal or nonthermal microwave, focused or unfocused ultrasound, thermal or non-thermal DC, as well as any combination thereof, may be employed to reduce or otherwise control neural signaling.

Several embodiments of the PEF systems may completely block or denervate the target neural structures, or the PEF systems may otherwise modulate the renal nervous activity. As opposed to a full neural blockade such as denervation, other neuromodulation produces a less-than-complete change in the level of renal nervous activity between the kidney(s) and the rest of the body. Accordingly, varying the pulsed electric field parameters will produce different effects on the nervous activity.

Any of the embodiments of the present invention described herein optionally may be configured for infusing agents into the treatment area before, during or after energy application. The infused agents may create a working space for introduction of PEF system elements, such as electrodes. Additionally or alternatively, the infused agents may be selected to enhance or modify the neuromodulatory effect of the energy application. The agents also may protect or temporarily displace non-target cells, and/or facilitate visualization.

Several embodiments of the present invention may comprise detectors or other elements that facilitate identification of locations for treatment and/or that measure or confirm the success of treatment. For example, temporary nerve-block agents, such as lidocaine, bupivacaine or the like, might be infused through a percutaneous needle injection or through an infusion port built into a partially or fully implantable system to ensure proper location of neural contact elements prior to delivering PEF therapy. Alternatively or additionally, the system can be configured to also deliver stimulation waveforms and monitor physiological parameters known to respond to stimulation of the renal nerves. Based on the results of the monitored parameters, the system can determine the location of renal nerves and/or whether denervation has occurred. Detectors for monitoring of such physiological responses include, for example, Doppler elements, thermocouples, pressure sensors, and imaging modalities (e.g., fluoroscopy, intravascular ultrasound, etc.). Alternatively, electroporation may be monitored directly using, for example, Electrical Impedance Tomography ("EIT") or other electrical impedance measurements or sensors. Additional monitoring techniques and elements will be apparent. Such detector(s) may be integrated with the PEF systems or they may be separate elements.

In some embodiments, stimulation of the nerve plexus may be utilized to determine whether repeat therapy is required. For example, stimulation may be used to elicit a pain response from the renal nerves. If the patient senses this stimulation, then it is apparent that nerve conduction has returned, and repeat therapy is warranted. This method optionally may be built into any of the systems described hereinafter—percutaneous, partially implantable or fully implantable.

Still other specific embodiments include electrodes configured to align the electric field with the longer dimension of the target cells. For instance, nerve cells tend to be elongate structures with lengths that greatly exceed their lateral dimensions (e.g., diameter). By aligning an electric field so that the directionality of field propagation preferentially affects the longitudinal aspect of the cell rather than the lateral aspect of the cell, it is expected that lower field strengths can be used to kill or disable target cells. This is expected to conserve the battery life of implantable devices, reduce collateral effects on adjacent structures, and otherwise enhance the ability to modulate the neural activity of target cells.

Other embodiments of the invention are directed to applications in which the longitudinal dimensions of cells in tissues overlying or underlying the nerve are transverse (e.g., orthogonal or otherwise at an angle) with respect to the longitudinal direction of the nerve cells. Another aspect of these embodiments is to align the directionality of the PEF such that the field aligns with the longer dimensions of the target cells and the shorter dimensions of the non-target cells. More specifically, arterial smooth muscle cells are typically elongate cells which surround the arterial circumference in a generally spiraling orientation so that their longer dimensions are circumferential rather than running longitudinally along the artery. Nerves of the renal plexus, on the other hand, run along the outside of the artery generally in the longitudinal direction of the artery. Therefore, applying a PEF which is generally aligned with the longitudinal direction of the artery is expected to preferentially cause electroporation in the target nerve cells without affecting at least some of the non-target arterial smooth muscle cells to the same degree. This may enable preferential denervation of nerve cells (target cells) in the adventitia or periarterial region without affecting the smooth muscle cells of the vessel to an undesirable extent.

It should be understood that the PEF systems described in this application are not necessarily required to make physical contact with the tissue or neural fibers to be treated. Electrical energy, such as thermal RF energy and non-thermal pulsed RF, may be conducted to tissue to be treated from a short distance away from the tissue itself. Thus, it may be appreciated that "nerve contact" comprises both physical contact of a system element with the nerve, as well as electrical contact alone without physical contact, or as a combination of the two.

In one embodiment of an extravascular pulsed electric field system, a laparoscopic or percutaneous system is utilized. For example, a percutaneous probe may be inserted in proximity to the track of the renal neural supply along the renal artery or vein and/or within the Gerota's fascia, under, e.g., CT or radiographic guidance. Once properly positioned, pulsed electric field therapy may be applied to target neural fibers via the probe, after which the probe may be removed from the patient to conclude the procedure.

It is expected that such therapy would reduce or alleviate clinical symptoms of CHF, hypertension, renal disease and/or other cardio-renal diseases, for several months (e.g., potentially up to six months or' more). This time period might be sufficient to allow the body to heal, for example, this period might reduce a risk of CHF onset after an acute myocardial infarction, thereby alleviating a need for subsequent re-treatment. Alternatively, as symptoms reoccur, or at regularly scheduled intervals, the patient might return to the physician or self-administer a repeat therapy. As another alternative, repeat therapy might be fully automated.

The need for a repeat therapy optionally might be predicted by monitoring of physiologic parameters, for example, by monitoring specific neurohormones (plasma renin levels, etc.) that are indicative of increased sympathetic nervous activity. Alternatively, provocative maneuvers known to increase sympathetic nervous activity, such as head-out water immersion testing, may be conducted to determine the need for repeat therapy.

In addition or as an alternative to laparoscopic or percutaneous PEF systems, partially implantable PEF systems may be utilized. For example, an external control box may connect through or across the patient's skin to a subcutaneous element. Leads may be tunneled from the subcutaneous element to a nerve cuff or a nerve contact element in proximity to Gerota's fascia, the renal artery, vein and/or hilum. PEF therapy may be conducted from the external control box across or through the skin to the subcutaneous element and to the nerve cuff or nerve contact element to modulate neural fibers that contribute to renal function.

The PEF may be transmitted across or through the skin via direct methods, such as needles or trocars, or via indirect methods such as transcutaneous energy transfer ("TET")

systems. TET systems are used clinically to recharge batteries in rechargeable implantable stimulation or pacing devices, left ventricular assist devices, etc. In one TET embodiment of the present invention, the subcutaneous system may have a receiving coil to gather transmitted energy, a capacitor or temporary storage device to collect the charge, control electronics to create a waveform, as well as leads and nerve electrode(s) to deliver the energy waveform to the renal nerves.

In another TET embodiment, a PEF signal itself may be transmitted telemetrically through the skin to a subcutaneous receiving element. Passive leads connecting the subcutaneous receiving element to nerve electrodes may conduct the signal to the nerves for treatment, thereby eliminating a need for a receiving battery or capacitor, as well as signal processing circuitry, in the implanted portion of the PEF system.

In other partially implanted embodiments, the implanted subcutaneous elements may be entirely passive. The subcutaneous elements may include an implantable electrical connector that is easily accessible via a simple needle, leads to the nerve electrodes, and the nerve electrodes themselves. The implanted system might also incorporate an infusion lumen to allow drugs to be introduced from a subcutaneous port to the treatment area. A control box, a lead and a transcutaneous needle or trocar electrical connector may be disposed external to the patient.

In addition or as an alternative to non-implanted PEF systems, or partially implantable PEF systems, fully implantable PEF systems may be utilized. An implantable control housing containing signal generation circuitry and energy supply circuitry may be attached to leads which are tunneled to a renal nerve cuff or renal nerve contact electrodes. Power may be provided by a battery included with the implantable housing. The battery may, for example, require surgical replacement after a period of months or years, or may be rechargeable via a TET system. When therapy is required, a PEF signal is applied to the nerves using the contact electrodes, with the control housing serving as the return electrode.

The need for repeat therapy may be tested by the implantable system. For example, a lower-frequency stimulation signal may be applied to the nerves periodically by the system. When the nerve has returned toward baseline function, the test signal would be felt by the patient, and the system then would be instructed to apply another course of PEF therapy. This repeat treatment optionally might be patient or physician initiated. If the patient feels the test signal, the patient or physician might operate the implantable system via electronic telemetry, magnetic switching or other means to apply the required therapeutic PEF.

Alternatively, the system could be programmed in an open-loop fashion to apply another PEF treatment periodically, for example, once every six months. In still another embodiment, monitoring methods that assess parameters or symptoms of the patient's clinical status may be used to determine the need for repeat therapy.

The nerve contact elements of any of the percutaneous, partially implantable or fully implantable systems may comprise a variety of embodiments. For instance, the implanted elements might be in the form of a cuff, basket, cupped contact, fan-shaped contact, space-filling contact, spiral contact or the like. Implantable nerve contact elements may incorporate elements that facilitate anchoring and/or tissue in-growth. For instance, fabric or implantable materials such as Dacron or ePTFE might be incorporated into the design of the contact elements to facilitate in-growth into areas of the device that would help anchor the system in place, but repel tissue in-growth in undesired areas, such as the electrical contacts. Similarly, coatings, material treatments, drug coatings or drug elution might be used alone or in combination to facilitate or retard tissue in-growth into various segments of the implanted system as desired.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIG. 4 is a schematic view illustrating a percutaneous or laparoscopic method and apparatus for renal neuromodulation.

FIG. 6 is a schematic view illustrating a percutaneous or laparoscopic method and apparatus for renal neuromodulation comprising a spiral electrode configured to surround renal vasculature.

FIG. 7 is a schematic view illustrating a percutaneous or laparoscopic method and apparatus for renal neuromodulation comprising a ring electrode configured to at least partially surround renal vasculature.

FIG. 8 is a schematic view illustrating another percutaneous or laparoscopic method and apparatus for renal neuromodulation comprising a spreading electrode configured for positioning near the renal hilum.

FIG. 9 is a schematic view illustrating a percutaneous or laparoscopic method and apparatus for renal neuromodulation comprising a space-occupying electrode configured for positioning near the renal hilum.

FIG. 10 is a schematic view illustrating a percutaneous or laparoscopic method and apparatus for accessing Gerota's fascia.

FIGS. 11A and 11B are schematic views illustrating methods and apparatus for mechanically anchoring a delivery system or electrode within Gerota's fascia.

FIG. 12 is a schematic view illustrating a method and apparatus for positioning electrodes along a patient's renal artery within an annular space between the artery and Gerota's fascia in order to achieve renal neuromodulation.

FIGS. 13A-13C are schematic detail views of various embodiments of the electrodes of FIG. 12.

FIGS. 14A-14C are schematic views and a detail view illustrating another method and apparatus for positioning electrodes along the patient's renal artery.

FIGS. 15A and 15B are a schematic view and a detail view illustrating yet another method and apparatus for positioning electrodes.

FIG. 16 is a schematic view illustrating still another method and apparatus for positioning electrodes along the patient's renal artery.

FIGS. 17A and 17B are schematic views illustrating another method and apparatus for positioning electrodes along the patient's renal artery.

FIG. 18 is a schematic view illustrating a method and apparatus for positioning implantable electrodes along the patient's renal artery.

FIGS. 19A and 19B are schematic views illustrating methods and apparatus for renal neuromodulation via partially implantable systems.

FIG. 20 is a schematic view illustrating a method and apparatus for renal neuromodulation via a fully implantable system.

DETAILED DESCRIPTION

A. Overview

The present invention relates to methods and apparatus for renal neuromodulation and/or other neuromodulation. More particularly, the present invention relates to methods and apparatus for renal neuromodulation using a pulsed electric field to effectuate electroporation or electrofusion. As used herein, electroporation and electropermeabilization are methods of manipulating the cell membrane or intracellular apparatus. For example, short high-energy pulses cause pores to open in cell membranes. The extent of porosity in the cell membrane (e.g., size and number of pores) and the duration of the pores (e.g., temporary or permanent) are a function of the field strength, pulse width, duty cycle, field orientation, cell type and other parameters. In general, pores will generally close spontaneously upon termination of lower strength fields or shorter pulse widths (herein defined as "reversible electroporation"). Each cell type has a critical threshold above which pores do not close such that pore formation is no longer reversible; this result is defined as "irreversible electroporation," "irreversible breakdown" or "irreversible damage." At this point, the cell membrane ruptures and/or irreversible chemical imbalances caused by the high porosity occur. Such high porosity can be the result of a single large hole and/or a plurality of smaller holes. Certain types of electroporation energy parameters also appropriate for use in renal neuromodulation are high voltage pulses with a duration in the sub-microsecond range (nanosecond pulsed electric fields, or nsPEF) which may leave the cellular membrane intact, but alter the intracellular apparatus or function of the cell in ways which cause cell death or disruption. Certain applications of nsPEF have been shown to cause cell death by inducing apoptosis, or programmed cell death, rather than acute cell death. Also, the term "comprising" is used throughout to mean including at least the recited feature such that any greater number of the same feature and/or additional types features are not precluded.

Several embodiments of the present invention provide extravascular devices or systems for inducing renal neuromodulation, such as a temporary change in target nerves that dissipates over time, continuous control over neural function, and/or denervation. The apparatus and methods described herein may utilize any suitable electrical signal or field parameters, e.g., any electric field, that will achieve the desired neuromodulation (e.g., electroporative effect). To better understand the structures of the extravascular devices and the methods of using these devices for neuromodulation, it is useful to understand the renal anatomy in humans.

B. Selected Embodiments of Methods for Neuromodulation

Figure 1:
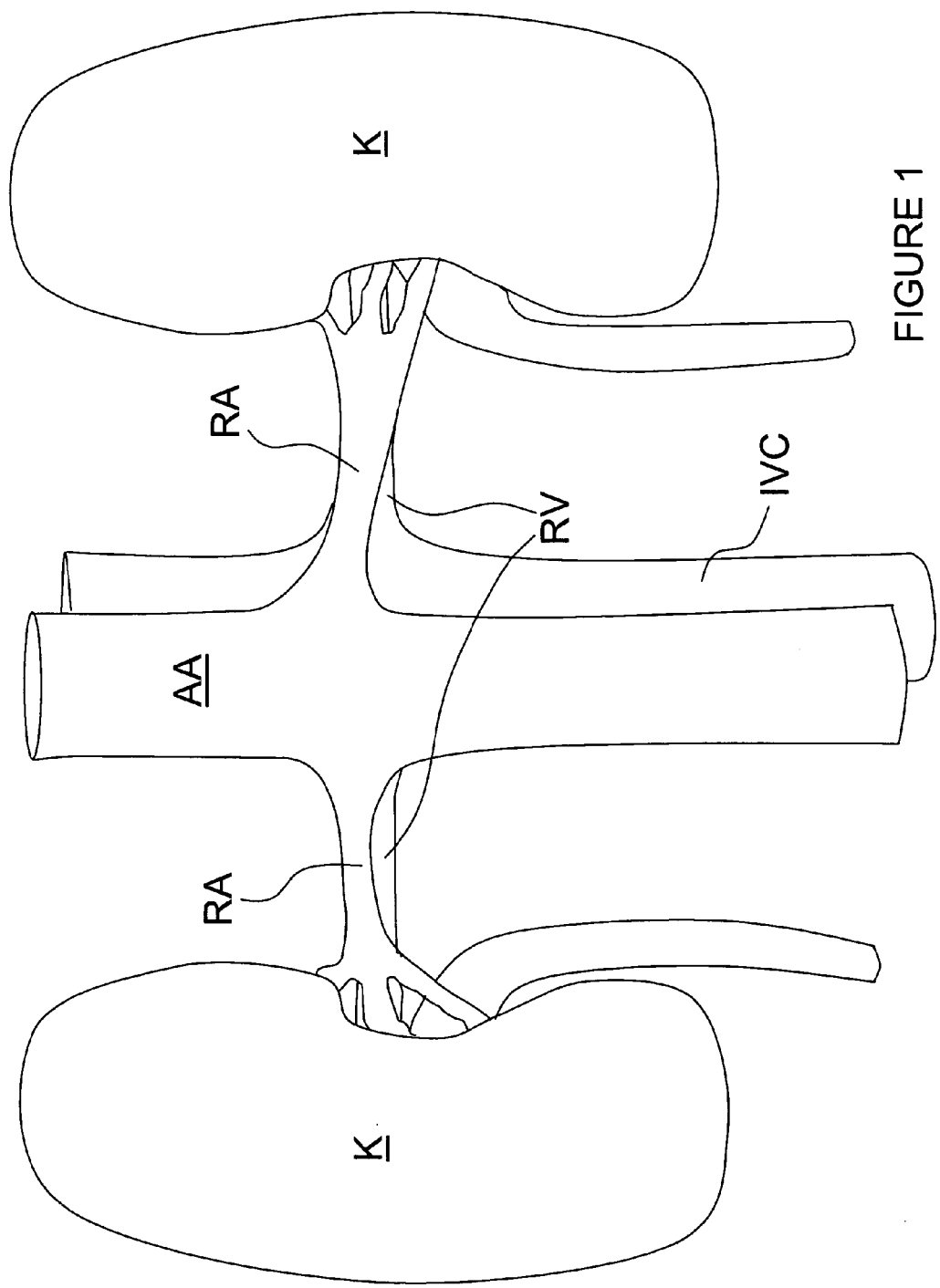
FIG. 1 is a schematic view illustrating human renal anatomy.
Figure 2:
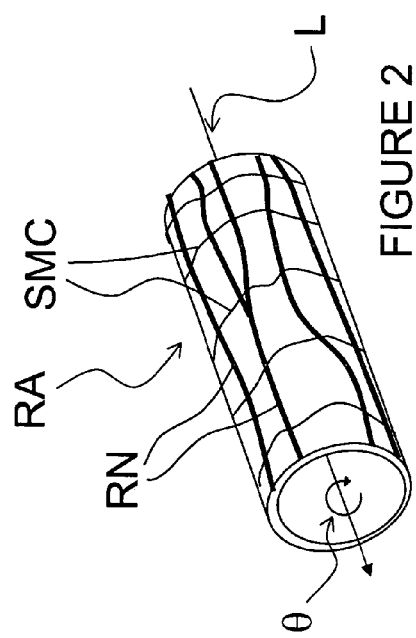
FIG. 2 is a schematic detail view showing the location of the renal nerves relative to the renal artery.

With reference now to FIG. 1, the human renal anatomy includes kidneys K that are supplied with oxygenated blood by renal arteries RA, which are connected to the heart by the abdominal aorta AA. Deoxygenated blood flows from the kidneys to the heart via renal veins RV and the inferior vena cava IVC. FIG. 2 illustrates a portion of the renal anatomy in greater detail. More specifically, the renal anatomy also includes renal nerves RN extending longitudinally along the lengthwise dimension L of renal artery RA generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
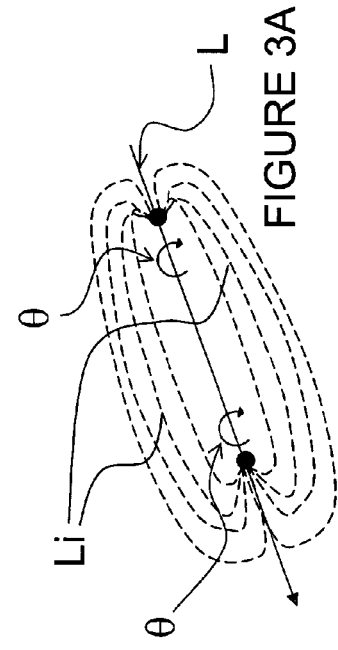
FIGS. 3A and 3B are schematic side- and end-views, respectively, illustrating a direction of electrical current flow for selectively affecting renal nerves.
Figure 3B:
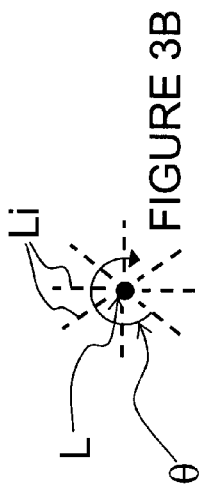

Referring to FIG. 3, the cellular misalignment of the renal nerves and the smooth muscle cells may be exploited to selectively affect renal nerve cells with reduced effect on smooth muscle cells. More specifically, because larger cells require less energy to exceed the irreversibility threshold of electroporation, several embodiments of electrodes of the present invention are configured to align at least a portion of an electric field generated by the electrodes with or near the longer dimensions of the cells to be affected. In specific embodiments, the extravascular device has electrodes configured to create an electrical field aligned with or near the lengthwise dimension L of the renal artery RA to affect renal nerves RN. By aligning an electric field so that the field preferentially affects the lengthwise aspect of the cell rather than the diametric or radial aspect of the cell, lower field strengths may be used to necrose cells. As mentioned above, this is expected to reduce power consumption and mitigate effects on non-target cells in the electric field.

Similarly, the lengthwise or longer dimensions of tissues overlying or underlying the target nerve are orthogonal or otherwise off-axis (e.g., transverse) with respect to the longer dimensions of the nerve cells. Thus, in addition to aligning the PEF with the lengthwise or longer dimensions of the target cells, the PEF may propagate along the lateral or shorter dimensions of the non-target cells (i.e., such that the PEF propagates at least partially out of alignment with non-target smooth muscle cells SMC). Therefore, as seen in FIG. 3, applying a PEF with propagation lines Li generally aligned with the longitudinal dimension L of the renal artery RA is expected to preferentially cause electroporation, electrofusion, denervation or other neuromodulation in cells of the target renal nerves RN without unduly affecting the non-target arterial smooth muscle cells SMC. The pulsed electric field may propagate in a single plane along the longitudinal axis of the renal artery, or may propagate in the longitudinal direction along any angular segment 9 through a range of 0"-360".

Embodiments of the method shown in FIG. 3 may have particular application with the extravascular methods and apparatus of the present invention. For instance, a PEF system placed exterior to the renal artery may propagate an electric field having a longitudinal portion that is aligned to run with the longitudinal dimension of the artery in the region of the renal nerves RN and the smooth muscle cell SMC of the vessel wall so that the wall of the artery remains at least substantially intact while the outer nerve cells are destroyed.

C. Embodiments of Systems and Additional Methods for Neuromodulation

FIG. 4 shows one embodiment of an extravascular pulsed electric field apparatus 200 in accordance with the present invention that includes one or more electrodes configured to deliver a pulsed electric field to renal neural fibers to achieve renal neuromodulation. Apparatus 200 comprises a laparoscopic or percutaneous PEF system having-probe 210 configured for insertion in proximity to the track of the renal neural supply along the renal artery or vein or hilum and/or within Gerota's fascia under, e.g., CT or radiographic guidance. The proximal section of probe 210 generally has an electrical connector to couple the probe to pulse generator 100, and the distal section has at least one electrode 212.

Pulsed electric field generator 100 is located external to the patient, and the electrode(s) 212 are electrically coupled to the generator via probe 210 and wires 211. The generator 100, as well as any of the electrode embodiments described herein, may be utilized with any embodiment of the present invention described hereinafter for delivery of a PEF with desired field parameters. It should be understood that electrodes of embodiments described hereinafter may be electronically connected to the generator, even if the generator is not explicitly shown or described with each embodiment.

The electrode(s) 212 can be individual electrodes, a common but segmented electrode, or a common and continuous electrode. A common but segmented electrode may, for example, be formed by providing a slotted tube fitted onto the electrode, or by electrically connecting a series of individual electrodes. Individual electrodes or groups of electrodes 212 may be configured to provide a bipolar signal. Electrodes 212 may be dynamically assignable to facilitate monopolar and/or bipolar energy delivery between any of the electrodes and/or between any of the electrodes and external ground pad 214. Ground pad 214 may, for example, be attached externally to the patient's skin, e.g., to the patient's leg or flank.

As seen in FIG. 4, electrode 212 may comprise a single electrode that is used in conjunction with separate patient ground pad 214 located external to the patient and coupled to generator 100 for monopolar use. Probe 210 optionally may comprise a conductive material that is insulated in regions other than its distal tip, thereby forming distal tip electrode 212. Alternatively, electrode 212 may, for example, be delivered through a lumen of probe 210. Probe 210 and electrode 212 may be of the standard needle or trocar-type used clinically for pulsed RF nerve block, such as those sold by Valleylab (a division of Tyco Healthcare Group LP) of Boulder, Colo. Alternatively, apparatus 200 may comprise a flexible and/or custom-designed probe for the renal application described herein.

In FIG. 4, percutaneous probe 210 has been advanced through percutaneous access site P into proximity within renal artery RA. Once properly positioned, pulsed electric field therapy may be applied to target neural fibers across electrode 212 and ground pad 214. After treatment, apparatus 200 may be removed from the patient to conclude the procedure.

It is expected that such therapy will alleviate clinical symptoms of CHF, hypertension, renal disease and/or other cardio-renal diseases for a period of months, potentially up to six months or more. This time period might be sufficient to allow the body to heal, for example, this period might reduce the risk of CHF onset after an acute myocardial infarction, thereby alleviating a need for subsequent re-treatment. Alternatively, as symptoms reoccur, or at regularly scheduled intervals, the patient might return to the physician for a repeat therapy.

The need for a repeat therapy optionally might be predicted by monitoring of physiologic parameters, for example, by monitoring specific neurohormones (plasma renin levels, etc.) that are indicative of increased sympathetic nervous activity. Alternatively, provocative maneuvers known to increase sympathetic nervous activity, such as head-out water immersion testing, may be conducted to determine the need for repeat therapy.

In some embodiments, apparatus 200 may comprise a probe having an introducer with an expandable distal segment having one or more electrodes. After insertion in proximity to target neural fibers, the distal segment may be opened or expanded into an expanded configuration. In one embodiment, this expanded configuration would follow a contour of the renal artery and/or vein to treat a number of neural fibers with a single application of PEF therapy. For example, in the expanded configuration, the distal segment may partially or completely encircle the renal artery and/or vein. In another embodiment, the expanded configuration may facilitate mechanical dissection, for example, to expand Gerota's fascia and create a working space for placement of the electrodes and/or for delivery of PEF therapy. The distal segment optionally may be translated independently of the probe or introducer.

When utilized as an electrode, the distal segment may, for example, be extended out of an introducer placed near the treatment area. The conducting distal segment maybe advanced out of the sheath until a desired amount of renal neural tissue is contacted; and then PEF therapy may be delivered via the distal segment electrode. Alternatively, the conducting distal segment may be allowed to reform or expand into a spiral of one or more loops, a random space-occupying shape, or another suitable configuration. Mesh, braid, or conductive gels or liquids could be employed in a similar manner.

Figure 5:
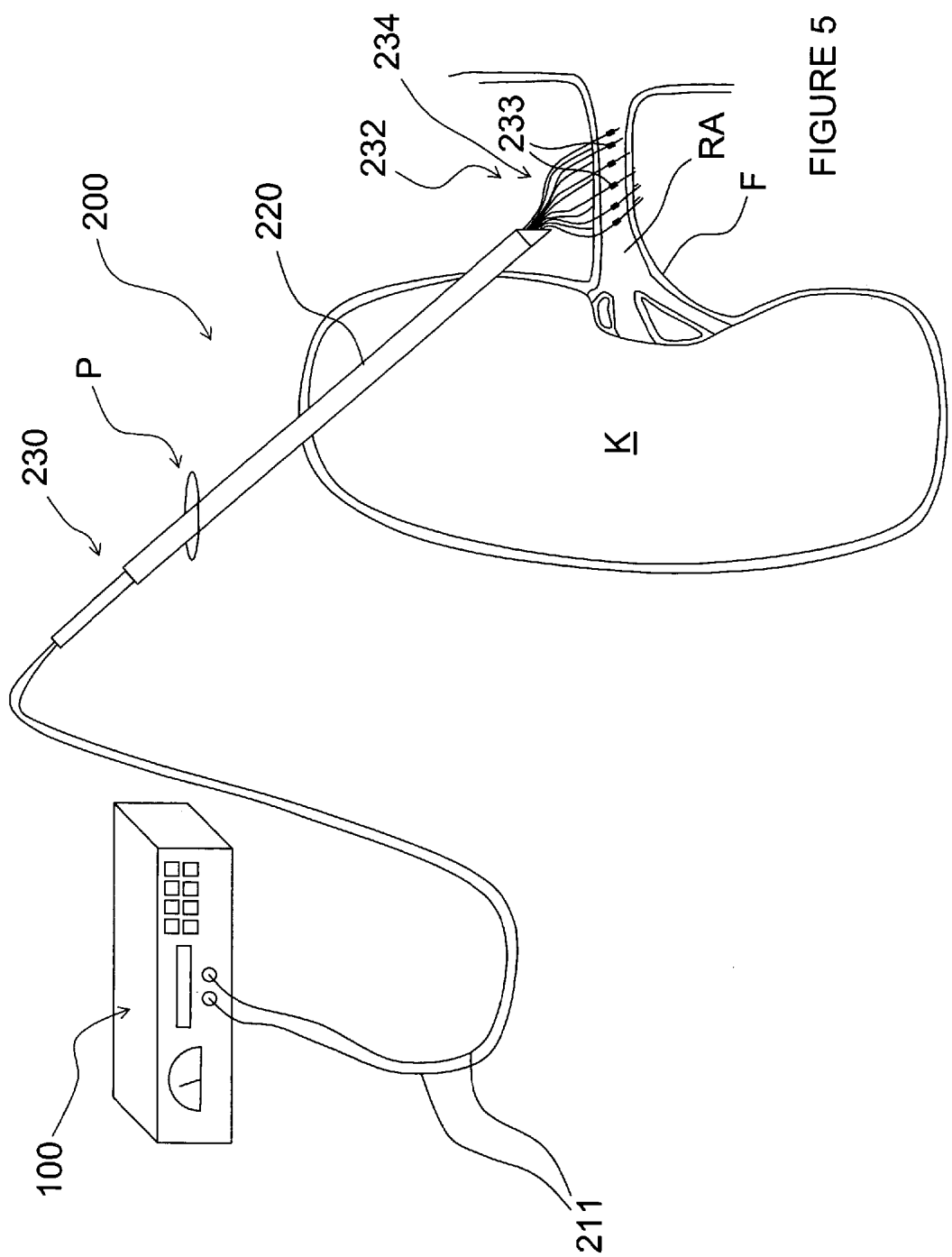
FIG. 5 is a schematic view illustrating another percutaneous or laparoscopic method and apparatus for renal neuromodulation comprising a spreading electrode for at least partially surrounding renal vasculature.

FIG. 5 illustrates another embodiment of apparatus 200 comprising an expandable distal segment. In FIG. 5, apparatus 200 comprises introducer probe 220 and electrode element 230 with a distal segment 232 that may be expandable. Probe 220 may, for example, comprise a standard, needle or trocar. Electrode element 230 is proximally coupled to generator 100 and is configured for advancement through probe 220. Distal segment 232 of the electrode element may be delivered to a treatment site in a closed or contracted configuration within probe 220 and then opened or expanded to a treatment configuration at or near the treatment site. For example, the distal segment 232 can be expanded by advancing segment 232 out of probe 220 and/or by retracting the probe relative to the distal segment. The embodiment of the distal segment 232 shown in FIG. 5 comprises a basket or cup-shaped element in a deployed configuration 234 for delivering treatment. The distal segment 232 preferably self-expands to the treatment configuration. The apparatus 200 can further include one or more electrodes 233 coupled to distal segment 232.

As seen in FIG. 5, distal segment 232 partially or completely encircles or surrounds renal artery RA in the deployed configuration 234. PEF therapy delivered through electrode element 230 to electrodes 233 in a bipolar or monopolar fashion may achieve a more thorough or complete renal neuromodulation than a PEF therapy delivered from electrodes along only one side of the artery or at an electrode at a single point along the artery. Electrode element 230 optionally may be electrically isolated from probe 220 such that the probe and electrodes 233 form two parts of a bipolar system in which the probe 220 is a return electrode.

With reference to FIG. 6, distal segment 232 alternatively may comprise a spiral element 236 in the treatment configuration. The distal segment may, for example, be preformed into a spiral configuration. The spiral might be straightened through a number of different mechanisms (e.g., positioning within probe 220, pull wires to actuate segment 232 between straight and spiraled, a shape-memory material, etc.) for insertion into proximity, e.g., with the renal vasculature. Once near a target vessel, the spiral may be actuated or allowed to reform in order to more fully encircle the vessel, thereby facilitating treatment of a greater number of neural fibers with a single application of PEF therapy.

The spiral or helical element 236 of distal segment 232 is configured to appose the vessel wall and bring electrode(s) 233 into close proximity to renal neural structures. The pitch of the helix can be varied to provide a longer treatment zone or to minimize circumferential overlap of adjacent treatments zones, e.g., in order to reduce a risk of stenosis formation. This pitch change can be achieved, for example, via (a) a heatset, (b) combining a plurality of segments of different pitches to form segment 232, (c) adjusting the pitch of segment 232 through the use of internal pull wires, (d) adjusting mandrels inserted into the segment, (e) shaping sheaths placed over the segment, or (f) any other suitable means for changing the pitch either in-situ or before introduction into the body.

As with previous embodiments, the electrode(s) 233 along the length of distal segment 232 can be individual electrodes, a common but segmented electrode, or a common and continuous electrode. A common and continuous electrode may, for example, comprise a conductive coil formed into or placed over the helix of distal segment 232. Individual electrodes or groups of electrodes 233 may be configured to provide a bipolar signal, or any configuration of the electrodes may be used together at a common potential in conjunction with a separate external patient ground for monopolar use. Electrodes 233 may be dynamically assignable to facilitate monopolar and/or bipolar energy delivery between any of the electrodes and/or between any of the electrodes and an external ground. Distal segment 232 optionally may be insulated on a side facing away from the renal artery such that at least portions of the side of the segment configured to face the renal artery are exposed to form electrode(s) 233.

Distal segment 232 of electrode element 230 may be delivered in proximity to renal artery RA in a low profile delivery configuration within probe 220. Once positioned in proximity to the artery, distal segment 232 may self-expand or may be expanded actively, e.g., via a pull wire or a balloon, into the spiral configuration 236 about the wall of the artery. The distal segment may, for example, be guided around the vessel, e.g., via steering and blunt dissection, and activated to take on the tighter-pitch coil of the spiral configuration 236. Alternatively or additionally, the distal segment might be advanced relative to probe 220 and snaked around the artery via its predisposition to assume the spiral configuration. Positioning the distal segment within Gerota's fascia might facilitate placement of distal segment 232 around the artery.

Once properly positioned, a pulsed electric field then may be generated by the PEF generator 100, transferred through electrode element 230 to electrodes 233, and delivered via the electrodes to renal nerves located along the artery. In many applications, the electrodes are arranged so that the pulsed electric field is aligned with the longitudinal dimension of the artery to modulate the neural activity along the renal nerves (e.g., denervation). This may be achieved, for example, via irreversible electroporation, electrofusion and/or inducement of apoptosis in the nerve cells.

Referring to FIG. 7, another percutaneous or laparoscopic method and apparatus for renal neuromodulation is described. In FIG. 7, distal segment 232 of electrode element 230 of apparatus 200 comprises electrode 233 having ring or cuff configuration 238. The ring electrode may partially surround renal artery RA, as shown. Electrode 233 optionally may comprise retractable pin 239 for closing the ring to more fully or completely encircle the artery once the electrode has been placed about the artery. A PEF therapy may be delivered via the electrode to achieve renal neuromodulation. As an alternative to laparoscopic placement, ring electrode 238 optionally may be surgically placed.

FIG. 8 illustrates another percutaneous or laparoscopic method and apparatus for renal neuromodulation comprising a spreading electrode configured for positioning near the renal hilum. As seen in FIG. 8, distal segment 232 of electrode element 230 may comprise fan-shaped member 240 having a plurality of fingers that may be collapsed or constrained within probe 220 during percutaneous introduction to, and/or retraction from, a treatment site. One or more electrodes 233 may be positioned along the fingers of the distal segment. Once in the area of the renal vasculature and/or renal hilum HI the fan may be extended, or probe 220 may be retracted, to deploy distal segment 232. The fingers, for example, spread out to cover a larger treatment area along the vasculature or renal hilum that facilitates treatment of a greater number of target neural fibers and/or creates a working space for subsequent introduction of electrodes 233.

In FIG. 8, a distal region of probe 220 is positioned in proximity to renal hilum HI and the fan-shaped distal segment 232 has been expanded to the deployed configuration. PEF therapy then may be delivered via electrodes 233 to neural fibers in that region for renal neuromodulation.

With reference to FIG. 9, distal segment 232 alternatively may comprise a tufted element 242 having one or more strands with electrodes 233. Distal segment 232 may be positioned in proximity to renal hilum H within probe 220, and then the tufted element 242 can be expanded to a space-occupying configuration. Electrodes 233 then may deliver PEF therapy to renal nerves.

With reference to FIG. 10, probe 220 optionally may pierce fascia F (e.g. Gerota's fascia) that surrounds kidney K and/or renal artery RA. Distal segment 232 may be advanced through probe 220 between the fascia and renal structures, such as hilum H and artery RA. This may position electrodes 233 into closer proximity with target renal neural structures. For example, when distal segment 232 comprises the fan-shaped member 240 of FIG. 8 or the tufted element 242 of FIG. 9, expansion of the distal segment within fascia F may place electrodes 233 into proximity with more target renal neural structures and/or may create a working space for delivery of one or more electrodes 233 or of conducting gels or liquids, etc.

Referring to FIGS. 11A and 11B, methods and apparatus for mechanically anchoring probe 220, distal segment 232 of electrode element 230, and/or electrode(s) 233 within fascia F are described. FIGS. 11A and 11B illustrate mechanical anchoring element 250 in combination with distal segment 232 of electrode element 230, but this should in no way be construed as limiting because the apparatus 200 does not need to include the anchoring element 250. In embodiments with the anchoring element, distal segment 232 may be expandable or non-expansile.

In the embodiment of Figure IIA, distal segment 232 comprises anchoring element 250 having collar 252 disposed about the distal segment. Self-expanding wire loops 254 of the anchoring element extend from the collar. The loops 254 may be collapsed against the shaft of distal segment 232 while the distal segment is disposed within probe 220 (as illustrated in dotted profile in FIG. 1 IA). Probe 220 may pierce the fascia near a treatment site, thereby positioning a distal tip of the probe within the fascia. The probe then may be retracted relative to electrode element 230 (and/or the electrode element may be advanced relative to the probe) to position distal segment 232 distal of the probe. The loops 254 self-expand in a manner that mechanically anchors distal segment 232 within the fascia. Alternatively, anchoring element 250 may be actively expanded, e.g., in a mechanical fashion.

The loops 254 optionally may be covered with an elastic polymer, such as silicone, CFlex, urethane, etc., such that the anchoring element 250 at least partially seals an entry site into fascia F. This may facilitate immediate infusion of fluids through probe 220 or electrode element 230 without leakage or with reduced leakage. Additionally or alternatively, when electrode element 230 is configured for longer-term implantation, anchoring element 250 may be covered in a porous material, such as a polyester fabric or mesh, that allows or promotes tissue in-growth. Tissue in-growth may enhance the anchoring providing by element 250 for maintaining the position of distal segment 232 and/or electrode(s) 233. Tissue in-growth may also enhance sealing at the entry site into the fascia.

In the embodiment of Figure I I B, distal segment 232 is cut in the longitudinal direction to create a series of flaps 256 around the catheter that form an alternative anchoring element 250. Pull-wire 258 may, for example, extend along the exterior of electrode element 230 or may be disposed within a lumen of the electrode element, and is coupled to distal segment 232 distal of flaps 256. Once distal segment 232 is positioned within fascia F, pull-wire 258 is moved proximally to extend the flaps 256 and anchor the distal segment within the fascia. Alternatively, other expandable members incorporating wires, baskets, meshes, braids or the like may be mechanically expanded to provide anchoring.

With anchoring element 250 expanded, an infusate optionally may be infused through slits 256. Furthermore, as with the embodiment of FIG. 1 IA, anchoring element 250 of FIG. 11 B optionally may be covered with an elastic polymer covering to create a gasket for sealing the entry site into the fascia. In such a configuration, infusion holes may be provided distal of the anchoring element. Alternatively, a proximal portion of the slit section of anchoring element 250 may be covered with the elastic polymer, while a distal portion remains uncovered, for example, to facilitate infusion through slits 256. In another embodiment, anchoring element 250 of FIG. 11B may comprise a porous material to facilitate tissue in-growth, as described previously. As with the elastic polymer, the porous material optionally may cover only a portion of the anchoring element to facilitate, for example, both tissue in-growth and infusion.

FIG. 12 shows a method and apparatus for renal neuromodulation in which electrodes are positioned along a patient's renal vasculature within an annular space between the vasculature and the surrounding fascia. The electrodes may be positioned in proximity to the renal artery and/or the renal vein by guiding a needle within fascia F using, for example, Computed Tomography ("CT") guidance. The needle may comprise introducer probe 220, or the probe may be advanced over and exchanged for the needle after placement of the needle within the fascia.

When the probe 220 is within the Gerota's fascia, the electrode element 230 is delivered through the probe in close proximity to renal vasculature (e.g., the renal artery RA). The electrode element optionally may be advanced along the length of the artery toward the patient's aorta to bluntly dissect a space for the electrode element as the electrode element is advanced. The electrode element 230 may comprise a catheter, and electrodes 233 coupled to the electrode element 230 may deliver PEF therapy or other types of therapy to renal neural structures located along the renal artery. Bipolar or monopolar electrode(s) may be provided as desired.

With reference to FIGS. 13A-C, various additional embodiments of electrodes 233 and distal segment 232 of electrode element 230 are described. In FIG. 13A, electrodes 233 comprise a pair of bipolar electrode coils disposed about distal segment 232. In FIG. 136, electrodes 233 comprise a pair of bipolar electrodes having contoured metal plates disposed on the side of distal segment 232 facing renal artery RA to face target renal neural structures. This is expected to preferentially direct PEF therapy delivered between electrodes 233 towards the renal artery. As seen in FIG. 13C, distal segment 232 and/or electrodes 233 may comprise a concave profile so that more surface area of the electrodes is juxtaposed with the wall of the renal artery. When the pulsed electric field delivered by electrodes 233 is strong enough, suitably directed and/or in close enough proximity to target neural structures, it is expected that the electrodes may achieve a desired level of renal neuromodulation without fully encircling the renal artery.

FIGS. 14A-C show another method and apparatus for positioning electrodes along the patient's renal artery. In addition to probe 220 and electrode element 230, apparatus 200 of FIGS. 14A-C comprises catheter 300. Electrode element 230 is positioned within catheter 300 and optionally may comprise an atraumatic tip of the catheter. As seen in FIG. 14A, catheter 300 may be advanced through probe 220 within the annular space between the fascia F and the renal vasculature shown as renal artery RA. The catheter and/or the probe optionally may be advanced over a guidewire. Various agents may be infused through the catheter to create a working space for advancement of the catheter and/or to facilitate placement of electrodes 233.

Once positioned as desired at a treatment site, the catheter may be retracted relative to the electrode element to expose electrodes 233 along distal segment 232 of the electrode element, as in FIG. 140. The electrodes 233 in FIGS. 14A-C may comprise a bipolar pair of expandable electrodes that may be collapsed for delivery within catheter 300. The electrodes may, for example, be fabricated from a self-expanding material, such as spring steel or Nitinol. Although electrodes 233 illustratively are on a common electrode element 230, it should be understood that multiple electrode elements 230 each having one or more electrodes 233 may be delivered through catheter 300 and positioned as desired along the renal vasculature.

In the expanded configuration of FIG. 146, electrodes 233 at least partially surround or encircle renal artery RA. It is expected that at least partially encircling the renal artery during PEF therapy will enhance the efficacy of renal neuromodulation or denervation. The electrodes may be used to deliver PEF therapy and/or to stimulate a physiologic response to test or to challenge an extent of neuromodulation, as well as to apply energy to disrupt, modulate or block renal nerve function. Various agents may be infused in the vicinity of electrodes 233 prior to, during or after energy delivery, for example, to aid in conduction (e.g., saline and hypertonic saline), to improve electroporative effect (e.g., heated solutions) or to provide protection to non-target cells (e.g., cooling solutions or Poloxamer-188).

Electrodes 233 may, for example, comprise coils, wires, ribbons, polymers, braids or composites. Polymers may be used in combination with conductive materials to direct a pulsed electric field into and/or along target tissue while insulating surrounding tissue. With reference to FIG. 14C, distal segment 232 of electrode element 230 may comprise insulation I that is locally removed or omitted along an inner surface of electrodes 233 where the electrodes face or contact renal vasculature.

Referring now to FIGS. 15A-B, another embodiment of the apparatus and method of FIGS. 14A-C is described. As seen in FIG. 15A, electrode(s) 233 may comprise an undulating or sinusoidal configuration that extends along the renal vasculature. The sinusoidal configuration of electrodes 233 may provide for greater contact area along the vessel wall than do electrodes 233 of FIGS. 14A-C, while still facilitating sheathing of electrode element 230 within catheter 300 for delivery and/or retrieval. Electrode(s) 233 may comprise a unitary electrode configured for monopolar energy delivery, or distal segment 232 of electrode element 230 may comprise insulation that is locally removed or omitted to expose electrodes 233. Alternatively, as seen in FIG. 15B, the electrodes may comprise discrete wire coils or other conductive sections attached to the undulating distal segment 232. Electrodes 233 may be energized in any combination to form a bipolar electrode pair.

FIG. 16 is a schematic view illustrating yet another embodiment of the method and apparatus of FIGS. 14A-C. In FIG. 16, catheter 300 comprises multiple lumens 304 through which electrode elements 230 may be advanced and electrodes 233 may be collapsed for delivery. When positioned at a treatment site, electrode elements 230 may be advanced relative to catheter 300 and/or the catheter 300 may be retracted relative to the electrode elements, such that electrodes 233 expand to the configuration of FIG. 16 for at least partially encircling renal vasculature. In FIG. 16, apparatus 200 illustratively comprises two electrode elements 230, each having an expandable electrode 233. The two electrodes 233 may be used as a bipolar electrode pair during PEF therapy. Electrode elements 230 may be translated independently, such that a separation distance between electrodes 233 may be altered dynamically, as desired.

FIGS. 17A-B show still another embodiment of the method and apparatus of FIGS. 14A-C. In FIG. 17A, electrode 233 comprises a panel that may be rolled into scroll for low-profile delivery within catheter 300. As seen in FIG. 178, the catheter may be retracted relative to the electrode, and/or the electrode may be advanced relative to the catheter, such that panel unfurls or unrolls, preferably in a self-expanding fashion, to partially or completely encircle renal artery RA. PEF therapy may be delivered through electrode 233 in a monopolar fashion, or the electrode may be segmented to facilitate bipolar use. Alternatively, a second electrode may be delivery in proximity to electrode 233 for bipolar PEF therapy.

Any of the electrode embodiments 212 or 233 of FIGS. 5-17B may be configured for use in a single PEF therapy session, or may be configured for implantation for application of follow-on PEF therapy sessions. In implantable embodiments, leads may, for example, extend from electrodes 212 or 233 to a subcutaneous element controllable through the skin or to an implantable controller.

With reference to FIG. 18, when electrodes 233 are configured for implantation, distal segment 232 of electrode element 230 may, for example, be detachable at a treatment site, such that electrodes 233 are implanted in the annular space between renal artery RA and fascia F, while a proximal portion of electrode element 230 is removed from the patient. As seen in FIG. 18, electrode element 230 may comprise leads 260 for tunneling to a subcutaneous element or to an implantable controller. The electrode element further comprises detachment mechanism 270 disposed just proximal of distal segment 232 for detachment of the distal segment at the treatment site. Distal segment 232 optionally may comprise elements configured to promote tissue in-growth in the vicinity of electrodes 233.

Figure 19B:
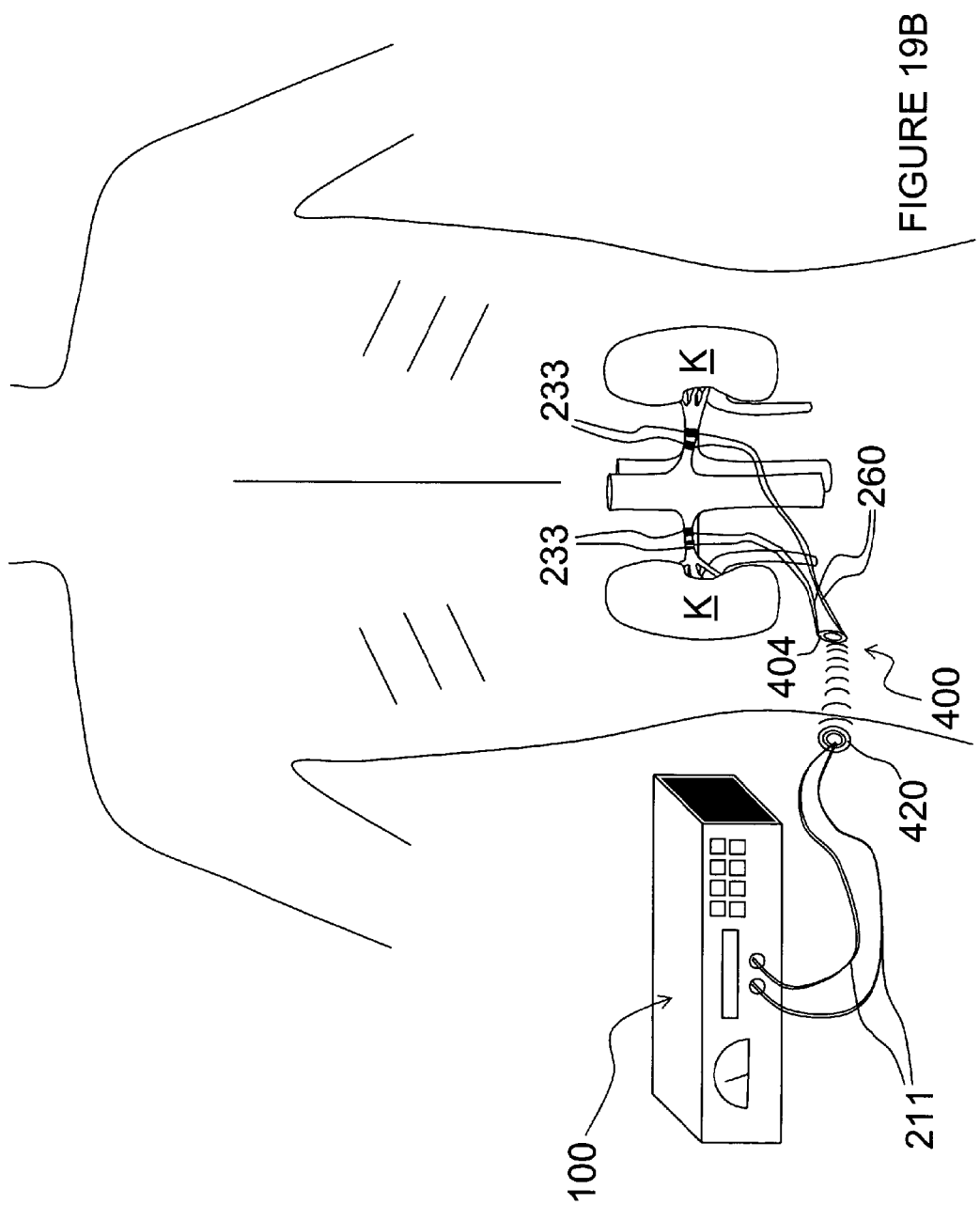

With reference to FIGS. 19A-20, partially and completely implantable PEF systems are described. FIGS. 19A-B illustrate partially implantable systems having a pulsed electric field generator 100 connected either directly or indirectly to a subcutaneous element 400 through or across the patient's skin. Subcutaneous element 400 may be placed, for example, posteriorly, e.g., in the patient's lower back. In FIGS. 19A-B, the subcutaneous element 400 is attached to leads 260, and the leads 260 are electrically coupled to implanted electrodes 233 positioned in proximity to the renal artery, renal vein, renal hilum, Gerota's fascia or other suitable structures. Electrodes 233 can be located bilaterally, i.e., in proximity to both the right and left renal vasculature, but alternatively may be positioned unilaterally. Furthermore, multiple electrodes may be positioned in proximity to either or both kidneys for bipolar PEF therapy, or monopolar electrodes may be provided and used in combination with a return electrode, such as external ground pad 214 or a return electrode integrated with subcutaneous element 400.

As seen in FIG. 19A, subcutaneous element 400 may comprise a subcutaneous port 402 having an electrical contact 403 comprising one or more connecting or docking points for coupling the electrical contact(s) to generator 100. In a direct method of transmitting a PEF across the patient's skin, a transcutaneous needle, trocar, probe or other element 410 that is electrically coupled to generator 100 pierces the patient's skin and releasably couples to contact 403. Transcutaneous element 410 conducts PEF therapy from the generator 100 across or through the patient's skin to, subcutaneous contact 403 and to electrodes 233 for modulating neural fibers that contribute to renal function. The implanted system might also incorporate an infusion lumen to allow drugs to be introduced from subcutaneous port 402 to the treatment area.

In addition to direct methods of transmitting PEF signals across the patient's skin, such as via transcutaneous element 410, indirect methods alternatively may be utilized, such as transcutaneous energy transfer ("TET") systems. TET systems are used clinically to recharge batteries in rechargeable implantable stimulation or paving devices, left ventricular assist devices, etc. In the TET embodiment of FIG. 19B, subcutaneous element 400 comprises subcutaneous receiving element 404, and external TET transmitting element 420 is coupled to generator 100. A PEF signal may be transmitted telemetrically through the skin from external transmitting element 420 to subcutaneous receiving element 404. Passive leads 260 connect the subcutaneous receiving element to nerve electrodes 233 and may conduct the signal to the nerves for treatment.

With reference to FIG. 20, a fully implantable PEF system is described. In FIG. 20, subcutaneous receiving element 404 is coupled to a capacitor or other energy storage element 430, such as a battery, which in turn is coupled to implanted controller 440 that connects via leads 260 to electrodes 233. External transmitting element 420 is coupled to external charger and programmer 450 for transmitting energy to the implanted system and/or to program the implanted system. Charger and programmer 450 need not supply energy in the form of a PEF for transmission across the patient's skin from external element 420 to receiving element 404. Rather, controller 440 may create a PEF waveform from energy stored within storage element 430. The controller optionally may serve as a return electrode for monopolar-type PEF therapy.

The embodiment of FIG. 20 illustratively is rechargeable and/or reprogrammable. However, it should be understood that the fully implanted PEF system alternatively may be neither rechargeable nor programmable. Rather, the system may be powered via storage element 430, which, if necessary, may be configured for surgical replacement after a period of months or years after which energy stored in the storage element has been depleted.

When using a percutaneous or implantable PEF system, the need for repeat therapy, the location for initial therapy and/or the efficacy of therapy, optionally may be determined by the system. For example, an implantable system periodically may apply a lower-frequency stimulation signal to renal nerves; when the nerve has returned toward baseline function, the test signal would be felt by the patient, and the system would apply another course of PEF therapy. This repeat treatment optionally might be patient initiated: when the patient feels the test signal, the patient would operate the implantable system via electronic telemetry, magnetic switching or other means to apply the required therapeutic PEF.

As an alternative or in addition to eliciting a pain response, the responses of physiologic parameters known to be affected by stimulation of the renal nerves may be monitored. Such parameters comprise, for example, renin levels, sodium levels, renal blood flow and blood pressure. When using stimulation to challenge denervation and monitor treatment efficacy, the known physiologic responses to stimulation should no longer occur in response to such stimulation.

Efferent nerve stimulation waveforms may, for example, comprise frequencies of about 1-10 Hz, while afferent nerve stimulation waveforms may, for example, comprise frequencies of up to about 50 Hz. Waveform amplitudes may, for example, range up to about 50V1 while pulse durations may, for example, range up to about 20 milliseconds. Although exemplary parameters for stimulation waveforms have been described, it should be understood that any alternative parameters may be utilized as desired.

The electrodes used to deliver PEFs in any of the previously described variations of the present invention also may be used to deliver stimulation waveforms to the renal vasculature. Alternatively, the variations may comprise independent electrodes configured for stimulation. As another alternative, a separate stimulation apparatus may be provided.

As mentioned, one way to use stimulation to identify renal nerves is to stimulate the nerves such that renal blood flow is affected—or would be affected if the renal nerves had not been denervated or modulated. As stimulation acts to reduce renal blood flow, this response may be attenuated or abolished with denervation. Thus, stimulation prior to neural modulation would be expected to reduce blood flow, while stimulation after neural modulation would not be expected to reduce blood flow to the same degree when utilizing similar stimulation parameters and location(s) as prior to neural modulation. This phenomenon may be utilized to quantify an extent of renal neuromodulation.

Embodiments of the present invention may comprise elements for monitoring renal blood flow or for monitoring any of the other physiological parameters known to be affected by renal stimulation. Renal blood flow optionally may be visualized through the skin (e.g., using an ultrasound transducer). An extent of electroporation additionally or alternatively may be monitored directly using Electrical Impedance Tomography ("EIT") or other electrical impedance measurements or sensors, such as an electrical impedance index.

In addition or as an alternative to stimulation, other monitoring methods which check for measures of the patient's clinical status may be used to determine the need for repeat therapy. These monitoring methods could be completely or partially implantable, or they could be external measurements which communicate telemetrically with implantable elements. For instance, an implantable pressure sensor of the kind known in the field (e.g., sensors developed by CardioMEMS of Atlanta, Ga.) could measure right atrial pressure. Increasing right atrial pressure is a sign of fluid overload and improper CHF management. If an increase in right atrial pressure is detected by the sensor, a signal might be sent to controller 440 and another PEF treatment would delivered. Similarly, arterial pressure might be monitored and/or used as a control signal in other disease conditions, such as the treatment of high blood pressure. Alternatively, invasive or non-invasive measures of cardiac output might be utilized. Non-invasive measures include, for example, thoracic electrical bioimpedance.

In yet another embodiment, weight fluctuation is correlated with percentage body fat to determine a need for repeat therapy. It is known that increasing patient weight, especially in the absence of an increase in percent body fat, is a sign of increasing volume overload. Thus, the patient's weight and percentage body fat may be monitored, e.g., via a specially-designed scale that compares the weight gain to percentage body fat. If it is determined that weight gain is due fluid overload, the scale or other monitoring element(s) could signal controller 440, e.g., telemetrically, to apply another PEF treatment.

When using partially or completely implantable PEF systems, a thermocouple, other temperature or impedance monitoring elements, or other sensors, might be incorporated into subcutaneous elements 400. External elements of the PEF system might be designed to connect with and/or receive information from the sensor elements. For example, in one embodiment, transcutaneous element 410 connects to subcutaneous electrical contact 403 of port 402 and can deliver stimulation signals to interrogate target neural tissue to determine a need, or parameters, for therapy, as well as to determine impedance of the nerve and nerve electrodes. Additionally, a separate connector to mate with a sensor lead may be extended through or alongside transcutaneous element 410 to contact a corresponding subcutaneous sensor lead.

Alternatively, subcutaneous electrical contact 403 may have multiple target zones placed next to one another, but electrically isolated from one another. A lead extending from an external controller, e.g., external generator 100, would split into several individual transcutaneous needles, or individual needle points coupled within a larger probe, which are inserted through the skin to independently contact their respective subcutaneous target zones. For example, energy delivery, impedance measurement, interrogative stimulation and temperature each might have its own respective target zone arranged on the subcutaneous system. Diagnostic electronics within the external controller optionally may be designed to ensure that the correct needle is in contact with each corresponding subcutaneous target zone.

Elements may be incorporated into the implanted elements of PEF systems to facilitate anchoring and/or tissue in-growth. For instance, fabric or implantable materials, such as Dacron or ePTFE, might be incorporated into the design of the subcutaneous elements 400 to facilitate in-growth into areas of the elements that would facilitate anchoring of the elements in place, while optionally repelling tissue in-growth in undesired areas, such as along electrodes 233. Similarly, coatings, material treatments, drug coatings or drug elution might be used alone or in combination to facilitate or retard tissue in-growth into various elements of the implanted PEF system, as desired.

Any of the embodiments of the present invention described herein optionally may be configured for infusion of agents into the treatment area before, during or after energy application, for example, to create a working space to facilitate electrode placement, to enhance or modify the neurodestructive or neuromodulatory effect of applied energy, to protect or temporarily displace non-target cells, and/or to facilitate visualization. Additional applications for infused agents will be apparent. If desired, uptake of infused agents by cells may be enhanced via initiation of reversible electroporation in the cells in the presence of the infused agents. The infusate may comprise, for example, fluids (e.g., heated or chilled fluids), air, C02, saline, heparinized saline, hypertonic saline, contrast agents, gels, conductive materials, space-occupying materials (gas, solid or liquid), protective agents, such as Poloxamer-188, anti-proliferative agents, or other drugs and/or drug delivery elements. Variations of the present invention additionally or alternatively may be configured for aspiration.

Figure 21A:
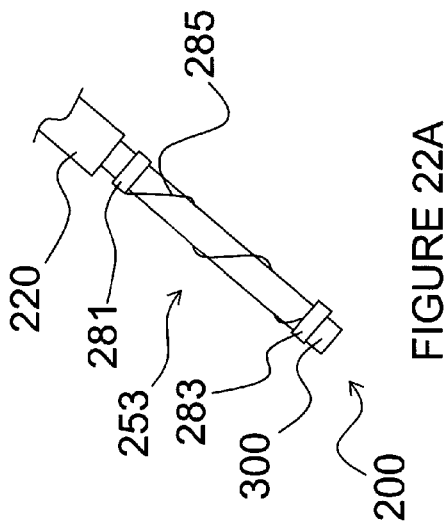
FIGS. 21A and 21B are schematic views illustrating a method and apparatus for positioning electrodes relative to a renal neural structure in accordance with another embodiment of the invention.
Figure 21B:
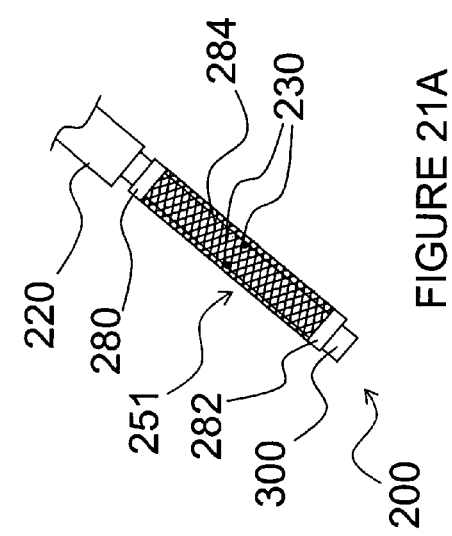

FIGS. 21A and 21B illustrate another embodiment of the apparatus 200 in accordance with the invention. Referring to FIG. 21A, the apparatus 200 includes the probe 220 and a catheter 300 received within the probe 220. The catheter 300 includes an anchoring mechanism 251 having a first collar 280, a second collar 282 located distally relative to the first collar 280, and an expandable member 284 connected to the first and second collars 280 and 282. The expandable member 284 can be a braid, mesh, woven member or other device that expands as the distance between the first and second collars 280 and 282 is reduced. The expandable member 284 can include polyesters, Nitinol, elgiloy, stainless steel, composites and/or other suitable materials. The collars 280 and 282, and/or the expandable member 284, may be at least partially covered in an expandable polymer to form a seal with the patient. The apparatus 200 can further include a plurality of electrodes 230 located at the expandable member 284 and/or the first or second collars 280 or 282.

The anchoring mechanism 250 operates by moving at least one of the collars 280 and 282 toward the other to reduce the distance between the collars. For example, the first collar 280 can be slidable along the catheter 300, and the second collar 282 can be fixed to the catheter 300. Referring to FIG. 21B, the expandable member 284 can be expanded by pulling back on the catheter 300 to engage the proximal collar 280 with the distal end of the probe 220. As the catheter 300 is withdrawn proximally relative to the probe 220, the distal end of the probe 220 drives the first collar 280 toward the second collar 282 to move the anchoring mechanism 251 from a collapsed position shown in FIG. 21A to an expanded configuration illustrated in FIG. 218. Alternatively, the apparatus 200 can include an actuator that can be advanced distally to drive the first collar 280 toward the second collar 282. The actuator, for example, can be a coaxial sleeve around the catheter 300 that may be operated from the proximal end of the probe 220.

Figure 22A:
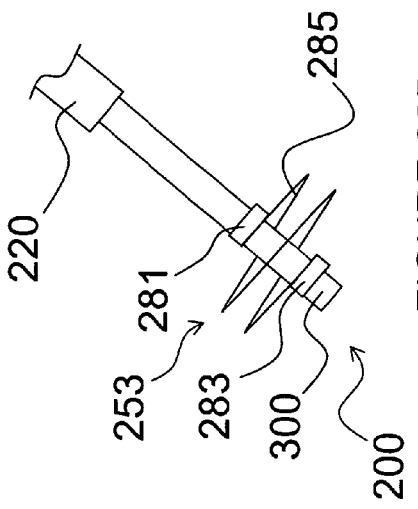
FIGS. 22A and 22B are schematic views illustrating a method and apparatus for positioning electrodes relative to a patient's renal neural structure in accordance with still another embodiment of the invention.
Figure 22B:
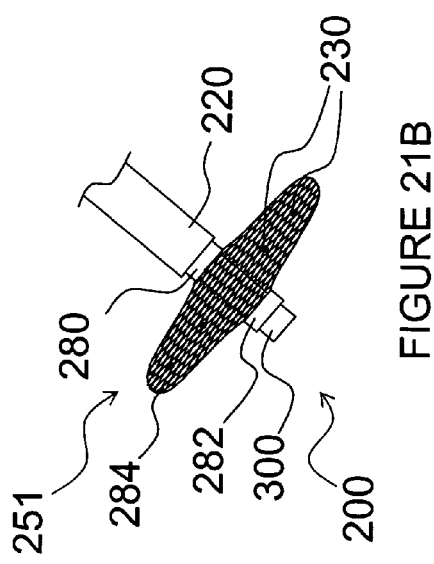

FIGS. 22A and 22B illustrate another embodiment of the apparatus 200 in accordance with the invention. In this embodiment, the apparatus 200 includes a probe 220 and a catheter 300 that moves through the probe 220 as described above with reference to FIGS. 11A-B. The apparatus 200 of this embodiment further includes an anchoring mechanism 253 having a first collar 281, a second collar 283 located distally along the catheter 300 relative to the first collar 281, and an expandable member 285 attached to the first and second collars 281 and 283. In one embodiment, the first collar 281 is slidably movable along the catheter 300, and the second collar 283 is fixed to the catheter 300. Alternatively, the first collar 281 can be fixed to the catheter 300 and the second collar 283 can be movable along the catheter 300. The expandable member 285 is a self-contracting member that is actively stretched into a collapsed configuration to be contained within the probe 220 for delivery to the desired treatment site in the patient. FIG. 22A illustrates the expandable member 285 stretched into an elongated state to be constrained within the probe 220. Referring to FIG. 22B, the apparatus 200 is deployed in the patient by moving the probe 220 proximally relative to the catheter 300 and/or moving the catheter 300 distally relative to the probe 220 until the expandable member 285 is outside of the probe 220. Once the expandable member 285 is outside of the probe 220, the expandable member 285 draws the movable collar toward the fixed collar to allow the expandable member 285 to expand outwardly relative to the radius of the catheter shaft 300.

The expandable member 285 can be a spring formed from a polyester, stainless steel, composites or other suitable materials with sufficient elasticity to inherently move into the expanded configuration shown in FIG. 228. Alternatively, the expandable member can be formed from a shaped memory metal, such as Nitinol or elgiloy, that moves from the collapsed configuration illustrated in FIG. 22A to the expanded configuration illustrated in FIG. 226 at a given temperature. In either embodiment the apparatus 200 can further include electrodes (not shown) located along the expandable member for delivering the pulsed electric field to the renal nerve or other structure related to renallcardio activity.

Figure 23:
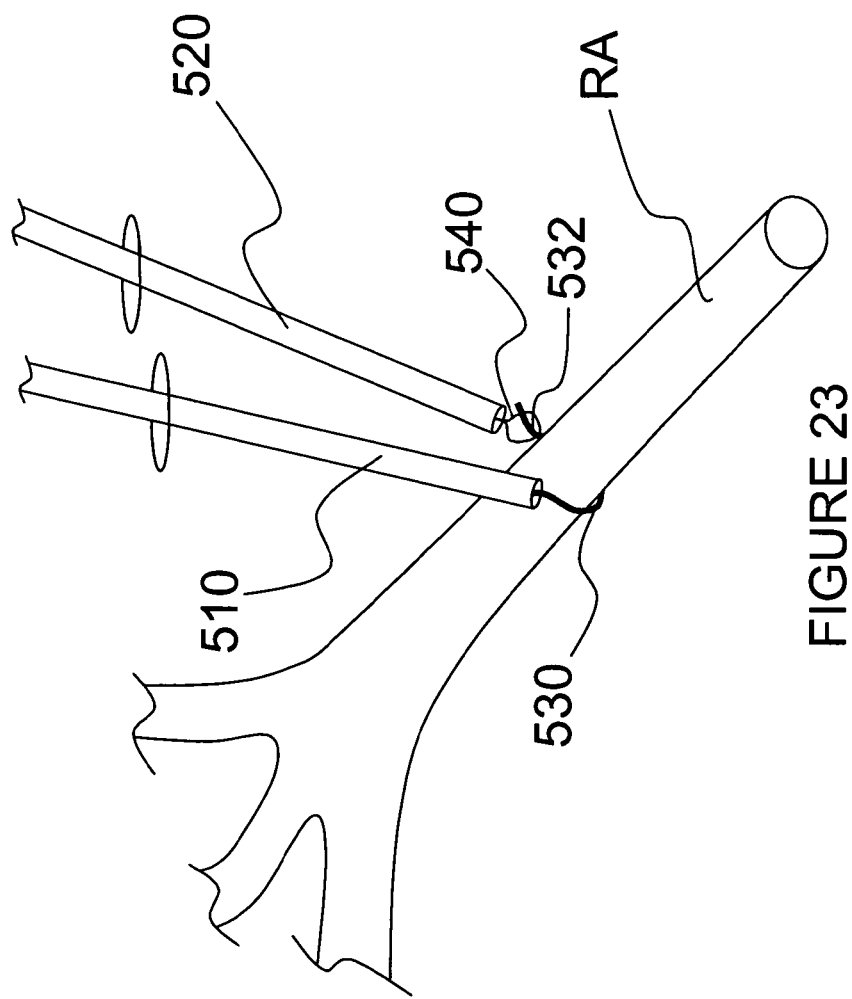
FIG. 23 is a schematic view illustrating a method and apparatus for positioning electrodes relative to a patient's renal neural structure in accordance with yet another embodiment of the invention.

FIG. 23 illustrates yet another embodiment of a method and apparatus for positioning an electrode relative to a renal structure to deliver a PEF for neuromodulation. In this embodiment, the apparatus includes a first percutaneous member 510, a second percutaneous member 520, an electrode assembly 530, and a retriever 540. The first percutaneous member 510 can be a first trocar through which the electrode assembly 530 is delivered to the renal artery RA or other renal structure, and the second percutaneous member 520 can be a second trocar through which the retriever 540 is delivered to the general region of the electrode assembly 530. In the embodiment shown in FIG. 23, the electrode assembly 530 includes an electrode 532, and the retriever 540 is a snare configured to capture the electrode assembly. In operation, the first percutaneous member 510 is inserted into the patient and the electrode assembly 530 is passed through the first percutaneous member 510 until the electrode 532 is at or near a desired location relative to the renal structure. The second percutaneous member 520 is also inserted into the patient so that the retriever 540 can engage the electrode assembly 530. The retriever 540 can be used to hold the electrode 532 at the desired location during delivery of a PEF to the patient and/or to remove the electrode assembly 530 after delivering the PEF.

Although preferred illustrative variations of the present invention are described above, it will be apparent to those skilled in the art that various changes and modifications may be made thereto without departing from the invention. For example, although the variations primarily have been described for use in combination with pulsed electric fields, it should be understood that any other electric field may be delivered as desired. It is intended in the appended claims to cover all such changes and modifications that fall within the true spirit and scope of the invention.

We claim:

1. A method for reducing blood pressure in a human patient, the method comprising:
   implanting a neural stimulation system in the patient below the patient's skin, wherein the neural stimulation system includes an electric field generator electrically coupled to a ring-shaped electrode positioned adjacent to target renal nerves innervating a kidney of the patient; and
   delivering generated electrical signals from the electric field generator to the target nerves via the ring-shaped electrode, thereby altering the naturally occurring neural signals propagating through the nerves,
   wherein delivering the generated electrical signals to the target nerves of the patient results in a therapeutically beneficial reduction in blood pressure of the patient.

2. The method of claim 1 wherein delivering generated electrical signals from the electric field generator to the target nerves via the ring-shaped electrode comprises delivering generated stimulation signals to the target nerves.

3. The method of claim 1 wherein delivering generated electrical signals from the electric field generator to the target nerves via the ring-shaped electrode comprises delivering at least two different levels of generated stimulation signals to the target nerves.

4. The method of claim 1 wherein delivering generated electrical signals from the electric field generator to the target nerves via the ring-shaped electrode comprises delivering intermittent stimulation to the target nerves.

5. The method of claim 1 wherein delivering generated electrical signals from the electric field generator to the target nerves via the ring-shaped electrode comprises delivering the electrical signals in a unipolar fashion.

6. The method of claim 1 wherein altering the naturally occurring neural signals propagating through the nerves comprises attenuating the neural signals along the target nerves.

7. The method of claim 1 wherein the ring-shaped electrode adjacent to the renal nerves at least partially surrounds a renal blood vessel of the patient.

8. The method of claim 1 wherein delivering generated electrical signals from the electric field generator to the target nerves via the ring-shaped electrode comprises decreasing renal sympathetic nerve activity of the patient.

9. The method of claim 1, further comprising monitoring at least one physiologic parameter of the patient with a sensor.

10. The method of claim 9, further comprising transmitting information regarding the monitored physiologic parameter from the sensor to a device located outside of the patient.

11. The method of claim 10 wherein the monitored physiologic parameter comprises at least one of blood pressure, renin levels, sodium levels, and renal blood flow.

12. The method of claim 10 wherein the monitored physiologic parameter is indicative of renal activity.

13. The method of claim 1 wherein the neural stimulation system further comprises an energy storage device electrically coupled to the electric field generator, and wherein the electric field generator is configured for recharging via the energy storage device.

14. The method of claim 1 wherein the neural stimulation system is configured to be reprogrammed after implantation in the patient.

* * * * *